US010207961B2

(12) United States Patent
Sreekumar et al.

(10) Patent No.: US 10,207,961 B2
(45) Date of Patent: Feb. 19, 2019

(54) METHODS FOR PRODUCING CYCLIC AND ACYCLIC KETONES

(71) Applicants: The Regents of the University of California, Oakland, CA (US); BP Corporation North America Inc., Houston, TX (US)

(72) Inventors: Sanil Sreekumar, Midland, MI (US); F. Dean Toste, Piedmont, CA (US); Amit A. Gokhale, Scotch Plains, NJ (US); Gorkem Gunbas, Ankara (TR) (US); Balakrishnan Madhesan, Tamil Nadu (IN); Alexis T. Bell, Oakland, CA (US); Eric Sacia, Wilmington, DE (US); George E. Arab, Berkeley, CA (US)

(73) Assignees: The Regents of the University of California, Oakland, CA (US); BP Corporation North America Inc., Houston, TX (US)

( * ) Notice: Subject to any disclaimer, the term of this patent is extended or adjusted under 35 U.S.C. 154(b) by 137 days.

(21) Appl. No.: 15/128,378

(22) PCT Filed: Mar. 23, 2015

(86) PCT No.: PCT/US2015/022086
§ 371 (c)(1),
(2) Date: Sep. 22, 2016

(87) PCT Pub. No.: WO2015/148412
PCT Pub. Date: Oct. 1, 2015

(65) Prior Publication Data
US 2018/0170824 A1  Jun. 21, 2018

Related U.S. Application Data

(60) Provisional application No. 61/969,761, filed on Mar. 24, 2014.

(51) Int. Cl.
| | | |
|---|---|---|
| C07C 1/22 | (2006.01) |
| C07C 13/00 | (2006.01) |
| C07C 45/74 | (2006.01) |
| C07D 307/46 | (2006.01) |
| C07C 1/207 | (2006.01) |
| C10L 1/04 | (2006.01) |
| C10G 3/00 | (2006.01) |
| C07C 13/18 | (2006.01) |
| C07C 15/113 | (2006.01) |
| C07C 49/203 | (2006.01) |
| C07C 49/603 | (2006.01) |
| C07C 49/613 | (2006.01) |
| C07C 49/657 | (2006.01) |

(52) U.S. Cl.
CPC .............. *C07C 1/22* (2013.01); *C07C 1/2076* (2013.01); *C07C 13/18* (2013.01); *C07C 15/113* (2013.01); *C07C 45/74* (2013.01); *C07C 49/203* (2013.01); *C07C 49/603* (2013.01); *C07C 49/613* (2013.01); *C07C 49/657* (2013.01); *C07D 307/46* (2013.01); *C10G 3/50* (2013.01); *C10L 1/04* (2013.01); *C07C 2521/08* (2013.01); *C07C 2521/10* (2013.01); *C07C 2521/18* (2013.01); *C07C 2523/20* (2013.01); *C07C 2523/46* (2013.01); *C07C 2523/648* (2013.01); *C07C 2527/18* (2013.01); *C07C 2529/70* (2013.01); *C07C 2601/14* (2017.05); *C07C 2601/16* (2017.05)

(58) Field of Classification Search
CPC ........... C07C 1/22; C07C 13/20; C07C 45/74; C07C 49/203
See application file for complete search history.

(56) References Cited

U.S. PATENT DOCUMENTS

| | | |
|---|---|---|
| 2,434,631 A | 1/1948 | Winkler et al. |
| 3,781,307 A | 12/1973 | Chabardes et al. |
| 4,250,259 A | 2/1981 | Hou et al. |
| 8,075,642 B2 | 12/2011 | Dumesic et al. |
| 2005/0089979 A1 | 4/2005 | Ezeji et al. |
| 2007/0275447 A1 | 11/2007 | Lewis et al. |
| 2008/0015395 A1 | 1/2008 | D'Amore et al. |
| 2008/0015397 A1 | 1/2008 | D'Amore et al. |
| 2008/0103337 A1 | 5/2008 | D'Amore et al. |
| 2008/0132730 A1 | 6/2008 | Manzer et al. |
| 2008/0244961 A1 | 10/2008 | Rusek et al. |

(Continued)

FOREIGN PATENT DOCUMENTS

| | | |
|---|---|---|
| CN | 101440381 A | 5/2009 |
| CN | 101787378 A | 7/2010 |

(Continued)

OTHER PUBLICATIONS

Stoilkova et al., "Hydrotalcite as a Base Catalyst in Aldol Condensation", Annuaire De L'Universite De Sofia "St. Kliment Ohridski", 2009, pp. 175-178.

(Continued)

*Primary Examiner* — Sikarl A Witherspoon
(74) *Attorney, Agent, or Firm* — Morrison & Foerster LLP

(57) ABSTRACT

Provided herein are methods for producing cyclic and acyclic ketones from trimerization and dimerization of alkyl ketones, including for example methyl ketones. Such cyclic and acyclic ketones may be suitable for use as fuel and lubricant precursors, and may be hydrodeoxygenated to form their corresponding cycloalkanes and alkanes. Such cycloalkanes and alkanes may be suitable for use as fuels, including jet fuels, and lubricants.

35 Claims, 17 Drawing Sheets

(56) References Cited

U.S. PATENT DOCUMENTS

| | | |
|---|---|---|
| 2008/0248540 A1 | 10/2008 | Yang |
| 2009/0030239 A1 | 1/2009 | D'Amore et al. |
| 2009/0036716 A1 | 2/2009 | D'Amore et al. |
| 2010/0076233 A1 | 3/2010 | Cortright et al. |
| 2010/0077655 A1 | 4/2010 | Bauldreay et al. |
| 2010/0204526 A1 | 8/2010 | Kouba et al. |
| 2010/0263265 A1 | 10/2010 | Delfort et al. |
| 2010/0268005 A1 | 10/2010 | Rusek et al. |
| 2010/0330633 A1 | 12/2010 | Walther et al. |
| 2011/0172475 A1 | 7/2011 | Peters et al. |
| 2011/0237833 A1 | 9/2011 | Koltermann et al. |
| 2011/0306801 A1 | 12/2011 | Schucker |

FOREIGN PATENT DOCUMENTS

| | | |
|---|---|---|
| CN | 102203217 A | 9/2011 |
| DE | 2257675 A1 | 5/1974 |
| EP | 0719751 A1 | 7/1996 |
| EP | 0828558 B1 | 12/2001 |
| GB | 400384 A | 10/1933 |
| GB | 723280 A | 2/1955 |
| WO | 1998/51813 A1 | 11/1998 |
| WO | 2007/149397 A2 | 12/2007 |
| WO | 2008/066579 A1 | 6/2008 |
| WO | 2008/066581 A1 | 6/2008 |
| WO | 2008/109877 A1 | 9/2008 |
| WO | 2008/111941 A2 | 9/2008 |
| WO | 2008/156320 A1 | 12/2008 |
| WO | 2009/152495 A2 | 12/2009 |
| WO | 2010/098694 A2 | 9/2010 |
| WO | 2011/077242 A1 | 6/2011 |
| WO | 2011/143392 A1 | 11/2011 |
| WO | 2012/001416 A1 | 1/2012 |
| WO | 2012/001417 A1 | 1/2012 |
| WO | 2012/166267 A2 | 12/2012 |
| WO | 2012/166267 A3 | 4/2013 |

OTHER PUBLICATIONS

Sreekumar et al., "Chemocatalytic Upgrading of Tailored Fermentation Products Toward Biodiesel", ChemSusChem, vol. 7, 2014, pp. 2445-2448.

Alonso et al., "Catalytic Conversion of Biomass to Biofuels", Green Chemistry, vol. 12, 2010, pp. 1493-1513.

Gines et al., "Bifunctional Condensation Reactions of Alcohols on Basic Oxides Modified by Copper and Potassium", Journal of Catalysis, vol. 176, 1998, pp. 155-172.

Paulis et al., "Preparation and Characterization of Niobium Oxide for the Catalytic Aldol Condensation of Acetone", Applied Catalysis A: General, vol. 180, 1999, pp. 411-420.

Veloso et al., "Aldol Condensation of Acetone Over Alkali Cation Exchanged Zeolites", Studies in Surface Science and Catalysis, vol. 84, 1994, pp. 1913-1920.

Zhang et al., "Aldol Addition of Acetone, Catalyzed by Solid Base Catalysts: Magnesium Oxide, Calcium Oxide, Strontium Oxide, Barium Oxide, Lanthanum (III) Oxide and Zirconium Oxide", Applied Catalysis, vol. 36, 1988, pp. 189-197.

Alonso et al., "The α-Alkylation of Methyl Ketones with Primary Alcohols Promoted by Nickel Nanoparticles under Mild and Ligand-less Conditions", Synlett, No. 12, 2007, pp. 1877-1880.

Das et al., "Influence of the Metal Function in the "One-Pot" Synthesis of 4-Methyl-2-Pentanone (Methyl Isobutyl Ketone) from Acetone Over Palladium Supported on Mg(Al)O Mixed Oxides Catalysts", Catalysis Letters, vol. 71, No. 3-4, Feb. 2001, pp. 181-185.

Debecker et al., "Exploring, Tuning, and Exploiting the Basicity of Hydrotalcites for Applications in Heterogeneous Catalysis", Chemistry A European Journal, vol. 15, 2009, pp. 3920-3935.

Demirbas, A, "The Importance of Bioethanol and Biodiesel from Biomass", Energy Sources, Part B, vol. 3, 2008, pp. 177-185.

Ekeley et al., "The Condensation Products of Diethyl Ketone", Journal of the American Chemical Society, vol. 46, Feb. 1924, pp. 447.

Hamid et al., "Borrowing Hydrogen in the Activation of Alcohols", Advanced Synthesis & Catalysis, vol. 349, 2007, pp. 1555-1575.

He et al., "One-Step Synthesis of 2-Pentanone from Ethanol Over K-Pd/MnOx—ZrO2—ZnO Catalyst", Journal of Molecular Catalysis A: Chemical, vol. 226, 2005, pp. 89-92.

International Preliminary Report on Patentability received for PCT Patent Application No. PCT/US2012/035306, dated Dec. 12, 2013, 11 pages.

International Preliminary Report on Patentability received for PCT Patent Application No. PCT/US2014/035545, dated Nov. 5, 2015, 13 pages.

International Search Report and Written Opinion received for PCT Patent Application No. PCT/US2012/035306, dated Feb. 13, 2013, 16 pages.

International Search Report and Written Opinion received for PCT Patent Application No. PCT/US2014/035545 dated Nov. 24, 2014, 18 pages.

International Search Report and Written Opinion received for PCT Patent Application No. PCT/US2015/022086, dated Sep. 29, 2015, 14 pages.

Invitation to Pay Additional Fee received for PCT Patent Application No. PCT/US2015/022086, dated Jul. 22, 2015, 4 pages.

Kim et al., "Recyclable Gold Nanoparticle Catalyst for the Aerobic Alcohol Oxidation and C—C Bond Forming Reaction between Primary Alcohols and Ketones under Ambient Conditions", Tetrahedron, vol. 65, 2009, pp. 1461-1466.

Kwon et al., "Recyclable Palladium Catalyst for Highly Selective α Alkylation of Ketones with Alcohols", Angewandte Chemie, vol. 44, 2005, pp. 6913-6915.

Non-Final Office Action received for U.S. Appl. No. 14/123,064, dated Jan. 4, 2016, 10 pages.

Non-Final Office Action received for U.S. Appl. No. 14/123,064, dated Jul. 15, 2016, 10 pages.

Requirement for Restriction/Election received for U.S. Appl. No. 14/786,153, dated Aug. 30, 2016, 10 pages.

Roffler et al., "Design and Mathematical Description of Differential Contactors Used in Extractive Fermentations", Biotechnology and Bioengineering, vol. 32, Jul. 1988, pp. 192-204.

Roffler et al., "In Situ Extractive Fermentation of Acetone and Butanol", Biotechnology and Bioengineering, vol. 31, Feb. 1988, pp. 135-143.

Roffler et al., "In-Situ Recovery of Butanol during Fermentation", Bioprocess Engineering, vol. 2, 1987, pp. 1-12.

Roffler et al., "In-Situ Recovery of Butanol during Fermentation", Bioprocess Engineering, vol. 2, 1987, pp. 181-190.

Seebald et al., "Reaktionen an Aluminiumoxiden. 2. Mitt.: Umsetzungen von Butan-2-on an Aluminiumoxid", Arch. Pharmaz., vol. 305, No. 10, 1972, pp. 785-793. (English Abstract Only).

Shimizu et al., "Direct C—C Cross-Coupling of Secondary and Primary Alcohols Catalyzed by a y-Alumina-Supported Silver Subnanocluster", Angewandte Chemie International Edition, vol. 48, 2009, pp. 3982-3986.

Shuikin et al., "Activity of Copper- And Iron-Containing Catalysts in the Reaction of Isophorone with Ammonia and Hydrogen", Petroleum Chemistry, vol. 36, No. 2, 1996, pp. 174-179.

Yamada et al., "A Solid-Phase Self-Organized Catalyst of Nanopalladium with Main-Chain Viologen Polymers: α-Alkylation of Ketones with Primary Alcohols", Organic Letters, vol. 8, No. 7, 2006, pp. 1375-1378.

Yamada et al., "Development of a Convoluted Polymeric Nanopalladium Catalyst: α-Alkylation of Ketones and Ring-Opening Alkylation of Cyclic 1,3-Diketones with Primary Alcohols", Tetrahedron, vol. 63, 2007, pp. 8492-8498.

Goulas et al.; "Synergistic Effects in Bimetallic Palladium—Copper Catalysts Improve Selectivity in Oxygenate Coupling Reactions", Journal of the American Chemical Society, vol. 138, 2016, pp. 6805-6812.

International Preliminary Report on Patentability received for PCT Application No. PCT/US2015/022086, dated Oct. 6, 2016, 9 pages.

(56) References Cited

OTHER PUBLICATIONS

Non Final Office Action Received for U.S. Appl. No. 14/786,153, dated Feb. 17, 2017, 10 pages.
Non-Final Office Action received for U.S. Appl. No. 14/123,064, dated Jan. 31, 2017, 9 pages.
Notice of Allowance received for U.S. Appl. No. 14/786,153 dated Jun. 9, 2017, 7 pages.
Notice of Allowance received for U.S. Appl. No. 14/123,064, dated Sep. 1, 2017, 8 pages.
Shimizu et al., "Direct C—C Cross-Coupling of Secondary and Primary Alcohols Catalyzed by a γ-Alumina-Supported Silver Subnanocluster", Angew. Chem., vol. 121, 2009, pp. 4042-4046.

METHODS FOR PRODUCING CYCLIC AND ACYCLIC KETONES

CROSS-REFERENCE TO RELATED APPLICATIONS

This application is a U.S. national stage application of PCT/US2015/022086, filed internationally on Mar. 23, 2015, which claims the benefit of U.S. provisional patent application Ser. No. 61/969,761, filed Mar. 24, 2014, the disclosures of which are hereby incorporated by reference in its entirety their entireties.

FIELD

The present disclosure relates generally to the synthesis of cyclic and acyclic ketones suitable for use as fuels and lubricants, and more specifically to the synthesis of cyclic ketones from trimerization of alkyl ketones and synthesis of acyclic ketones from dimerization of alkyl ketones.

BACKGROUND

Transformation of biomass to liquid fuel is desirable to meet the growing demand for transportation fuels in the current diminishing fossil fuel circumstances. One of the main challenges in these transformations includes the selectivity to desired fuels, like gasoline, diesel and jet fuel, in high yields. While processes such as biomass gasification/Fischer-Tropsch and pyrolysis are known in the art, the products derived from such processes have wide distributions. As such, these processes are not selective towards the production of the particular type of fuel. Thus, there exists a need in the art for commercially-viable methods to selectively produce fuels from renewable sources in high yields.

BRIEF SUMMARY

The present disclosure addresses this need in the art by providing methods for producing cyclic and acyclic ketones from materials that can be derived from biomass. Certain cyclic and acyclic ketone products may serve as fuel precursors, that can be hydrodeoxygenated to form cycloalkanes and alkanes suitable for use as fuel, including, for example, jet fuel and diesel. Certain cyclic and acyclic ketone products may also serve as lubricant precursors that can be hydrodeoxygenated to form cycloalkanes and alkanes suitable for use as lubricants.

In one aspect, provided is a method for producing at least one cyclic ketone, by contacting a ketone having a structure of formula (A) with catalyst to produce at least one ketone having a structure of formula (I), (II), (III) or (IV), or any isomers thereof, from at least a portion of the ketone having the structure of formula (A), wherein:
the ketone having the structure of formula (A) is:

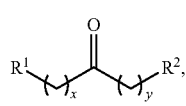

(A)

wherein:
each $R^1$ and $R^2$ is independently H, unsubstituted alkyl, substituted alkyl, —C(R$^t$)$_3$, —CH(R$^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1;
the cyclic ketone having the structure of formula (I) is:

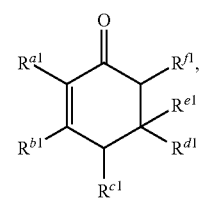

(I)

or any isomers thereof, wherein:
$R^{a1}$ is —(CH$_2$)$_{x-1}$R$^1$;
$R^{b1}$ is —(CH$_2$)$_x$R$^1$;
$R^{c1}$ is —(CH$_2$)$_{y-1}$R$^2$;
$R^{d1}$ is —(CH$_2$)$_x$R$^1$;
$R^{e1}$ is —(CH$_2$)$_y$R$^2$; and
$R^{f1}$ is —(CH$_2$)$_{y-1}$R$^2$;
the cyclic ketone having the structure of formula (II) is:

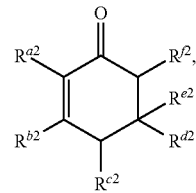

(II)

or any isomers thereof, wherein:
$R^{a2}$ is —(CH$_2$)$_{y-1}$R$^2$;
$R^{b2}$ is —(CH$_2$)$_x$R$^1$;
$R^{c2}$ is —(CH$_2$)$_{y-1}$R$^2$;
$R^{d2}$ is —(CH$_2$)$_x$R$^1$;
$R^{e2}$ is —(CH$_2$)$_y$R$^2$; and
$R^{f2}$ is —(CH$_2$)$_{x-1}$R$^1$;
the cyclic ketone having the structure of formula (III) is:

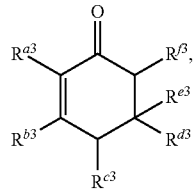

(III)

or any isomers thereof, wherein:
$R^{a3}$ is —(CH$_2$)$_{x-1}$R$^1$;
$R^{b3}$ is —(CH$_2$)$_y$R$^2$;
$R^{c3}$ is —(CH$_2$)$_{x-1}$R$^1$;

$R^{d3}$ is —$(CH_2)_xR^1$;
$R^{e3}$ is —$(CH_2)_yR^2$; and
$R^{f3}$ is —$(CH_2)_{y-1}R^2$;
the cyclic ketone having the structure of formula (IV) is:

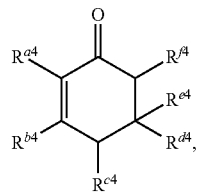

(IV)

or any isomers thereof, wherein:
$R^{a4}$ is —$(CH_2)_{y-1}R^2$;
$R^{b4}$ is —$(CH_2)_yR^2$;
$R^{c4}$ is —$(CH_2)_{x-1}R^1$;
$R^{d4}$ is —$(CH_2)_xR^1$;
$R^{e4}$ is —$(CH_2)_yR^2$; and
$R^{f4}$ is —$(CH_2)_{x-1}R^1$.

The contacting of the ketone having a structure of formula (A) with catalyst may trimerize at least a portion of the ketone having the structure of formula (A) to produce at least one ketone having a structure of formula (I), (II), (III) or (IV), or any isomers thereof.

In some embodiments, the method includes:
contacting a ketone having a structure of formula (A) with catalyst to form a reaction mixture, wherein the contacting of the ketone with the catalyst produces (i) at least one cyclic ketone having a structure of formula (I), (II), (III) or (IV), or any isomers thereof, from at least a portion of the ketone having the structure of formula (A), and (ii) water; and
controlling the amount of water present in the reaction mixture as the at least one cyclic ketone is produced.

In another aspect, provided is a method for producing at least one cyclic ketone, by contacting at least one ketone independently having a structure of formula (A) with catalyst to form a reaction mixture, wherein the contacting of the at least one ketone with the catalyst produces at least one cyclic ketone having a structure of formula (I), (II), (III) or (IV), or any isomers thereof, from at least a portion of the at least one ketone.

Provided is also a method for producing at least one cycloalkane by hydrodeoxygenating at least one ketone having a structure of formula (I), (II), (III) or (IV), or any isomers thereof, produced according to any of the methods described herein to produce at least one cycloalkane.

In another aspect, provided is a method for producing at least one acyclic ketone, by contacting an alcohol having a structure of formula (B) with catalyst to produce at least one acyclic ketone having a structure of formula (L-I) or (L-II), or any isomers thereof, wherein: the catalyst is heterogeneous;
the alcohol having the structure of formula (B) is:

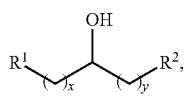

(B)

wherein:
each $R^1$ and $R^2$ is independently H, unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1; and the at least one acyclic ketone having the structure of formula (L-I) or (L-II) is:

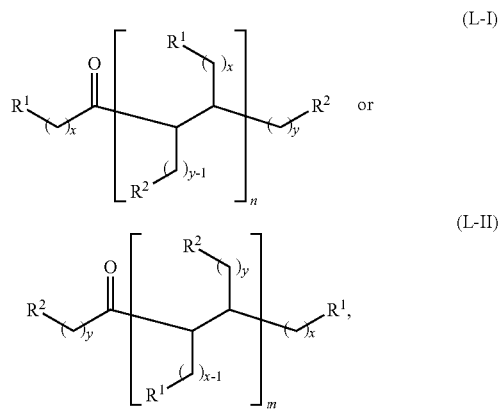

or any isomers thereof, wherein:
$R^1$, $R^2$, x and y are as defined for formula (B), and
n and m are each an integer greater than or equal to 1.

Provided is a method for producing at least one acyclic ketone, by contacting at least one alcohol independently having a structure of formula (B) with catalyst to produce at least one acyclic ketone having a structure of formula (L-I) or (L-II), or any isomers thereof, wherein the catalyst is heterogeneous.

In yet another aspect, provided is a method for producing at least one acyclic ketone, by contacting a ketone having a structure of formula (A) with catalyst in the presence of a hydrogen source, such as $H_2$ or a secondary alcohol, to produce at least one acyclic ketone having a structure of formula (L-I) or (L-II), or any isomers thereof, wherein:
the catalyst is heterogeneous;
the ketone having the structure of formula (A) is:

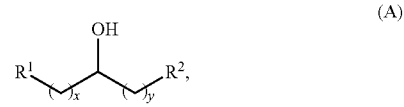

(A)

wherein:
$R^1$ is H, unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
$R^2$ is unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, each R' is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;

x is an integer greater than or equal to 1;

y is an integer greater than or equal to 0; and the at least one acyclic ketone having the structure of formula (L-I) or (L-II) is:

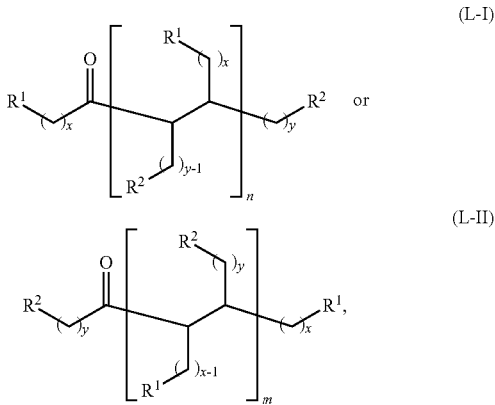

or any isomers thereof, wherein:

$R^1$, $R^2$, x and y are as defined for formula (A), provided that when y is 0, $R^2$ is H for formula (L-I), and n and m are each an integer greater than or equal to 1.

In some embodiments, the catalyst is a heterogeneous metal catalyst.

In yet another aspect, provided is a method for producing at least one acyclic ketone, by contacting at least one ketone independently having a structure of formula (A) with catalyst in the presence of a hydrogen source, such as $H_2$ or a secondary alcohol, to produce at least one acyclic ketone having a structure of formula (L-I) or (L-II), or any isomers thereof.

Provided is also a method for producing at least one alkane by hydrodeoxygenating at least one acyclic ketone having a structure of formula (L-I) or (L-II), or any isomers thereof, produced according to any of the methods described herein to produce at least one alkane.

In yet another aspect, provided is a composition comprising a ketone having the structure of formula (A) as described herein; and catalyst. In certain embodiments, the composition further includes a hydrogen source. Provided is also a composition comprising an alcohol having a structure of formula (B) as described herein; catalyst, wherein the catalyst is heterogeneous.

Provided is also a cyclic ketone having a structure of formula (I), (II), (III) or (IV) produced according to any of the methods described herein, suitable for use as jet fuel, diesel or lubricant, or precursors thereof. Provided is also an acyclic ketone having a structure of formula (L-I) or (L-II) produced according to any of the methods described herein, suitable for use as jet fuel or lubricant, or precursors thereof.

DESCRIPTION OF THE FIGURES

The present disclosure can be best understood by references to the following description taken in conjunction with the accompanying figures.

DETAILED DESCRIPTION

Figure 1A:
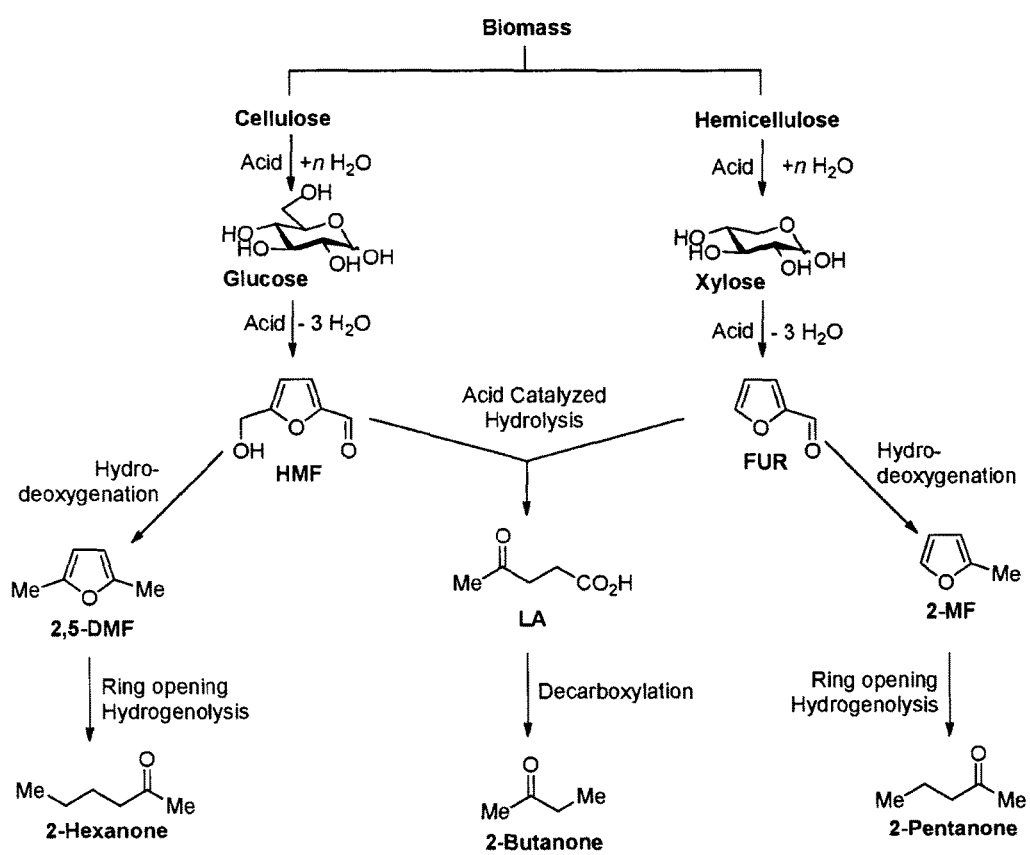
FIG. 1A depicts exemplary chemical pathways to produce alkyl methyl ketones that may be used in the methods described herein.

The following description sets forth numerous exemplary configurations, processes, parameters, and the like. It should be recognized, however, that such description is not intended as a limitation on the scope of the present disclosure, but is instead provided as a description of exemplary embodiments.

Provided herein are methods for producing cyclic and acyclic ketones from the oligomerization of alkyl ketones. Under certain conditions, the alkyl ketones can trimerize to produce the cyclic ketones, or the alkyl ketones can dimerize to produce acyclic ketones. The alkyl ketones used may also undergo trimer aromatization and other oligomerization reactions (e.g., tetramerization); however, the catalysts and the reaction conditions selected can drive the reaction to favor trimerization and/or dimerization.

In one aspect, provided are methods for producing at least one cyclic ketone, by contacting a ketone having a structure of formula (A) with catalyst to produce at least one cyclic ketone having a structure of formula (I), (II), (III) or (IV), or any isomers thereof.

In another aspect, provided are methods for producing at least one acyclic ketone, by contacting a ketone having a structure of formula (A) with catalyst in the presence of a hydrogen source, such as $H_2$ or a secondary alcohol, to produce at least one acyclic ketone having a structure of formula (L-I) or (L-II), or any isomers thereof.

In yet another aspect, provided are methods for producing at least one acyclic ketone, by contacting an alcohol having a structure of formula (B) with catalyst to produce at least one acyclic ketone having a structure of formula (L-I) or (L-II), or any isomers thereof.

In yet other aspects, provided are methods for producing at least one acyclic ketone, by contacting a ketone having a structure of formula (A) and an alcohol having a structure of formula (B) with catalyst to produce a mixture of acyclic ketones, including at least one acyclic ketone having a structure of formula (L-I) or (L-II), or any isomers thereof.

The ketones having a structure of formula (A), the alcohols having a structure of formula (B), the cyclic ketones having the structure of formula (I), (II), (III) or (IV), and the acyclic ketones having the structure of formula (L-I) or (L-II), as well as the catalyst and the reaction conditions are described in further detail below.

Formation of Cyclic Ketones

The alkyl ketones described herein can oligomerize and cyclize in the presence of the catalysts described herein. Under certain conditions, the alkyl ketones can trimerize to form cyclic ketone products.

Alkyl Ketones

Alkyl ketones used in the methods described herein have at least one methylene group in the alpha position (i.e., relative to the carbonyl group). For example, the alkyl ketones used to produce cyclic ketones may have a structure of formula (A):

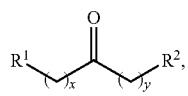

(A)

wherein:
each $R^1$ and $R^2$ is independently H, unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted carbocyclyl, substituted carbocyclyl, unsubstituted heterocyclyl, or substituted heterocyclyl,
  wherein each $R^t$ is independently unsubstituted aliphatic, substituted aliphatic, unsubstituted aryl, substituted aryl, unsubstituted heteroaryl, substituted heteroaryl, unsubstituted carbocyclyl, substituted carbocyclyl, unsubstituted heterocyclyl, or substituted heterocyclyl;
each x and y is independently an integer greater than or equal to 1.

In some embodiments of the ketone having a structure of formula (A), when x and y are both 1, either $R^1$ or $R^2$ is other than H. In certain embodiments of the ketone having a structure of formula (A), when x and y are both at least 1, $R^1$ is unsubstituted alkyl, and $R^2$ is H. In one embodiment, the ketone having the structure of formula (A) is other than acetone.

In certain embodiments of the ketone having a structure of formula (A),
  $R^1$ is unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted carbocyclyl, substituted carbocyclyl, unsubstituted heterocyclyl, or substituted heterocyclyl;
  $R^2$ is H, unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted carbocyclyl, substituted carbocyclyl, unsubstituted heterocyclyl, or substituted heterocyclyl; and
  each x and y is independently an integer greater than or equal to 1.

In some embodiments, the ketone having the structure of formula (A) used to produce cyclic ketones is a ketone having the structure of formula (A-1):

(A-1)

wherein x is an integer greater than or equal to 2.

In some embodiments of the ketone having the structure of formula (A) or (A-1), $R^1$ is unsubstituted or substituted alkyl. In certain embodiments, $R^1$ is unsubstituted alkyl. For example, $R^1$ may be methyl, ethyl, propyl, butyl, pentyl, hexyl, heptyl, octyl, nonyl, or decyl. In one embodiment, $R^1$ is methyl. In certain embodiments, $R^1$ is alkyl substituted with unsubstituted aryl, substituted aryl, unsubstituted heteroaryl, or substituted heteroaryl. In one embodiment, $R^1$ is alkyl substituted with unsubstituted or substituted furan, or unsubstituted or substituted phenyl.

In some embodiments of the ketone having the structure of formula (A) or (A-1), $R^2$ is unsubstituted or substituted alkyl. In certain embodiments, $R^2$ is unsubstituted alkyl. For example, $R^2$ may be methyl, ethyl, propyl, butyl, pentyl, hexyl, heptyl, octyl, nonyl, or decyl.

In one embodiment of the ketone having the structure of formula (A) or (A-1), $R^2$ is methyl. It should be understood that when $R^2$ is methyl, the ketone having the structure of formula (A) or (A-1) is a methyl ketone. In another embodiment, $R^1$ is unsubstituted or substituted alkyl, and $R^2$ is methyl. It should be understood that when $R^1$ is unsubstituted or substituted alkyl, and $R^2$ is methyl, the ketone having the structure of formula (A) or (A-1) is an alkyl methyl ketone. In certain embodiments of the ketone having the structure of formula (A) or (A-1), when $R^1$ or $R^2$ is alkyl, the alkyl may be unbranched or branched. In one embodiment, the alkyl is branched.

In some embodiments that can be combined with any of the foregoing embodiments of the ketone having a structure of formula (A) or (A-1), x is 3 to 45. In certain embodiments, x is 3 to 21. In one embodiment, x is 3, 5, 7 or 9.

Examples of alkyl ketones that may be used in the methods described herein include:

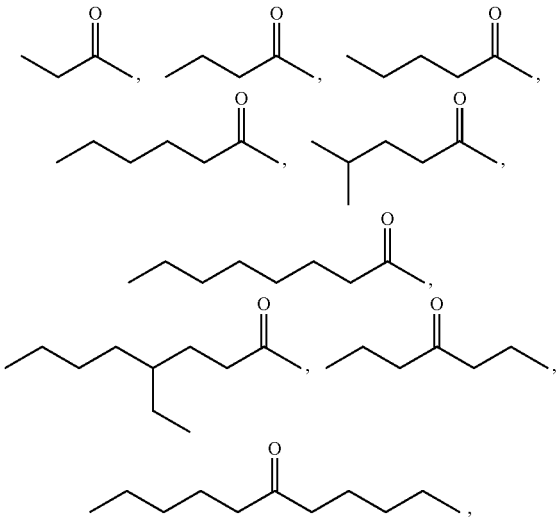

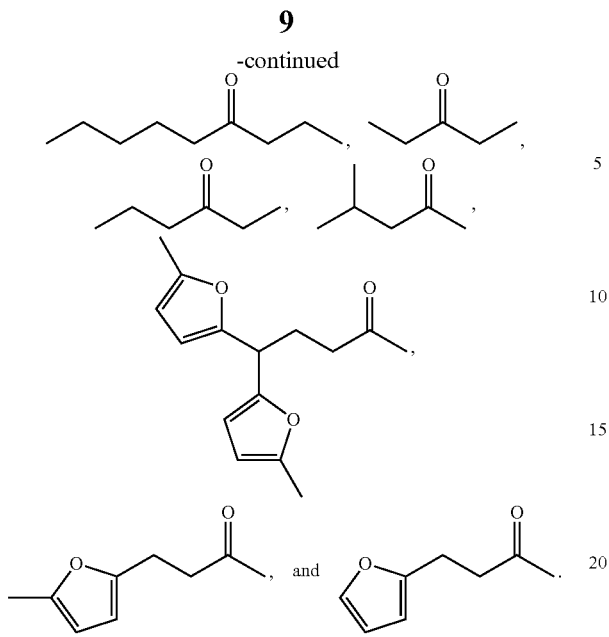

The alkyl ketones may be used to produce cyclic ketones suitable for use as jet fuels, diesel and/or lubricants, or precursors thereof. For example, when the alkyl ketones are used to produce jet fuels and diesel, or precursors thereof, the ketones having the structure of formula (A) may, for example, have between 4 and 8 carbon atoms in total. In one embodiment, the ketone of formula (A) has 5 carbon atoms in total. In certain embodiments, the ketone having the structure of formula (A) may, for example, have a chain length of 4 and 8 carbon atoms. In certain embodiments, x is 1 in the ketone of formula (A). In certain embodiments, $R^1$ and $R^2$ may be linear alkyl groups (e.g., methyl). Examples of alkyl ketones suitable for use in producing jet fuels may include:

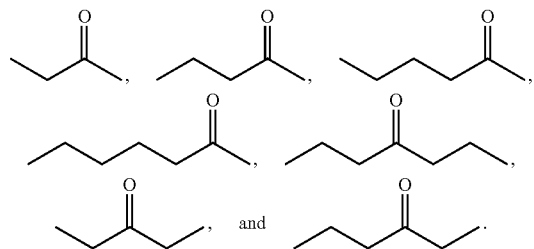

When the alkyl ketones are used to produce lubricants, the ketone having the structure of formula (A) may, for example, have between 8 and 24 carbon atoms in total. In certain embodiments, the ketones of formula (A) may, for example, have a chain length of 7 to 20 carbon atoms. In certain embodiments, $R^1$ and $R^2$ may be linear alkyl groups, branched alkyl groups or alkyl groups substituted with heteroaryl. Examples of alkyl ketones suitable for use in producing lubricants may include:

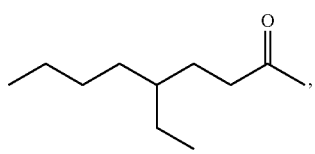

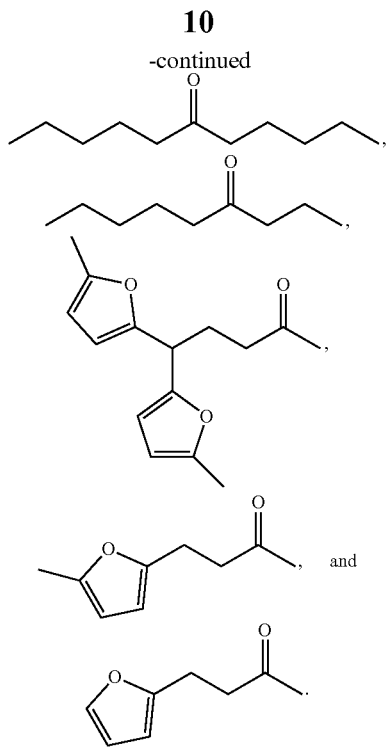

Mixture of Alkyl Ketones

It should be understood that, in some embodiments, one ketone having a structure of formula (A), as described above may be used. Such ketone can undergo self-condensation to produce the cyclic ketones described herein. In other embodiments, however, a mixture of ketones independently having the structure of formula (A) may be used. Such mixture of ketones can undergo cross-condensations to produce a mixture of cyclic ketones. Thus, provided herein is also a method for producing a cyclic ketone or a mixture of cyclic ketones, by contacting two or more ketones independently having a structure of formula (A) with catalyst to produce at least one cyclic ketone having a structure of formula (I), (II), (III) or (IV), or any isomers thereof, from at least a portion of the mixture of ketones independently having the structure of formula (A).

For example, in one exemplary embodiment, the method includes contacting 2-hexanone and 2-pentanone with catalyst to produce a mixture of $C_{15}$ cyclic ketone, $C_{16}$ cyclic ketone, $C_{17}$ cyclic ketone, and $C_{18}$ cyclic ketone. In another exemplary embodiment, the method includes contacting 2-hexanone, 2-pentanone, and 2-butanone with catalyst to produce a mixture of $C_{12}$ cyclic ketone, $C_{13}$ cyclic ketone, $C_{14}$ cyclic ketone, $C_{15}$ cyclic ketone, $C_{16}$ cyclic ketone, $C_{17}$ cyclic ketone, and $C_{18}$ cyclic ketone.

Source of Alkyl Ketones

Figure 1B:
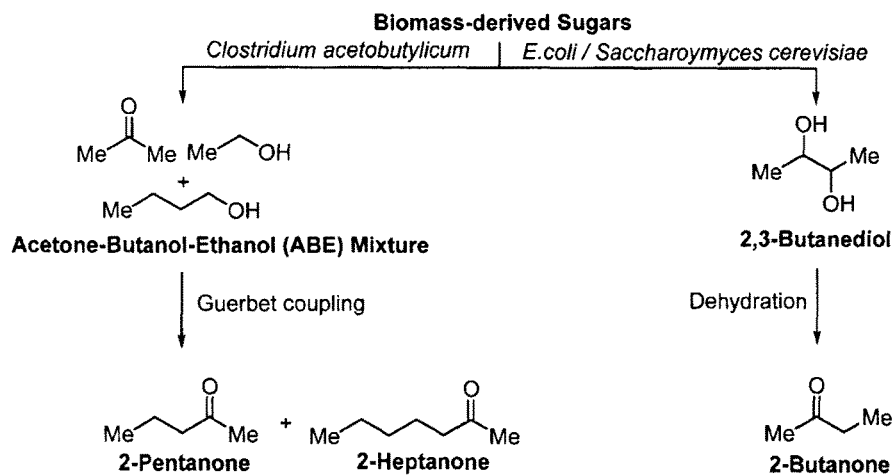
FIG. 1B depicts exemplary biochemical pathways to produce alkyl methyl ketones that may be used in the methods described herein.

The alkyl ketones used herein can be obtained from any commercially available sources, or be prepared using any methods currently known in the art. For example, the alkyl ketones may be obtained from biomass. FIGS. 1A and 1B depict several exemplary pathways known in the art to produce alkyl methyl ketones.

For example, with reference to FIG. 1A, biomass-derived hexose and pentose sugars may be dehydrated to yield 5-hydroxymethylfurfural (5-HMF) and furfural (FUR) respectively by acid catalysis. Partial oxygen removal of 5-HMF and FUR through hydrodeoxygenation can yield 2,5-dimethylfuran (2,5-DMF) and 2-methylfuran (2-MF)

respectively. See e.g., Roman-Leshkov, Y., et al., *Nature* 2007, 447 (7147), 982-U5; Chidambaram, M. & Bell, A. T., *Green Chem.* 2010, 12 (7), 1253-1262; Zeitsch, K. J., Ed. Elsevier Science: 2000; Vol. 13, pp 229-230. Further, the subsequent hydrogenolysis of 2,5-DMF and 2-MF is known in the art to selectively produce the linear alkyl methyl ketones, such as 2-hexanone and 2-pentanone. See e.g., Corma, A., et al., *Energy & Environmental Science* 2012, 5 (4), 6328-6344.

Thus, in one exemplary embodiment, provided is a method for producing at least one cyclic ketone as described herein, by: a) converting 2,5-dimethylfuran into 2-hexanone; and b) contacting the 2-hexanone with catalyst to produce at least one cyclic ketone as described herein. The 2,5-dimethylfuran may, for example, be produced from 5-hydroxymethylfurfural, which may be obtained from glucose. It is known in the art that glucose can be derived from cellulosic component of biomass.

Another exemplary method to produce ketones suitable for use in the methods described herein involves the acid-catalyzed hydrolysis of cellulosic feed stocks at elevated temperatures to yield levulinic acid (LA). Similarly, the hemicellulose component of the biomass may also be converted into LA. See e.g., Rackemann, D. W. & Doherty, W. O. S., *Biofuels, Bioproducts and Biorefining* 2011, 5 (2), 198-214; Upare, P. P., et al., *Green Chem.* 2013, 15 (10), 2935-2943. LA can then be converted into an alkyl methyl ketone, such as 2-butanone. Specifically, the decarboxylation of LA over a catalyst, such as CuO, can yield 2-butanone. See Gong, Y., et al., *Molecules* 2010, 15 (11), 7946-7960.

Thus, in another exemplary embodiment, provided is a method for producing at least one cyclic ketone as described herein, by: converting levulinic acid into 2-butanone; and b) contacting the 2-butanone with catalyst to produce at least one cyclic ketone. The levulinic acid may, for example, be produced from 5-hydroxymethylfurfural and/or furfural. The 5-hydroxymethylfurfural may be obtained from glucose. The furfural may be obtained from xylose. It is known in the art that glucose can be derived from cellulosic component of biomass, and xylose can be obtained from the hemicellulosic component of biomass.

In yet another example, with reference to FIG. 1B, biochemical processes can produce ketones that can be used in the methods described herein. For example, *Clostridium acetobutylicum* can produce acetone, n-butanol and ethanol (ABE) from sugars in 3:6:1 ratio, respectively. See e.g., Tracy, B. P., et al., *Curr. Opin. Biotechnol.* 2012, 23 (3), 364-381; Alsaker, K. V., et al., *Biotechnol. Bioeng.* 2010, 105 (6), 1131-1147. ABE may undergo a coupling reaction using, for example, Guerbet reaction conditions to produce 2-pentanone and 2-heptanone. See Anbarasan, P., et al., *Nature* 2012, 491 (7423), 235-239.

Thus, provided herein is also a method for producing at least one cyclic ketone, by: a) contacting acetone and two or more alcohols with catalyst to produce a mixture of ketones independently having the structure of formula (A) as described herein; b) isolating at least one of the ketones produced in step (a); and c) contacting one or more of the isolated ketones with additional catalyst to produce at least one cyclic ketone having a structure of formula (I), (II), (III) or (IV), or any isomers thereof, as described herein, from at least a portion of the one of more of the isolated ketones.

In some embodiments of the method described above, the catalyst used to produce the mixture of ketones and the additional catalyst used to convert the mixture of ketones into cyclic ketones may be the same or different. For example, a catalyst comprising hydrotalcite (including, for example, calcined hydrotalcite) may be used for both reactions.

It should be understood that, in other exemplary embodiments, the method described above may also be performed without isolating the mixture of ketones in step (b). Thus, provided is also a method for producing at least one cyclic ketone, by: a) contacting acetone and two or more alcohols with catalyst to produce a mixture of ketones independently having the structure of formula (A) as described herein; and b) contacting one of more of the ketones produced in step (a) with additional catalyst to produce at least one cyclic ketone having a structure of formula (I), (II), (III) or (IV), or any isomers thereof, as described herein, from at least a portion of the mixture of ketones independently having the structure of formula (A).

In some embodiments of the method described above, the two or more alcohols may be butanol and ethanol. Thus, in one exemplary embodiment, the method includes: a) contacting acetone, butanol and ethanol with catalyst to produce a mixture of ketones selected from the group consisting of 2-pentanone, 4-heptanone, 2-heptanone, 4-nonanone, 2-methyl-4-nonanone, and 6-undecanone; b) isolating at least one of the ketones from the mixture of ketones produced in step (a); and c) contacting at least one of the isolated ketones from step (b) with additional catalyst to produce at least one cyclic ketone from at least a portion of the isolated ketones. The acetone, butanol and ethanol may, for example, be produced by fermentation of biomass or sugars.

In yet another example, provided herein is also a method for producing at least one cyclic ketone, by: a) contacting two or more alcohols with catalyst to produce a mixture of ketones independently having the structure of formula (A) as described herein; b) isolating at least one of the ketones produced in step (a); and c) contacting at least one of the ketones isolated in step (b) with additional catalyst to produce at least one cyclic ketone having a structure of formula (I), (II), (III) or (IV), or any isomers thereof, as described herein, from at least a portion of the isolated ketones. In some embodiments of this method, at least one of the two or more alcohols is a secondary alcohol. Suitable secondary alcohols may include, for example, isopropanol, 2-butanol, 2-pentanol, 2-hexanol, 2-heptanol, 2-octanol, 2-nonanol, 2-decanol, 2-undecanol, 2-dodecanol, 2-tridecanol, 2-tetradecanol, 2-pentadecanol, 2-hexadecanol, 2-heptadecanol, 2-octadecanol, 2-nonadecanol, 2-icosanol, 2,3-butanediol, and acetoin.

In some embodiments of the method described above, the catalyst used to produce the mixture of ketones and the additional catalyst used to convert the mixture of ketones into cyclic ketones may be the same or different. For example, a catalyst comprising hydrotalcite (including, for example, calcined hydrotalcite) may be used for both reactions.

It should be understood that, in other exemplary embodiments, the method described above may also be performed without isolating the mixture of ketones in step (b). Thus, provided is also a method for producing at least one cyclic ketone, by: a) contacting two or more alcohols with catalyst to produce a mixture of ketones independently having the structure of formula (A) as described herein; and b) contacting one of more of the ketones produced in step (a) with additional catalyst to produce at least one cyclic ketone having a structure of formula (I), (II), (III) or (IV), or any isomers thereof, as described herein, from at least a portion of the mixture of ketones.

In some embodiments of the method described above, the two or more alcohols may be isopropanol, butanol and ethanol. Thus, in one exemplary embodiment, the method includes: a) contacting isopropanol, butanol and ethanol with catalyst to produce a mixture of ketones selected from the group consisting of 3-octanone, 3-pentanone and 6-ethyldecan-3-one; b) isolating at least one of the ketones from the mixture of ketones produced in step (a); and c) contacting at least one of the isolated ketones from step (b) with additional catalyst to produce a mixture of cyclic ketones. The isopropanol, butanol and ethanol may, for example, be produced by fermentation of biomass or sugars.

With reference again to FIG. 1B, *Saccharomyces cerevisiae* may also be engineered to produce 2,3-butanediol (2,3-BDO) by feeding the biomass-derived sugars. See Kim, S.-J., et al., *Bioresour. Technol.* 2013, 146 (0), 274-281. Then, an acid-catalyzed selective dehydration of 2,3-BDO may be employed to synthesize 2-butanone. See Zhang, W., et al., *Green Chem.* 2012, 14 (12), 3441-3450.

Thus, provided herein is also a method for producing at least one cyclic ketone as described herein, by: a) converting 2,3-butanediol into 2-butanone; and b) contacting 2-butanone with catalyst to produce at least one cyclic ketone as described herein.

Figure 1C:
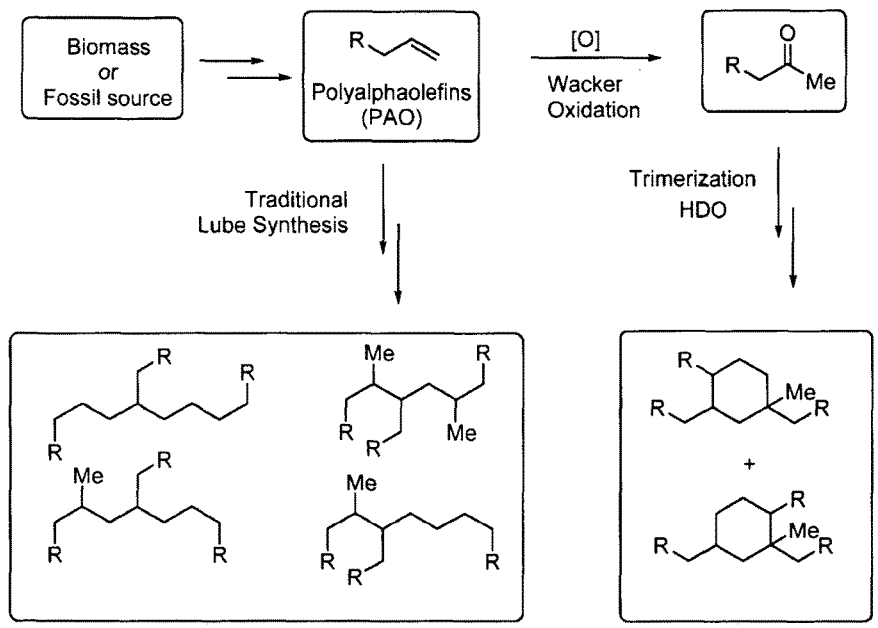
FIG. 1C depicts exemplary pathways to produce alkyl ketones from polyalphaolefins (PAOs).

In yet another example, with reference to FIG. 1C, alkyl ketones suitable for use in the methods described herein may be produced from ethanol. For example, polyalphaolefins (PAOs) may be derived from ethanol, and such PAOs may subsequently undergo Wacker oxidation to produce the alkyl ketones.

Cyclic Ketone Products

Cyclic ketones produced according to the methods described herein are compounds in which carbon atoms are connected to form a ring structure, wherein at least one carbonyl group (C=O) is bonded to two of the ring carbon atoms. The cyclic ketones produced may, for example, have a structure of formula (I), (II), (III) or (IV). The cyclic ketone having the structure of formula (I) is:

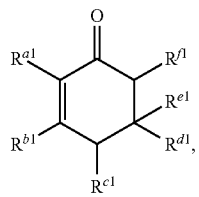

(I)

or any isomers thereof, wherein:
$R^{a1}$ is —$(CH_2)_{x-1}R^1$;
$R^{b1}$ is —$(CH_2)_x R^1$;
$R^{c1}$ is —$(CH_2)_{y-1}R^2$;
$R^{d1}$ is —$(CH_2)_x R^1$;
$R^{e1}$ is —$(CH_2)_y R^2$; and
$R^{f1}$ is —$(CH_2)_{y-1}R^2$;
wherein $R^1$, $R^2$, x and y are as defined for formula (A).

The cyclic ketone having the structure of formula (II) is:

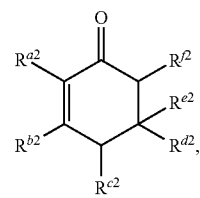

(II)

or any isomers thereof, wherein:
$R^{a2}$ is —$(CH_2)_{y-1}R^2$;
$R^{b2}$ is —$(CH_2)_x R^1$;
$R^{c2}$ is —$(CH_2)_{y-1}R^2$;
$R^{d2}$ is —$(CH_2)_x R^1$;
$R^{e2}$ is —$(CH_2)_y R^2$; and
$R^{f2}$ is —$(CH_2)_{x-1}R^1$;
wherein $R^1$, $R^2$, x and y are as defined for formula (A).

The cyclic ketone having the structure of formula (III) is:

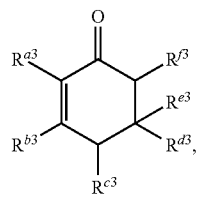

(III)

or any isomers thereof, wherein:
$R^{a3}$ is —$(CH_2)_{x-1}R^1$;
$R^{b3}$ is —$(CH_2)_y R^2$;
$R^{c3}$ is —$(CH_2)_{x-1}R^1$;
$R^{d3}$ is —$(CH_2)_x R^1$;
$R^{e3}$ is —$(CH_2)_y R^2$; and
$R^{f3}$ is —$(CH_2)_{y-1}R^2$;
wherein $R^1$, $R^2$, x and y are as defined for formula (A).

The cyclic ketone having the structure of formula (IV) is:

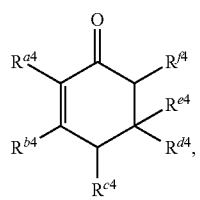

(IV)

or any isomers thereof, wherein:
$R^{a4}$ is —$(CH_2)_{y-1}R^2$;
$R^{b4}$ is —$(CH_2)_y R^2$;
$R^{c4}$ is —$(CH_2)_{x-1}R^1$;
$R^{d4}$ is —$(CH_2)_x R^1$;
$R^{e4}$ is —$(CH_2)_y R^2$; and
$R^{f4}$ is —$(CH_2)_{x-1}R^1$,
wherein $R^1$, $R^2$, x and y are as defined for formula (A).

It should be understood that isomers of the cyclic ketones of formula (I), (II), (III) and (IV) may be produced. Isomers of such cyclic ketones may include stereoisomers.

It should be understood by one of skill in the art that the structure of the cyclic ketones of formula (I), (II), (III) and (IV) will correspond to the structure of the ketone(s) of formula (A) used. Table A below provides examples of cyclic ketones having the structure of formula (I), (II), (III) and (IV) that may be produced from a ketone of formula (A).

TABLE A

| Ketone Reactant | Cyclic Ketone Products |
|---|---|
| $R^1$ = unsubstituted or substituted alkyl<br>Examples:<br>methyl, ethyl, n-propyl, iso-propyl, n-butyl, iso-butyl, n-pentyl, n-hexyl, 2-ethylhexyl, [structures shown including methylfuran-based compounds] | [Four cyclic ketone structures with $R^1$ substituents]<br>or any isomers or mixtures thereof |
| each $R^1$ and $R^2$ = unsubstituted or substituted alkyl<br>Examples:<br>$R^1 = R^2$ = methyl, ethyl, n-butyl;<br>$R^1$ = ethyl, $R^2$ = methyl; and<br>$R^1$ = butyl, $R^2$ = ethyl | [Four cyclic ketone structures with $R^1$ and $R^2$ substituents]<br>or any isomers or mixtures thereof |

It should be understood by one of skill in the art that when two or more alkyl ketones are used, a mixture of cyclic ketones may be produced. Table B below provides examples of cyclic ketones having the structure of formula (I), (II), (III) and (IV) that may be produced from a mixture of ketones of formula (A).

TABLE B

| Alkyl Ketone | Cyclic Ketones |
|---|---|
| [2-butanone structure]<br>and<br>[2-hexanone structure] | [Four cyclic ketone product structures]<br>or any isomers or mixtures thereof |

TABLE B-continued

| Alkyl Ketone | Cyclic Ketones |
|---|---|
| 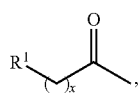 and 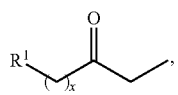 | 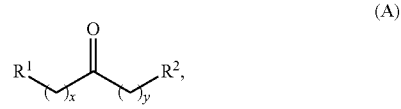 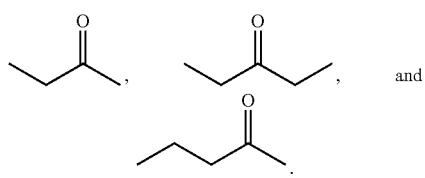 | or any isomers or mixtures thereof

In some embodiments of the method described herein to produce the cyclic ketones, at least 50%, at least 60%, at least 70%/0, at least 80%, at least 85%, at least 90%, at least 95%, at least 96%, at least 97%, at least 98%, or at least 99% of the products in the reaction mixture are the cyclic ketones of formula (I), (II), (III) and/or (IV), or any isomers thereof. Various factors may cause the reaction to favor trimerization to form cyclic ketones over other competing reactions (e.g., dimerization, tetramerization or other oligomerization reactions), as well as to favor the formation of certain cyclic ketones. Factors that allow the tuning of the reaction may include, for example, the choice of starting materials and the amount of water in the reaction mixture.

Choice of Alkyl Ketones

In some embodiments, the cyclic ketones of formula (I), (II), (III) and/or (IV), or any isomers thereof, are produced when methyl ketones are used. Thus, the use of methyl ketones may favor trimerization to form cyclic ketones over dimerization to form acyclic ketones and other forms of oligomerization. For example, methyl ketones suitable for use in producing cyclic ketones of formula (I), (II), (III) and/or (IV), or any isomers thereof, include ketones having the structure of formula (A-1):

$$R^1 \underset{x}{\underbrace{\qquad}} \underset{O}{\overset{\displaystyle\|}{C}} \qquad \text{(A-1)}$$

wherein $R^1$ is as described herein for formula (A) and (A-1) herein, and x is an integer greater than or equal to 2.

In other embodiments, the ketone is an ethyl ketone having the structure of formula (A-2):

$$R^1 \underset{x}{\underbrace{\qquad}} \underset{O}{\overset{\displaystyle\|}{C}} \qquad \text{(A-2)}$$

wherein $R^1$ is as described herein for formula (A) and (A-1) herein, and x is an integer greater than or equal to 2.

In other embodiments, the cyclic ketones of formula (I), (II), (III) and/or (IV), or any isomers thereof, are produced when the ketone having the structure of formula (A) is:

$$R^1 \underset{x}{\underbrace{\qquad}} \underset{O}{\overset{\displaystyle\|}{C}} \underset{y}{\underbrace{\qquad}} R^2, \qquad \text{(A)}$$

wherein the total chain length of the ketone is less than six carbon atoms, and $R^1$, $R^2$, x and y are as described herein for formula (A). For example, examples of ketones of formula (A) having a chain length less than six carbon atoms may include:

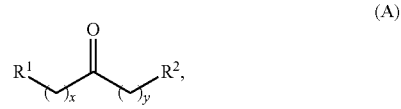

In yet other embodiments, the cyclic ketones of formula (I), (II), (III) and/or (IV), or any isomers thereof, are produced when the ketone having the structure of formula (A) is:

$$R^1 \underset{x}{\underbrace{\qquad}} \underset{O}{\overset{\displaystyle\|}{C}} \underset{y}{\underbrace{\qquad}} R^2, \qquad \text{(A)}$$

wherein x and y are each 1, and $R^1$ and $R^2$ is as defined herein for formula (A). When x and y are each 1, the ketone has no branching at the alpha position (i.e., relative to the carbonyl group). In certain embodiments, each $R^1$ and $R^2$ is independently alkyl. In certain embodiments, each $R^1$ and $R^2$ is independently is unsubstituted alkyl. For example, each $R^1$ and $R^2$ is independently methyl, ethyl, propyl, butyl, pentyl, hexyl, heptyl, octyl, nonyl, or decyl. In one embodiment, each $R^1$ and $R^2$ is independently methyl. In certain embodiments, one or both of $R^1$ and $R^2$ is independently unsubstituted alkyl, or alkyl substituted with unsubstituted aryl, substituted aryl, unsubstituted heteroaryl, or substituted heteroaryl. In one embodiment, one or both of $R^1$ and $R^2$ is independently unsubstituted alkyl, or alkyl substituted with unsubstituted or substituted furan, or unsubstituted or substituted phenyl.

Choice of Catalysts

In some embodiments, the use of certain catalysts may favor trimerization to form cyclic ketones over dimerization to form acyclic ketones and other forms of oligomerization. For example, in certain embodiments when ketones having the structure of formula (A) is:

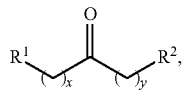

(A)

wherein the total chain length of the ketone is less than 6 carbon atoms, and $R^1$, $R^2$, x and y are as described herein for formula (A), are used, the use of non-transition metal-supported catalysts as described herein may favor trimerization to form cyclic ketones over dimerization to form acyclic ketones and other forms of oligomerization. Examples of such non-transition metal supported catalysts may include $SiO_2$—$Al_2O_3$, hydrotalcite, MgO, NaOH, KOH, and CaO.

In other embodiments, the cyclic ketones of formula (I), (II), (III) and/or (IV), or any isomers thereof, are produced when any of the catalysts described herein are used. For example, in certain embodiments when ketones having the structure of formula (A-1) is:

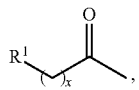

(A-1)

wherein $R^1$ is as described herein for formula (A) and (A-1), and x is an integer greater than or equal to 2, are used, any catalysts described herein may be used to produce the corresponding cyclic ketones.

In certain embodiments, the cyclic ketones of formula (I), (II), (III) and/or (IV), or any isomers thereof, are produced when basic catalysts are used with ketones having the structure of formula (A-1) is:

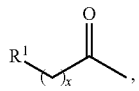

(A-1)

wherein the total chain length of the ketone is between 4 and 15 carbon atoms, or between 5 and 15 carbon atoms, and $R^1$ and x are as described herein for formula (A) and (A-1).

In certain embodiments, the cyclic ketones of formula (I), (II), (III) and/or (IV), or any isomers thereof, are produced when basic catalysts are used with ketones having the structure of formula (A-2) is:

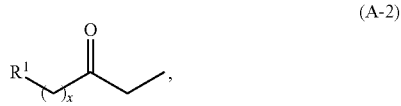

(A-2)

wherein $R^1$ is as described herein for formula (A) and (A-1) herein, and x is an integer greater than or equal to 2.

Amount of Water in Reaction

The amount of water present in the reaction mixture may, in certain instances, cause trimerization to form cyclic ketones to be favored over dimerization to form acyclic ketones and other competing reactions (e.g., tetramerization). In some embodiments where basic catalyst is used, the amount of water present in the reaction mixture is less than 10 wt %, less than 5 wt %, less than 4 wt %, less than 3 wt %, less than 2 wt %, less than 1.5 wt %, less than 1 wt %, less than 0.9 wt %, less than 0.8 wt %, less than 0.7 wt/o, less than 0.6 wt %, less than 0.5 wt %, less than 0.4 wt %, less than 0.3 wt %, less than 0.2 wt %, or less than 0.1 wt %.

The amount of water in the reaction mixture can be controlled using any suitable methods or techniques known in the art. For example, the choice of catalysts can affect the water content in the reaction. For example, the use of calcined hydrotalcite may be used to produce the cyclic ketones described above.

The water content of the reaction may also be controlled by distillation (e.g., using a Dean-Stark apparatus) to remove water during the reaction. Thus, in one variation, provided is method for producing at least one cyclic ketone, by: contacting a ketone having a structure of formula (A) with catalyst to produce at least one cyclic ketone having a structure of formula (I), (II), (III) or (IV), or any isomers thereof, and water in a reaction mixture; and removing at least a portion of the water in the reaction mixture, wherein the amount of water in the reaction mixture is less than 1 wt %, less than 0.9 wt %, less than 0.8 wt %, less than 0.7 wt %, less than 0.6 wt %, less than 0.5 wt %, less than 0.4 wt %, less than 0.3 wt %, less than 0.2 wt %, or less than 0.1 wt % of water.

The water content of the reaction may also be controlled by the use of absorbents. Suitable absorbents may include, for example, molecular sieves, fused calcium salts and zeolites. Thus, in another variation, provided is method for producing at least one cyclic ketone, by: contacting a ketone having a structure of formula (A) with catalyst and an absorbent to produce at least one cyclic ketone having a structure of formula (I), (II), (III) or (IV), or any isomers thereof.

Other suitable methods to control the amount of water in the reaction mixture involve the use of a biphasic reaction system.

Figure 2:
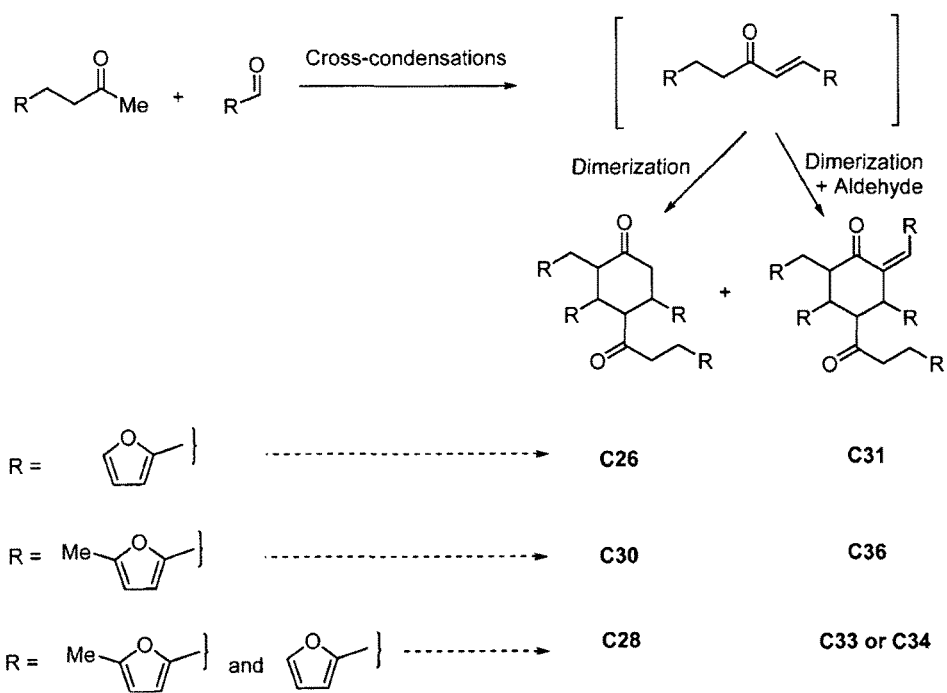
FIG. 2 depicts an exemplary reaction scheme involving the cross-condensation of an aldehyde and an alkyl methyl ketone as described herein.

Formation of Cyclic Ketones from Cross-Condensation of Alkyl Ketones with Aldehydes In another aspect, provided is also a method includes contacting a ketone having the structure of formula (A) with an aldehyde to produce cyclic ketones. An exemplary reaction scheme involving cross-condensation of an aldehyde and a methyl ketone is depicted in FIG. 2.

Provided is also a method for producing a cyclic ketone or a mixture of cyclic ketones, by contacting a ketone having a structure of formula (A) with an aldehyde of formula (C) to produce a cyclic ketone having a structure of formula (M-I) or (M-II), or to produce a mixture of cyclic ketones having a structure of formula (M-I) and (M-II).

The ketone used in this method may be a methyl alkyl ketone having the structure of formula (A-1):

(A-1)

wherein $R^1$ and x are defined for formula (A) above.
The aldehyde may have the structure of formula (C):

(C)

wherein $R^3$ is H, unsubstituted alkyl, substituted alkyl, —C($R^t$)$_3$, —CH($R^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl.

The cyclic ketones produced may have the structure of formula (M-I) or (M-II):

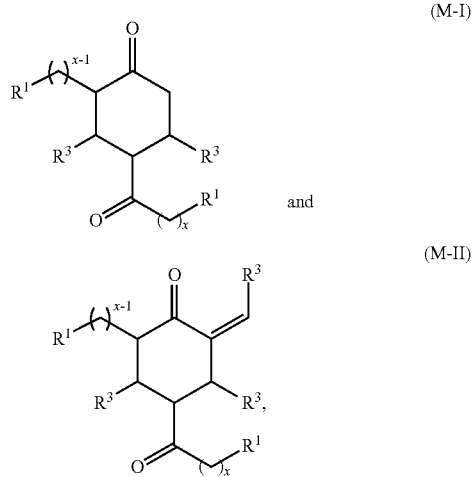

or any isomers thereof, wherein $R^1$ and x are as defined for formula (A-1) above, and $R^3$ is as defined for formula (C) above.

In some embodiments of this method, $R^1$ of the ketone having the structure of formula (A) or (A-1) is unsubstituted or substituted alkyl. In certain embodiments, $R^1$ is unsubstituted alkyl. For example, $R^1$ may be methyl, ethyl, propyl, butyl, pentyl, hexyl, heptyl, octyl, nonyl, or decyl. In one embodiment, $R^1$ is methyl. In certain embodiments, $R^1$ is alkyl substituted with unsubstituted aryl, substituted aryl, unsubstituted heteroaryl, or substituted heteroaryl. In one embodiment, $R^1$ is alkyl substituted with unsubstituted or substituted furan, or unsubstituted or substituted phenyl.

In other embodiments of this method, $R^3$ of the aldehyde having the structure of formula (C) is unsubstituted or substituted alkyl. In certain embodiments, $R^3$ is unsubstituted alkyl. For example, $R^3$ may be methyl, ethyl, propyl, butyl, pentyl, hexyl, heptyl, octyl, nonyl, or decyl. In one embodiment, $R^3$ is methyl. In certain embodiments, $R^3$ is alkyl substituted with unsubstituted aryl, substituted aryl, unsubstituted heteroaryl, or substituted heteroaryl. In one embodiment, $R^3$ is alkyl substituted with unsubstituted or substituted furan, or unsubstituted or substituted phenyl. In other embodiments, $R^3$ is unsubstituted or substituted aryl.

Formation of Acyclic Ketones

Acyclic ketones may be produced by oligomerization of the alkyl ketones described above in the presence of the catalysts and certain hydrogen sources. Acyclic ketones may also be produced by oligomerization of alkyl alcohols described below.

Alkyl Ketones and Hydrogen Source

The use of certain alkyl ketones in the presence of a certain hydrogen sources may, in some instances, favor dimerization to form acyclic ketones over trimerization to form cyclic ketones. For example, in some embodiments, such alkyl ketones of formula (A) may include:

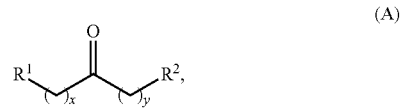
(A)

wherein:
each $R^1$ and $R^2$ is independently H, unsubstituted alkyl, substituted alkyl, —C($R^t$)$_3$, —CH($R^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
  wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
x is an integer greater than or equal to 1; and
y is an integer greater than or equal to 0.

In certain embodiments, $R^1$ is H, unsubstituted alkyl, substituted alkyl, —C($R^t$)$_3$, —CH($R^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl; and $R^2$ is unsubstituted alkyl, substituted alkyl, —C($R^t$)$_3$, —CH($R^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, Any suitable hydrogen source may be used. For example, in some embodiments, hydrogen gas can be fed into the reaction vessel. For example, the reaction vessel may have a hydrogen pressure between 100 to 1500 psi.

In other embodiments, the hydrogen source is a secondary alcohol. Examples of secondary alcohols suitable for use as a hydrogen source in the reaction include isopropyl alcohol, 2-butanol, and 2-pentanol. In certain embodiments, the hydrogen source is a secondary alcohol having the structure of formula (B), as described in further detail below.

Alkyl Alcohols

Alkyl alcohols used in the methods described herein have at least one methylene group in the alpha position (i.e., relative to the hydroxyl group). The alkyl alcohols may independently have a structure of formula (B):

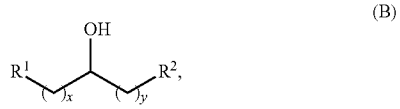
(B)

wherein:

each $R^1$ and $R^2$ is independently H, unsubstituted alkyl, substituted alkyl, —$C(R')_3$, —$CH(R')_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, wherein each $R'$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl; and each x and y is independently an integer greater than or equal to 1.

In some embodiments, the alcohol having the structure of formula (B) is an alcohol having the structure of formula (B-1):

(B-1)

wherein x is an integer greater than or equal to 2.

In some embodiments of the alcohol having the structure of formula (B) or (B-1), $R^1$ is unsubstituted or substituted alkyl. In certain embodiments, $R^1$ is unsubstituted alkyl. For example, $R^1$ may be methyl, ethyl, propyl, butyl, pentyl, hexyl, heptyl, octyl, nonyl, or decyl. In one embodiment, $R^1$ is methyl. In certain embodiments, $R^1$ is alkyl substituted with unsubstituted aryl, substituted aryl, unsubstituted heteroaryl, or substituted heteroaryl. In one embodiment, $R^1$ is alkyl substituted with unsubstituted or substituted furan, or unsubstituted or substituted phenyl.

In some embodiments of the alcohol having the structure of formula (B) or (B-1), $R^2$ is unsubstituted or substituted alkyl. In certain embodiments, $R^2$ is unsubstituted alkyl. For example, $R^2$ may be methyl, ethyl, propyl, butyl, pentyl, hexyl, heptyl, octyl, nonyl, or decyl.

In one embodiment of the alcohol having the structure of formula (B) or (B-1), $R^2$ is methyl. It should be understood that when $R^2$ is methyl, the alcohol having the structure of formula (B) or (B-1), is a methyl alcohol. In another embodiment, $R^1$ is unsubstituted or substituted alkyl, and $R^2$ is methyl. It should be understood that when $R^1$ is unsubstituted or substituted alkyl, and $R^2$ is methyl, the alcohol having the structure of formula (B) or (B-1), is an alkyl methyl alcohol. In certain embodiments of the alcohol having the structure of formula (B) or (B-1), when $R^1$ or $R^2$ is alkyl, the alkyl may be unbranched or branched. In one embodiment, the alkyl is branched.

In some embodiments that can be combined with any of the foregoing embodiments of the ketone having a structure of formula (B) or (B-1), x is 3 to 45. In certain embodiments, x is 3 to 21. In one embodiment, x is 3, 5, 7 or 9.

Acyclic Ketone Products

Acyclic ketones produced according to the methods described herein include compounds in which carbon atoms are connected to form a non-ring structure (e.g., a linear or branched structure), wherein at least one carbonyl group (C=O) is bonded to two of the non-ring carbon atoms. It should be understood that acyclic ketones may, in certain embodiments, be substituted with one or more cyclic moieties.

The acyclic ketones may, for example, have a structure of formula (L-I) or (L-II):

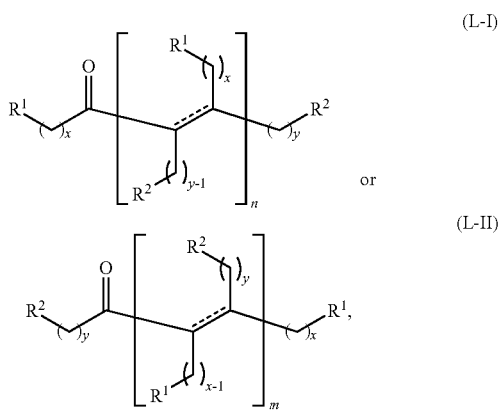

or any isomers thereof, wherein:

each $R^1$ and $R^2$ is independently H or unsubstituted alkyl;

each x and y is independently an integer greater than or equal to 1;

n and m are each an integer greater than or equal to 1, and the dotted line represents a single bond when a hydrogen source (e.g., $H_2$ or a secondary alcohol) is present, and a double bond when a hydrogen source is absent.

Under certain conditions, the ketone having the structure of formula (A) or the alcohol having the structure of formula (B) may dimerize to form the acyclic ketones having a structure of formula (L-I-1) or (L-II-1), where a hydrogen source is present:

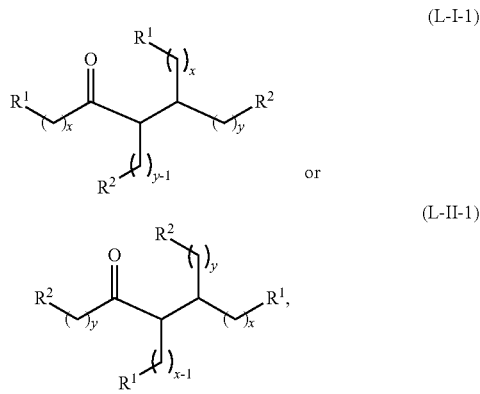

or any isomers thereof, or the acyclic ketones having a structure of formula (L-I-1') or (L-II-1'), where a hydrogen source is absent:

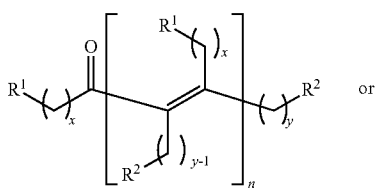

(L-I-1')

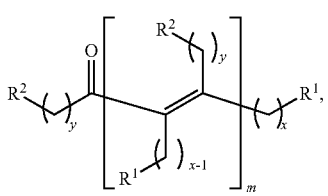

(L-II-1')

or any isomers thereof, wherein $R^1$, $R^2$, x and y are as defined for the ketone having the structure of formula (A) or the alcohol having the structure of formula (B), as the case may be depending on the reactants used.

In certain embodiments, when the alkyl ketone is a methyl ketone having the structure of formula (A-1), or the alkyl alcohol is a methyl alcohol having the structure of formula (B-1), the alkyl ketone or alkyl alcohol can dimerize to form acyclic ketones having a structure of formula (L-I-2) or (L-II-2), where a hydrogen source is present:

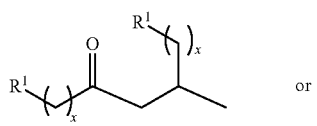

(L-I-2)

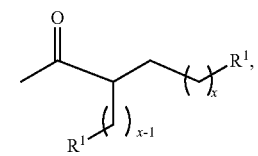

(L-II-2)

or any isomers thereof, or the acyclic ketones having a structure of formula (L-I-2') or (L-II-2'), where a hydrogen source is absent:

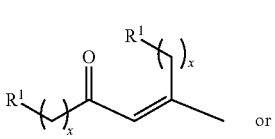

(L-I-2')

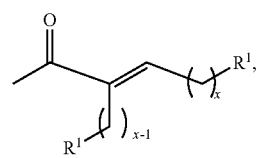

(L-II-2')

or any isomers thereof, wherein $R^1$ and x are as defined for the ketone having the structure of formula (A) or the alcohol having the structure of formula (B), as the case may be depending on the reactants used.

It should be understood that isomers of the cyclic ketones of formula (L-I), (L-II), (L-I-1), (L-II-1), (L-I-2), (L-II-2), (L-I'), (L-II'), (L-I-1'), (L-II-1'), (L-I-2') and (L-II-2') may be produced. Such isomers may include stereoisomers.

TABLE C

| Ketone Reactant | Alcohol Reactant | Acyclic Dimer Ketone Products |
|---|---|---|
| ![ketone structure with R¹ and R²] | ![alcohol structure with R³, R⁴ and OH] | ![four pairs of acyclic dimer ketone product structures with various R¹, R², R³, R⁴ substituents] |
| each $R^1$, $R^2$, $R^3$ and $R^4$ is unsubstituted or substituted alkyl | | |
| For example: each $R^1$, $R^2$, $R^3$ and $R^4$ is methyl, ethyl, n-propyl, iso-propyl, n-butyl, iso-butyl, n-pentyl, n-hexyl, 2-ethylhexyl, phenyl, | | |
| ![bis-furyl methane structures with Me substituents] | | |
| | | or any isomers or mixtures thereof |

It should also be understood by one of skill in the art that the structure of the acyclic ketones of formula (L-I) or (L-II) will correspond to the structure of alcohol(s) of formula (B) used. Table C below provides examples of acyclic ketones having the structure of formula (L-I) or (L-II) that may be produced from a ketone of formula (A) and/or an alcohol of formula (B).

In some embodiments of the method described herein to produce the acyclic ketones, at least 50%, at least 60%, at least 70%, at least 80%, at least 85%, at least 90%, at least 95%, at least 96%, at least 97%, at least 98%, or at least 99% of the products in the reaction mixture are the acyclic ketones of formula (L-I) and/or (L-II), or any isomers thereof. Various factors may cause the reaction to favor dimerization to form cyclic ketones over other competing reactions (e.g., dimerization, tetramerization or other oligomerization reactions), as well as to favor the formation of certain acyclic ketones. Factors that allow the tuning of the reaction may include, for example, the choice of starting materials and the amount of water in the reaction mixture.

Choice of Alkyl Ketones

In some embodiments, the acyclic ketones of formula (L-I) and/or (L-II), or any isomers thereof, are produced when certain alkyl ketones are used. For example, in certain embodiments, such alkyl ketones include ketones having the structure of formula (A):

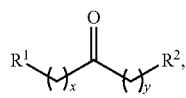

(A)

wherein each x and y is greater than 1, and R¹ and R² is as defined herein for formula (A). Examples of such ketones include:

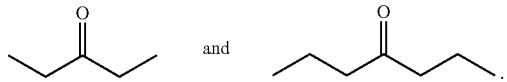

In certain embodiments, the total chain length of the ketone is at least 6 carbon atoms, or is 6 or 7 carbon atoms.

In other embodiments, the acyclic ketones of formula (L-I) and/or (L-II), or any isomers thereof, are produced when certain methyl ketones are used, including ketones having the structure of formula (A-3):

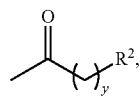

(A-3)

wherein:
y is 0; and
R² is as defined for formula (A), provided that R² is other than H.

In certain embodiments, R² is —C(R')₃ or —CH(R')₂. In one embodiment, R² is —C(R')₃ or —CH(R')₂, and each R' is independently unsubstituted or substituted alkyl. In another embodiment, each R' is unsubstituted alkyl. Examples of ketones having the structure of formula (A-3) used to produce the acyclic ketones of formula (L-I) and/or (L-II), or any isomers thereof, include:

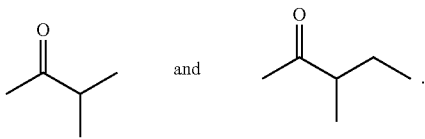

Choice of Catalysts

In some embodiments, the use of certain catalysts may favor dimerization to form acyclic ketones over other reactions. For example, in certain embodiments the acyclic ketones of formula (L-I) and/or (L-II), or any isomers thereof, are produced when basic catalysts are used with ketones having the structure of formula (A) is:

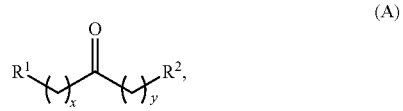

(A)

wherein each x and y is greater than 1, and R¹ and R² is as defined herein for formula (A).

In other embodiments, the acyclic ketones of formula (L-I) and/or (L-II), or any isomers thereof, are produced when basic catalysts are used with ketones having the structure of formula (A-3) is:

(A-3)

wherein:
y is 0; and
R² is as defined for formula (A), provided that R² is other than H.

Catalysts

Catalysts suitable for catalyzing the oligomerization, including the trimerization and dimerization, of an alkyl ketone or an alkyl alcohol may be used in the methods described herein. The catalysts suitable for use herein may be characterized in various ways. For example, the catalyst used may be solid. In some embodiments, the catalyst is heterogeneous in the reaction mixture. The catalyst may also be recovered and recycled in the methods described herein. In other embodiments, the catalyst is homogeneous in the reaction mixture.

Basic

In some embodiments, the catalyst is basic. Catalyst basicity may be measured by a variety of techniques known to one of skill in the art. For example, basicity of the catalyst may be expressed based on pKa and/or CO₂ desorption. Quantitative determination of pKa and other methods to characterize the basicity of a catalyst are known in the art. See, e.g., A. Corma, et al., *J. of Catalysis*, 1992, 134, 58; and D. Debecker, et al., *Chem. Eur. J.*, 2009, 15, 3920.

Basic catalysts may include basic oxygen atoms bound to one or more metal atoms. These metal atoms may be single component metal oxides, including alkali and alkaline earth oxides, non-metal oxides transition metal oxides, rare metal oxides, and any combinations thereof. For example, the metal atoms may be selected from Mg, Ca, Sr, Ba, Ti, Zr, Al, Na, K, Cs, Rb, Zn, and lanthanides, or any combinations thereof. In some embodiments, the basic catalysts may also include an electronegative atom, such as fluorine or nitrogen, bound to one of the aforementioned metals. Basic catalysts may also be characterized by their proton affinities of their surfaces or of any cluster or clusters, anionic or neutral, which are subsets of their structure. See e.g., Phys. Chem. Chem. Phys., 1999, 1, 4453-4458; J. Am. Chem. Soc. Vol. 112, No. 20, 1990; and J. Phys. Chem. B, 1997, 101, 1347.

In certain embodiments, the catalyst includes a support that has one or more basic sites for Michael addition and/or aldol chemistry. Examples of such catalysts include MgO, alkali doped MgO, SrO, BaO, CaO, ZnO, $La_2O_3$, $TiO_2$, $ZrO_2$, and $Al_2O_3$. In other embodiments, the catalyst has 0.25 mol % to 2 mol % basic sites.

In other embodiments, the catalyst is acidic. Such catalysts may contain Lewis and/or Bronsted acid sites (e.g., niobium phosphate). These sites can be characterized by the desorption temperature of basic probe molecules. See Journal of Catalysis, 54(3), 1978, 303-317. In yet other embodiments, the catalyst is amphoteric.

Certain catalysts may be selected to tune the reaction such that trimerization and/or dimerization is favored over other competing reactions. In some embodiments, trimerization of the alkyl ketones described herein may be catalyzed by a catalyst having one or more of the following properties:

(i) a pKa between 8 to 16;

(ii) a $CO_2$ desorption of at least 50° C., at least 100° C., or at least 200° C., or between 50° C. and 600° C., or between 120° C. and 200° C., wherein $CO_2$ desorption is carried out by adsorbing $CO_2$ to the catalyst at room temperature and heating up to 773 K;

(iii) at least one basic oxygen atom; and (iv) a proton affinity of at least 700 kJ/mol.

In other embodiments, dimerization of the alkyl ketones or alkyl alcohols described herein may be catalyzed by a catalyst that is a weak base, including for example $KF/Al_2O_3$, $SrTiO_3$ (Sr-titanate), or pervoskites. Dimerization may also be favored using any of the catalysts described herein, in the present of water (e.g., greater than 1 wt %, greater than 1.5 wt %, greater than 2 wt %, or between 1 wt % and 10 wt %, or between 1 wt % and 5 wt % of water in the reaction mixture).

Acidic

Acidic catalysts suitable for use in the methods described herein may include, for example, $SiO_2$—$Al_2O_3$, niobium oxides (e.g., $Nb_2O_3$ and $Nb_2O_5$), molybdenum oxides ($MoO_2$ and $MoO_3$), and tungsten oxides (e.g., $WO_2$ and $WO_3$).

In some embodiments, trimerization of the alkyl ketones described herein may be catalyzed by a catalyst having one or more of the following properties:

(i) an ammonium adsorption energy of at least 80 kJ/mol, at least 90 kJ/mol, at least 110 kJ/mol, or at least 130 kJ/mol; and (ii) at least $1 \times 10^{20}$ mol, at least $2 \times 10^{20}$ mol, at least $3 \times 10^{20}$ mol, at least $4 \times 10^{20}$ mol, or at least $5 \times 10^{20}$ mol of acid sites/g of catalyst, corresponding to pretreatment under vacuum at 473 K.

Amphoteric

In yet other embodiments, the catalyst is amphoteric. Amphoteric catalysts suitable for use in the methods described herein may include, for example, hydroxyapatite (HAP), $TiO_2$, and $ZrO_2$.

Other Examples of Suitable Catalysts

Examples of suitable catalysts for use in the methods herein are provided below. In certain embodiments, the catalyst is selected from or includes:

hydrotalcite;
zeolite;
metal oxide;
non-metal oxide;
supported alkali metal ion;
apatite;
sepiolite;
chrysotile;
mesoporous silica;
ionic liquid supported metal oxide;
aluminophosphate;
synthetic talc; or
non-oxide supported on alumina,
or any combinations thereof.

In certain embodiments, the catalyst includes hydrotalcite. The hydrotalcite may be calcined using any methods known in the art. The hydrotalcites may also under hydrothermal treatment. In certain embodiments, the hydrotalcite includes one or more metals selected from the group consisting of magnesium, aluminum, lithium, zinc, copper, and nickel. In certain embodiments, the hydrotalcite is Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite, or any combinations thereof. In one embodiment, the hydrotalcite is MgAlO. In another embodiment, the hydrotalcite is selected from the group consisting of Mg—Al, Li—Al, Zn—Al, Cu—Zn—Al, and Ni—Mg—Al hydrotalcite.

Basicity of hydrotalcites can be tuned by varying the magnesium-aluminum ratio, by rehydrating calcined hydrotalcite, and doping hydrotalcite with Na and K. In some embodiments, hydrotalcites are prepared by co-precipitation of alkaline earth metal salts and/or aluminum nitrates in a solution that includes urea or ammonia and ammonium carbonate or potassium hydroxide and potassium carbonate or sodium hydroxide and sodium carbonate. In some embodiments, alkaline earth metal supports might be prepared by decomposition of nitrate, carbonate or dicarboxylic acid salts at elevated temperatures, from 450° C. to 900° C.

In certain embodiments, the catalyst includes zeolite. The zeolite may be, for example, alkali-exchanged zeolites. For example, in one embodiment, the zeolite is NaY, NaX, KY, RbY, CsY, KX, RbX, or CsX zeolite.

In certain embodiments where the catalyst is hydrotalcite or zeolite, $Cs_2CO_3$ or KOH may be impregnated on the hydrotalcite or zeolite.

In some embodiments, the catalyst includes an alkali oxide, an alkaline earth oxide, a non-metal oxide, a transition metal oxide, or a rare metal oxide, or any combinations thereof. In another embodiment, the catalyst is or includes an alkali oxide, an alkaline earth oxide, a rare metal oxide, or any combinations thereof. Examples of such catalysts may include $Cs_2O$, MgO, $TiO_2$, $ThO_2$, $ZrO_2$, ZnO, and $La_2O_3$. The catalyst may also undergo impregnation of ionic liquids. For example, ionic liquid may be impregnated on MgO.

In certain embodiments, the catalyst includes a metal oxide. In some variations, the catalyst includes a metal oxide and a silica support. In some embodiments, the silica support is mesoporous silica. For example, in one embodiment, the metal oxide is $Ta_2O_5$, which in certain variations may be combined with or impregnated on a silica support. Thus, in some embodiments, the catalyst includes $Ta_2O_5$ impregnated on a silica support. In one embodiment, the metal oxide is $Ta_2O_5$, which in certain variations may be combined with or impregnated on mesoporous silica. Thus, in some embodiments, the catalyst includes $Ta_2O_5$ impregnated on mesoporous silica. In certain variations, the mesoporous silica may be modified. One example of a modified mesoporous silica that may be used with metal oxides, such as $Ta_2O_5$, is SBA-15. In certain embodiments where the catalyst includes $Ta_2O_5$ impregnated on modified mesoporous silica, the modified mesoporous silica is SBA-15. Thus, in some embodiments, the catalyst includes $Ta_2O_5$ impregnated on SBA-15.

In some embodiments, the catalyst may be a solid-supported metal catalyst. A solid-supported metal catalyst used herein typically is a metal catalyst where the metal is deposited or impregnated onto a support.

In some embodiments, the catalyst includes Mg, Ti, Sr, Ca, Si, Al, La, Zr, Na or K, or any combinations thereof. In one embodiment, the catalyst is selected from or includes: MgO, SrO, BaO, CaO, ZnO, $La_2O_3$, $TiO_2$, $ZrO_2$, $Al_2O_3$, $Ta_2O_5$, Mn oxide, Cr oxide, Y oxide, $Nb_2O_3$, Mo oxide, W oxide, $ThO_2$, $HfO_2$, $CeO_2$, Yb oxide, $Sc_2O_3$, $V_2O_5$, or other alkali-doped variations thereof;

Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite;

NaY zeolite, NaX zeolite, KY zeolite, RbY zeolite, CsY zeolite, KX zeolite, RbX zeolite, CsX zeolite, palladium/NaY zeolite, palladium/$NH_4$-β zeolite, potassium oxide supported on zeolite Y, lanthanide imide on zeolite, or nitride on zeolite;

$Cs_2CO_3$ or KOH impregnated on a hydrotalcite or a zeolite;

ionic liquid impregnated on MgO;

$Cs_2O$, MgO, $TiO_2$, $ThO_2$, $ZrO_2$, ZnO, $CeO_2$, $Ta_2O_5$, $MnO_x$, or $La_2O_3$;

Na/$SiO_2$ Pd/Na/$SiO_2$, Na/Ca/$SiO_2$, Na/Ca/$SiO_2$, or Cs/$SiO_2$;

hydroxyapatite, fluorapatite, or tert-butoxyapatite;

sepiolite;

$Mg_3(OH)_4Si_4O_5$, or cobalt(II)-substituted chrysotile;

amino-functionalized mesoporous silica (e.g., MCM-41);

modified mesoporous silica (e.g., SBA-15);

ionic liquid supported MgO;

amorphous aluminophosphate (ALPO);

magnesium organo silicate; or

KF supported on alumina, or any combinations thereof.

In other embodiments, the catalyst includes a metal. In certain embodiments, the metal is a transition metal. In certain embodiments, the metal is a late transition metal. In some embodiments, the catalyst includes a metal selected from the group consisting of ruthenium, iron, palladium, platinum, cobalt, and copper. Mixtures of these metals are also contemplated, including for example metal alloys. In some embodiments, the ruthenium, iron, palladium, platinum, cobalt, and copper, either used alone or in combination, may also be combined with other metals such as lanthanides. In other embodiments, the catalyst may include transition metals such as nickel, ruthenium, rhodium, palladium, rhenium, iridium, gold, silver, or platinum. In other embodiments, the catalyst includes palladium or platinum.

In some embodiments, the catalyst is a single component metal oxides such as alkaline earth oxides, alkali metal oxides, transition metal oxides, rare earth oxides ($Cs_2O$, MgO, $TiO_2$, $ThO_2$, $ZrO_2$, ZnO, $Sc_2O_3$, $CeO_2$, MnOx, CrOx, WOx, $V_2O_5$, $Ta_2O_5$, $Nb_2O_3$, or $La_2O_3$).

In some embodiments, the catalyst may be a solid-supported metal catalyst. A solid-supported metal catalyst used herein typically is a metal catalyst where the metal is deposited or impregnated onto a support.

In some embodiments, the support is selected from the group consisting of hydrotalcite, single component metal oxides, alkaline earth oxides, alkali metal oxides, rare earth oxides, $ThO_2$, MgO, Na doped MgO, SrO, BaO, CaO, ZnO, $La_2O_3$, $TiO_2$, $ZrO_2$, $Al_2O_3$, $Ta_2O_5$, Mn oxide, Cr oxide, Y oxide, $Nb_2O_3$, Mo oxide, W oxide, $ThO_2$, $HfO_2$, $CeO_2$, Yb oxide, $Sc_2O_3$, $V_2O_5$, hydroxyapatite, fluorapatite, tert-butoxyapatite, sepiolite, basic zeolites, alkali ion-exchanged zeolites, alkali ion-added zeolites, Pd/NaY zeolite, Pd/$NH_4$-3 zeolite, supported alkali metal ions, alkali metal ions on alumina, alkali metal ions on silica, alkali metal on alkaline earth oxide, alkali metals and alkali metal hydroxides on alumina, metal/$SiO_2$, Na/$SiO_2$ Pd/Na/$SiO_2$, Na/Ca/$SiO_2$, NaJCa/$SiO_2$, Cs/$SiO_2$, metal-supported zeolite, potassium oxide supported on zeolite Y, synthetic chrysotiles, $Mg_3(OH)_4Si_4O_5$, cobalt(II)-substituted chrysotile, amino-functionalized mesoporous silica, amino-functionalized MCM-41, alkali ion-exchanged mesoporous silica, alkali ion-exchanged SBA-15, ionic liquid supported MgO, amorphous aluminophosphate, synthetic talcs, magnesium organo silicates, KF supported on alumina, lanthanide imide on zeolite, and lanthanide nitride on zeolite. In some embodiments, the support is an alkali exchanged zeolite such as NaY, KY, RbY, CsY, NaX, KX, RbX, and CsX. In some embodiments a metal such as Pd or Cu is deposited on the alkali exchanged zeolite and used as the metal based catalyst such as, for example, Pd/CsY and Cu/CsY. In some embodiments, alkali metal ions are added to the support (e.g., alkali metal ions on alumina, alkali metal ions on silica, alkali metal on alkaline earth oxide, alkali metals and alkali metal hydroxides on alumina).

It should be understood that the catalyst can be obtained from any commercially available source, or prepared by any methods known to one of skill in the art. For example, incipient wetness impregnation is one exemplary technique that can be used. In one example, a support such as hydrotalcite, and metal salt such as palladium chloride or copper acetate can be combined and a solvent such as water is added. The metal salt and support are allowed to react for a period of time between 1 and 24 hours at a temperature between room temperature and 200° C., or more specifically between 50 and 120° C. The reaction mixture may be stirred under a hydrogen atmosphere. The solid catalyst is then filtered and washed with copious amounts of solvent. The solid may then be dried under vacuum at a temperature between 80 and 150° C. Optionally, other additives may be added to the reaction mixture such as alkali metal salts (e.g., sodium chloride or potassium chloride) or a base as described above.

The catalyst may also be prepared by incipient wetness impregnation of metal salts on basic supports, followed by calcination at temperatures higher than 300° C. in air or inert gases and/or reduction in mixtures of hydrogen and inert gases. Alternatively, the catalyst may be prepared by synthesizing metal nanoparticle ex situ and supporting said nanoparticles on the basic metal support using a solvent. In some embodiments, the catalyst prepared by incipient wetness impregnation includes at least two metals. For example, the catalyst may contain Pd and Cu (e.g., Pd/Cu). The ratio of Pd and Cu can vary, in which Pd may be in molar excess of Cu (e.g., in a 3:1 molar ratio).

The catalyst may also be prepared by using the aforementioned methods for supporting metals on basic supports, with the difference that the supports are inert and include $SiO_2$ and carbon. The basic supports are also prepared as mentioned above, but no metal is supported on them. The basic supports and the metal catalysts are physically mixed before the reaction.

The catalyst may also be prepared by simultaneous or successive incipient wetness impregnation of solutions of nitrate or acetate salts of alkali or alkaline earth metals and appropriate salts or complexes of the metals disclosed herein onto inert supports, followed by calcination and reduction in conditions mentioned above. Alternatively, the catalyst may be prepared by incipient wetness impregnation of alkali salts onto inert supports, followed by calcination and incipient wetness impregnation of ex-situ synthesized metal nanoparticles.

The amount of catalyst used in the methods described herein may vary depending on various factors. The catalyst loading may have impact on tuning the reaction to favor trimerization over dimerization and other competing reactions. As used herein, catalyst loading refers to the number of available basic sites per mole of reactant. For example, in the method to produce cyclic ketones, the catalyst loading may be 0.25-2 mol % of basic sites on the catalyst (as determined by temperature-programmed desorption (TPD) studies). In another example, in the method to produce acyclic ketones, the catalyst loading may be 0.25-2 mol % of metal and 0.25-2 mol % of basic sites on the catalyst (determined by TPD studies).

Solvents

In some variations of the methods provided herein, the method may be performed in the absence of a solvent (i.e., neat). In other variations, the method may be performed in the presence of a solvent.

Any solvent or mixture of solvents that promotes oligomerization, including specifically trimerization and dimerization, of an alkyl ketone or an alkyl alcohol. For example, the solvent may be an organic solvent.

Suitable solvents may include, for example, hydrocarbons (acylic or cyclic), aromatics (e.g., toluene, xylene, benzene), ketones (e.g., acetone, methyl ethyl ketone, 4-heptanone, 4-nonanone, 6-undecanone), alcohols (e.g., butanol, ethanol, isopropanol), or ethers (e.g., dibutyl ether, diglyme, diglybu, dioxane). As used herein, "diglyme" refers to diethylene glycol dimethyl ether. As used herein, "diglybu" refers to diethylene glycol dibutyl ether.

In certain embodiments, the solvent includes hydrocarbon solvent(s). In one embodiment, the solvent includes octane. In other embodiments, the solvent includes aromatic solvent(s). In one embodiment, the solvent includes toluene. The cycloalkanes that may be produced according to the methods described herein may also be selected as suitable solvents.

In certain embodiments, the solvent includes an alkane, toluene, xylene, dibutyl ether, diglyme, diglybu, dioxane, 4-heptanone, 4-nonanone, 6-undecanone, or any mixtures or combinations thereof.

In some embodiments, the solvent may include any suitable solvents that forms an azeotrope with water. In other embodiments, the solvent has a higher boiling point than water. Such solvents may be suitable for use in the methods to produce cyclic ketones, favoring trimerization of the alkyl ketone over other oligomerization reactions (e.g., dimeriation to form acyclic ketones).

In other embodiments, the methods described herein may be performed neat, i.e., without addition of a solvent.

Reaction Conditions

Reaction Temperature

The methods described herein may be performed at any suitable temperature and pressure to produce the cyclic ketones and/or acyclic ketones. In certain embodiments, the method is performed at a temperature between 90° C. to 250° C.; or between 90° C. to 120° C.; or between 120° C. to 160° C.; or between 160° C. to 250° C.

For example, in some embodiments, the reaction mixture may be heated to a temperature suitable to increase selectivity of the trimerized products. In some embodiments, the method is performed at a temperature between 150° C. to 250° C. In certain embodiments, the method is performed at a temperature between 150° C. to 200° C.

In other embodiments, the reaction mixture may be heated to a temperature suitable to increase selectivity of the dimerized products. In certain embodiments, the method is performed at a temperature between 80° C. to 150° C.

In other embodiments, trimers may be favored when the temperature is between 300° C. and 400° C.; and dimers may be favored when the temperature is less than 200° C.

Reaction Time

The methods described herein may produce cyclic ketones and/or acyclic ketones in less than 24 hours, depending on the reaction conditions. For example, in some embodiments of producing the cyclic ketones described herein, at least 50% of the alkyl ketones are converted into at least one cyclic ketone in less than 24 hours, less than 12 hours, less than 6 hours, or less than 1 hour. In certain embodiments of producing the cyclic ketones described herein, at least 75% of the alkyl ketones are converted into at least one cyclic ketone in less than 24 hours, less than 12 hours, less than 6 hours, or less than 1 hour. In certain embodiments of producing the cyclic ketones described herein, at least 80% of the alkyl ketones are converted into at least one cyclic ketone in less than 24 hours, less than 12 hours, less than 6 hours, or less than 1 hour. In certain embodiments of producing the cyclic ketones described herein, at least 90% of the alkyl ketones are converted into at least one cyclic ketone in less than 24 hours, less than 12 hours, less than 6 hours, or less than 1 hour.

In some embodiments of producing the acyclic ketones described herein, at least 50% of the alkyl ketones or alkyl alcohols are converted into at least one acyclic ketone in less than 24 hours, less than 12 hours, less than 6 hours, or less than 1 hour. In certain embodiments of producing the acyclic ketones described herein, at least 75% of the alkyl ketones or alkyl alcohols are converted into at least one acyclic ketone in less than 24 hours, less than 12 hours, less than 6 hours, or less than 1 hour. In certain embodiments of producing the acyclic ketones described herein, at least 80% of the alkyl ketones or alkyl alcohols are converted into at least one acyclic ketone in less than 24 hours, less than 12 hours, less than 6 hours, or less than 1 hour. In certain embodiments of producing the acyclic ketones described herein, at least 90% of the alkyl ketones or alkyl alcohols are converted into at least one acyclic ketone in less than 24 hours, less than 12 hours, less than 6 hours, or less than 1 hour.

Formation of Other Products

The alkyl ketones described herein can oligomerize to form the cyclic and acyclic ketones described herein, as well as other products including aromatic compounds and other oligomers (e.g., tetramers).

For example, the ketones having the structure of formula (A) may additionally produce at least one aromatic compound having the structure of formula (N-I), (N-II), or (N-III):

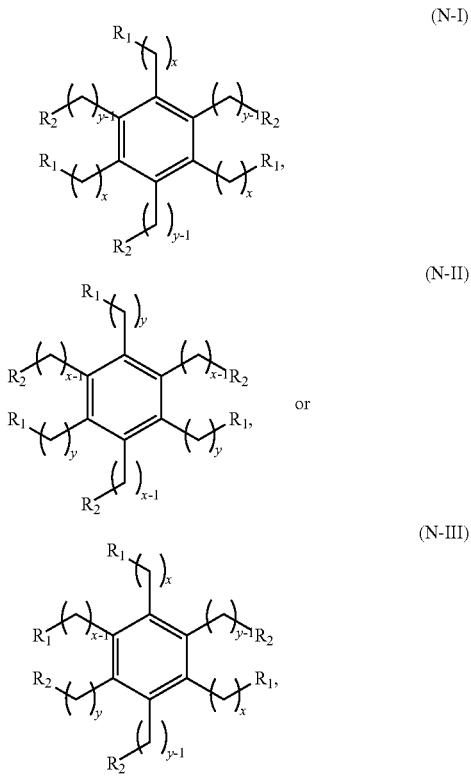

or any positional isomers thereof, wherein $R^1$, $R^2$, x and y are as defined for formula (A). In one variation, the at least one aromatic compound has the structure of formula (N-I), (N-II), or (N-III).

Figure 3:
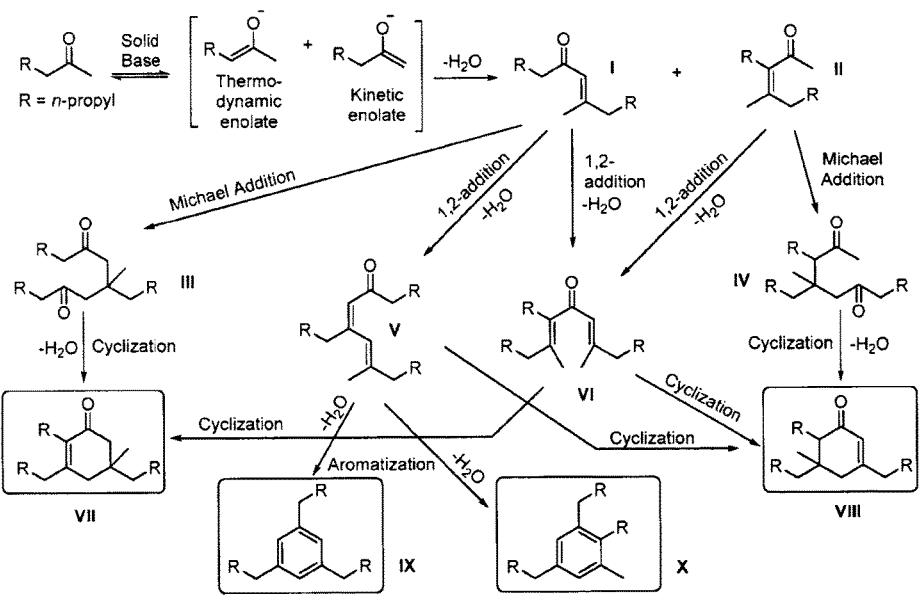
FIG. 3 depicts exemplary reaction pathways for the self-condensation of 2-hexanone.

Without wishing to be bound by any theory, FIG. 3 provides various reaction pathways to form cyclic, linear and aromatic compounds from self-condensation of 2-hexanone. The base catalysis of an exemplary alkyl ketone, 2-hexanone, may involve two reversible enolate formations, namely, kinetic as well as thermodynamic enolates. These enolates may lead to self-condensations to form dimers I and II. Michael addition of the kinetic enolate with I and two II may produce intermediates III and IV, which upon dehydrative cyclization may yield the cyclized products VII and VIII, respectively. Alternatively, the 1,2-addition of the 2-hexanone enolate on intermediates I and II may produce V and VI, which upon cyclization would produce products VII and VIII. Additionally, aromatic products (IX and X) formations may be produced by the dehydrative aromatizations of V.

The alkyl ketones can oligomerize to form tetramers, pentamers and other oligomers. However, the reaction can be tuned to reduce the other oligomers (i.e., other than trimers and dimers) formed. In certain embodiments, the methods described herein produce a reaction mixture with less than 15 wt % tetramers, pentamers, and other oligomers. In other words, at least 80-85 wt % of the reaction mixture is made up of trimers and dimers.

Compositions

Alkyl Ketone Compositions

In certain aspects, provided herein is a composition that includes:

a ketone having the structure of formula (A):

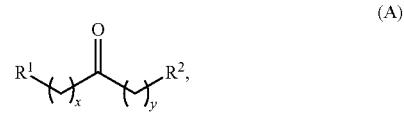

wherein:

each $R^1$ and $R^2$ is independently H, unsubstituted alkyl, substituted alkyl, —C(R')$_3$, —CH(R')$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, wherein each R' is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;

each x and y is independently an integer greater than or equal to 1; and a catalyst.

It should be understood that the composition above may include any of the embodiments of the ketone having the structure of formula (A) as described herein. For example, in one embodiment, the composition comprises a ketone having the structure of formula (A-1):

wherein x is an integer greater than or equal to 2.

Further, the composition above may include any of the embodiments of the catalyst described herein. In some embodiments, the composition includes basic catalyst, as described above. In one embodiment, the catalyst is hydrotalcite. In other embodiments, the composition includes acidic catalyst, as described above.

In some embodiments, the composition further includes water. In certain embodiments of the composition (e.g., where basic catalyst is present), the amount of water present is less than 1 wt %, less than 0.9 wt %, less than 0.8 wt %, less than 0.7 wt %, less than 0.6 wt %, less than 0.5 wt %, less than 0.4 wt/o, less than 0.3 wt %, less than 0.2 wt %, or less than 0.1 wt % of water.

Alkyl Alcohol Composition

In other aspects, provided herein is a composition that includes:

an alcohol having a structure of formula (B):

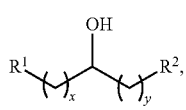

(B)

wherein:
each $R^1$ and $R^2$ is independently H, unsubstituted alkyl, substituted alkyl, —C(R$^t$)$_3$, —CH(R$^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
  wherein each $R^t$ is independently unsubstituted aliphatic, substituted aliphatic, substituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1; and
a heterogeneous catalyst.

It should be understood that the composition above may include any of the embodiments of the alcohol having the structure of formula (B) as described herein. For example, in one embodiment, the composition comprises an alcohol having the structure of formula (B-1):

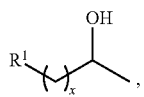

(B-1)

wherein x is an integer greater than or equal to 1.

Further, the composition above may include any of the embodiments of the catalyst described herein. For example, in one embodiment of the composition, the heterogeneous catalyst is hydrotalcite.

Uses of the Cyclic and Acyclic Ketones

The cyclic and acyclic ketones produced according to the methods described herein may be converted to their corresponding alkanes using any suitable methods and techniques known in the art. For example, the cyclic and acyclic ketones can be hydrodeoxygenated to produce alkanes. Such alkanes may be used as jet fuels or lubricants.

One of skill in the art would recognize the suitable catalyst and reactions conditions that may be used to perform the hydrodeoxygenation reaction. For example, the hydrodeoxygenation catalyst may include Ni, Pt, Pd, Rh, Ru, Cu, and other transition metals. In combination with metals, acidic supports such NbOPO$_4$, Nb$_2$O$_5$, SiO$_2$—Al$_2$O$_3$, Ta$_2$O$_5$, TiO$_2$, ZrO$_2$, and sulfated ZrO$_2$ may also be used to provide hydrogenation activity. One such catalyst is Pt/NbOPO$_4$. Another such catalyst is Rh/C. Yet another such catalyst is Pd/C.

Cycloalkanes

The cyclic ketones having the structure of formula (I), (II), (III) or (IV), or any isomers thereof, can be hydrodeoxygenated to form their respective cycloalkanes.

For example, in some embodiments, a cyclic ketone having a structure of formula (I) may be hydrodeoxygenated to form a cycloalkane having a structure of formula (X-I), wherein:

the cyclic ketone having a structure of formula (I) is:

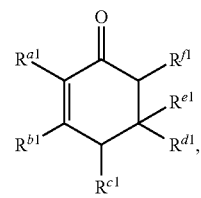

(I)

wherein:
$R^{a1}$ is —(CH$_2$)$_{x-1}$R$^1$;
$R^{b2}$ is —(CH$_2$)$_x$R$^1$;
$R^{c1}$ is —(CH$_2$)$_{y-1}$R$^2$;
$R^{d1}$ is —(CH$_2$)$_x$R$^1$;
$R^{e1}$ is —(CH$_2$)$_y$R$^2$; and
$R^{f1}$ is —(CH$_2$)$_{y-1}$R$^2$;
each $R^1$ and $R^2$ is independently H or unsubstituted alkyl;
each x and y is independently an integer greater than or equal to 1; and
the cycloalkane having the structure of formula (X-I) is:

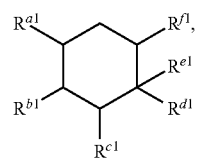

(X-I)

wherein $R^{a1}$, $R^{b1}$, $R^{c1}$, $R^{d1}$, $R^{e1}$, and $R^{f1}$ are as defined for formula (I) above.

In other embodiments, a cyclic ketone having a structure of formula (II) may be hydrodeoxygenated to form a cycloalkane having a structure of formula (X-II), wherein:
the cyclic ketone having the structure of formula (II) is:

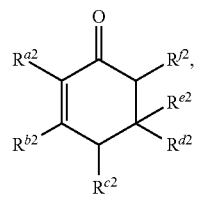

(II)

wherein:
$R^{a2}$ is —(CH$_2$)$_{y-1}$R$^2$;
$R^{b2}$ is —(CH$_2$)$_x$R$^1$;
$R^{c2}$ is —(CH$_2$)$_{y-1}$R$^2$;
$R^{d2}$ is —(CH$_2$)$_x$R$^1$;
$R^{e2}$ is —(CH$_2$)$_y$R$^2$; and
$R^{f2}$ is —(CH$_2$)$_{x-1}$R$^1$;
each $R^1$ and $R^2$ is independently H or unsubstituted alkyl; and
each x and y is independently an integer greater than or equal to 1; and the cycloalkane having the structure of formula (X-II) is:

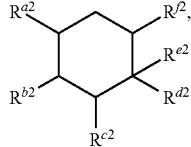
(X-II)

wherein $R^{a2}$, $R^{b2}$, $R^{c2}$, $R^{d2}$, $R^{e2}$, and $R^{f2}$ are as defined for formula (II) above.

In yet other embodiments, a cyclic ketone having a structure of formula (III) may be hydrodeoxygenated to form a cycloalkane having a structure of formula (X-III), wherein: the cyclic ketone having the structure of formula (III) is:

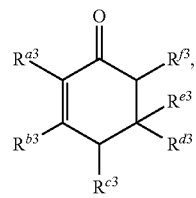
(III)

wherein:
$R^{a3}$ is $-(CH_2)_{x-1}R^1$;
$R^{b3}$ is $-(CH_2)_y R^2$;
$R^{c3}$ is $-(CH_2)_{x-1}R^1$;
$R^{d3}$ is $-(CH_2)_x R^1$;
$R^{e3}$ is $-(CH_2)_y R^2$; and
$R^{f3}$ is $-(CH_2)_{y-1}R^2$;
each $R^1$ and $R^2$ is independently H or unsubstituted alkyl; and
each x and y is independently an integer greater than or equal to 1;
the cycloalkane having the structure of formula (X-III) is:

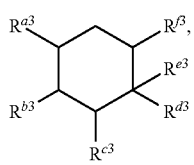
(X-III)

wherein $R^{a3}$, $R^{b3}$, $R^{c3}$, $R^{d3}$, $R^{e3}$, and $R^{f3}$ are as defined for formula (III) above.

In other embodiments, a cyclic ketone having a structure of formula (IV) may be hydrodeoxygenated to form a cycloalkane having a structure of formula (X-IV), wherein: the cyclic ketone having the structure of formula (IV) is:

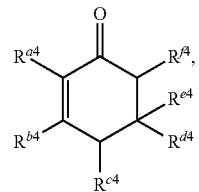
(IV)

wherein:
$R^{a4}$ is $-(CH_2)_{y-1}R^2$;
$R^{b4}$ is $-(CH_2)_y R^2$;
$R^{c4}$ is $-(CH_2)_{x-1}R^1$;
$R^{d4}$ is $-(CH_2)_x R^1$;
$R^{e4}$ is $-(CH_2)_y R^2$; and
$R^{f4}$ is $-(CH_2)_{x-1}R^1$;
each $R^1$ and $R^2$ is independently H or unsubstituted alkyl; and
each x and y is independently an integer greater than or equal to 1; and
the cycloalkane having the structure of formula (X-IV) is:

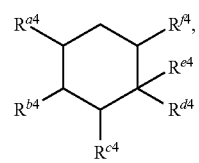
(X-IV)

wherein $R^{a4}$, $R^{b4}$, $R^{c4}$, $R^{d4}$, $R^{e4}$, and $R^{f4}$ are as defined for formula (IV) above.

Acyclic Alkanes

The acyclic ketones having the structure of formula (L-I) or (L-II) can be hydrodeoxygenated to form their respective alkanes.

For example, in some embodiments, an acyclic ketone having a structure of formula (L-I) or (L-II) may be hydrodeoxygenated to form an alkane having a structure of formula (X-L-I) or (X-L-II), respectively, wherein:
the acyclic ketone having a structure of formula (L-I) or (L-II) is:

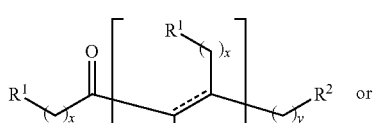
(L-I)

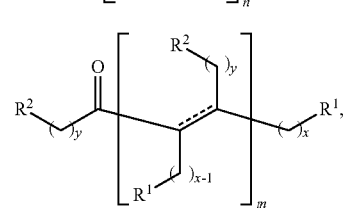
(L-II)

or any isomers thereof, wherein:
each $R^1$ and $R^2$ is independently H or unsubstituted alkyl;
each x and y is independently an integer greater than or equal to 1;

n and m are each an integer greater than or equal to 1, and
the dotted line represents a single bond when a hydrogen source (e.g., $H_2$ or an alcohol) is present, and a double bond when a hydrogen source is absent; and the alkane having the structure of formula (X-L-I) or (X-L-II) is:

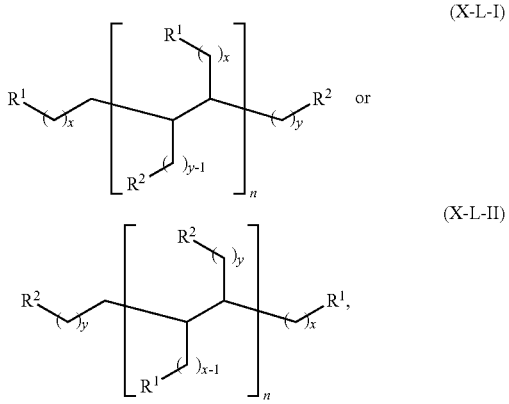

wherein $R^1$, $R^2$, x and y are as defined for the ketone having the structure of formula (L-I-1) or (L-II-1), respectively.

Uses of the Cyclic and Acyclic Alkanes

The cycloalkanes having the structure of formula (X-I), (X-II), (X-III) or (X-IV) that have one or more of the following properties are suitable for use as jet fuels or diesel:
(i) pour point of less than −70° C.;
(ii) freezing point of less than −45° C.; and
(iii) boiling range of between 175° C. and 275° C.

The cycloalkanes having the structure of formula (X-I), (X-II), (X-III) or (X-IV) that have one or more of the following properties are suitable for use as lubricants:
(i) pour point of less than −20° C.;
(ii) viscosity index (VI) of greater than 40;
(v) TGA Noack of less than 30%; and
(vi) DSC oxidation of greater than 180° C.

One of skill in the art would recognize suitable methods or techniques to determine the properties listed above. For example, the properties described above may be performed in accordance with ASTM International standards.

Definitions

"Aliphatic" refers to a linear or branched hydrocarbon structure, and can be saturated or have any degree of unsaturation. Aliphatic groups include, for example, alkyl, alkenyl, and alkynyl. In some embodiments, aliphatic as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 1 to 20 carbon atoms (i.e., $C_{1-20}$ aliphatic), 1 to 15 carbon atoms (i.e., $C_{1-15}$ aliphatic), 1 to 10 carbon atoms (i.e., $C_{1-10}$ aliphatic), 1 to 9 carbon atoms (i.e., $C_{1-9}$ aliphatic), 1 to 8 carbon atoms (i.e., $C_{1-8}$ aliphatic), 1 to 7 carbon atoms (i.e., $C_{1-7}$ aliphatic), 1 to 6 carbon atoms (i.e., $C_{1-6}$ aliphatic), 1 to 5 carbon atoms (i.e., $C_{1-5}$ aliphatic), 1 to 4 carbon atoms (i.e., $C_{1-4}$ aliphatic), 1 to 3 carbon atoms (i.e., $C_{1-3}$ aliphatic), or 1 to 2 carbon atoms (i.e., $C_{1-2}$ aliphatic).

"Alkyl" refers to a linear or branched saturated hydrocarbon chain. Examples of alkyl groups include methyl, ethyl, n-propyl, iso-propyl, n-butyl, sec-butyl, tert-butyl, n-pentyl, 2-pentyl, iso-pentyl, neo-pentyl, hexyl, 2-hexyl, 3-hexyl, and 3-methylpentyl. When an alkyl residue having a specific number of carbons is named, all geometric isomers having that number of carbons may be encompassed; thus, for example, "butyl" can include n-butyl, sec-butyl, iso-butyl and tert-butyl; "propyl" can include n-propyl and iso-propyl. In some embodiments, alkyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 1 to 20 carbon atoms (i.e., $C_{1-20}$ alkyl), 1 to 15 carbon atoms (i.e., $C_{1-15}$ alkyl), 1 to 10 carbon atoms (i.e., $C_{1-10}$ alkyl), 1 to 9 carbon atoms (i.e., $C_{1-9}$ alkyl), 1 to 8 carbon atoms (i.e., $C_{1-8}$ alkyl), 1 to 7 carbon atoms (i.e., $C_{1-7}$ alkyl), 1 to 6 carbon atoms (i.e., $C_{1-6}$ alkyl), 1 to 5 carbon atoms (i.e., $C_{1-5}$ alkyl), 1 to 4 carbon atoms (i.e., $C_{1-4}$ alkyl), 1 to 3 carbon atoms (i.e., $C_{1-3}$ alkyl), 1 to 2 carbon atoms (i.e., $C_{1-2}$ alkyl), or 1 carbon atom (i.e., $C_1$ alkyl).

"Alkenyl" refers to a linear or branched hydrocarbon chain with one or more double bonds. In some embodiments, alkenyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 2 to 20 carbon atoms (i.e., $C_{2-20}$ alkenyl), 2 to 15 carbon atoms (i.e., $C_{2-15}$ alkenyl), 2 to 10 carbon atoms (i.e., $C_{2-10}$ alkenyl), 2 to 10 carbon atoms (i.e., $C_{2-9}$ alkenyl), 2 to 8 carbon atoms (i.e., $C_{2-8}$ alkenyl), 2 to 7 carbon atoms (i.e., $C_{2-7}$ alkenyl), 2 to 6 carbon atoms (i.e., $C_{2-6}$ alkenyl), 2 to 5 carbon atoms (i.e., $C_{2-5}$ alkenyl), 2 to 4 carbon atoms (i.e., $C_{2-4}$ alkenyl), 2 or 3 carbon atoms (i.e., $C_{2-3}$ alkenyl).

"Alkynyl" refers to a linear or branched hydrocarbon chain with one or more triple bonds. In some embodiments, alkynyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 2 to 20 carbon atoms (i.e., $C_{2-20}$ alkynyl), 2 to 15 carbon atoms (i.e., $C_{2-15}$ alkynyl), 2 to 10 carbon atoms (i.e., $C_{2-10}$ alkynyl), 2 to 10 carbon atoms (i.e., $C_{2-9}$ alkynyl), 2 to 8 carbon atoms (i.e., $C_{2-8}$ alkynyl), 2 to 7 carbon atoms (i.e., $C_{2-7}$ alkynyl), 2 to 6 carbon atoms (i.e., $C_{2-6}$ alkynyl), 2 to 5 carbon atoms (i.e., $C_{2-5}$ alkynyl), 2 to 4 carbon atoms (i.e., $C_{2-4}$ alkynyl), 2 or 3 carbon atoms (i.e., $C_{2-3}$ alkynyl).

"Alicyclyl" refers to a cyclic aliphatic group, including cycloalkyl, cycloalkenyl, or cycloalkynyl. An alicyclic group can comprise one or more rings, includes fused and bridged groups, and can be saturated or have any degree of unsaturation. In some embodiments, alicyclic group as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has from 3 to 20 ring carbon atoms (i.e., $C_{3-20}$ alicyclic group), 3 to 15 ring carbon atoms (i.e., $C_{3-15}$ alicyclic group), 3 to 10 ring carbon atoms (i.e., $C_{3-10}$ alicyclic group), or 3 to 9 ring carbon atoms (i.e., $C_{3-9}$ alicyclic group), 3 to 8 ring carbon atoms (i.e., $C_{3-8}$ alicyclic group), 3 to 7 ring carbon atoms (i.e., $C_{3-7}$ alicyclic group), 3 to 6 ring carbon atoms (i.e., $C_{3-6}$ alicyclic group), or 5 ring carbon atoms (i.e., $C_5$ alicyclic group), or 6 ring carbon atoms (i.e., $C_6$ alicyclic group).

"Cycloalkyl" refers to a cyclic alkyl group. Examples of cycloalkyl groups include cyclopropyl, cyclobutyl, cyclopentyl, and cyclohexyl. In some embodiments, cycloalkyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has from 3 to 20 ring carbon atoms (i.e., $C_{3-20}$ cycloalkyl), 3 to 15 ring carbon atoms (i.e., $C_{3-15}$ cycloalkyl), 3 to 10 ring carbon atoms (i.e., $C_{3-10}$ cycloalkyl), or 3 to 9 ring carbon atoms (i.e., $C_{3-9}$ cycloalkyl), 3 to 8 ring carbon atoms (i.e., $C_{3-8}$ cycloalkyl), 3 to 7 ring carbon atoms (i.e., $C_{3-7}$ cycloalkyl), 3 to 6 ring carbon atoms (i.e., $C_{3-6}$ cycloalkyl), or 5 ring carbon atoms (i.e., $C_5$ cycloalkyl), or 6 ring carbon atoms (i.e., $C_6$ cycloalkyl).

"Heterocyclyl" refer to a cyclic aliphatic group with one or more ring heteroatoms independently selected from nitrogen, oxygen and sulfur. Heterocyclyl includes, for example, heterocycloalkyl, heterocycloalkenyl, and heterocycloalkynyl. Heterocycles can be group can comprise one or more rings, include fused and bridged groups, and can be saturated or have any degree of unsaturation. In some embodiments, the heterocyclyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 2 to 20 ring carbon atoms (i.e., $C_{2-20}$ heterocyclyl), 2 to 15 ring carbon atoms (i.e., $C_{2-15}$ heterocyclyl), 2 to 12 ring carbon atoms (i.e., $C_{2-12}$ heterocyclyl), 2 to 10 ring carbon atoms (i.e., $C_{2-10}$ heterocyclyl), or 2 to 8 ring carbon atoms (i.e., $C_{2-8}$ heterocyclyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen.

"Heterocycloalkyl" refers to a cyclic alkyl group, with one or more ring heteroatoms independently selected from nitrogen, oxygen and sulfur. In one example, a heterocycloalkyl has 2 to 8 ring carbon atoms, with 1 to 3 ring heteroatoms independently selected from nitrogen, oxygen and sulfur. Examples of heterocycloalkyl groups may include pyrrolidinyl, piperidinyl, piperazinyl, oxetanyl, dioxolanyl, azetidinyl, and morpholinyl. In some embodiments, the heterocycloalkyl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 2 to 20 ring carbon atoms (i.e., $C_{2-20}$ heterocycloalkyl), 2 to 15 ring carbon atoms (i.e., $C_{2-15}$ heterocycloalkyl), 2 to 10 ring carbon atoms (i.e., $C_{2-10}$ heterocycloalkyl), 2 to 12 ring carbon atoms (i.e., $C_{2-12}$ heterocycloalkyl), or 2 to 8 ring carbon atoms (i.e., $C_{2-8}$ heterocycloalkyl); and 1 to 5 ring heteroatoms, 1 to 4 ring heteroatoms, 1 to 3 ring heteroatoms, 1 or 2 ring heteroatoms, or 1 ring heteroatom independently selected from nitrogen, sulfur or oxygen.

"Aryl" refers to an aromatic carbocyclic group having a single ring (e.g., phenyl), multiple rings (e.g., biphenyl), or multiple fused rings (e.g., naphthyl, fluorenyl, and anthryl). In certain embodiments, aryl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 5 to 20 ring carbon atoms (i.e., $C_{5-20}$ aryl), or 5 to 12 carbon ring atoms (i.e., $C_{5-12}$ aryl), 6 to 20 ring carbon atoms (i.e., $C_{6-20}$ aryl), or 6 to 12 carbon ring atoms (i.e., $C_{6-12}$ aryl). Aryl, however, does not encompass or overlap in any way with heteroaryl, separately defined below. In certain embodiments, if one or more aryl groups are fused with a heteroaryl ring, the resulting ring system is heteroaryl.

"Heteroaryl" refers to an aromatic group having a single ring, multiple rings, or multiple fused rings, with one or more ring heteroatoms independently selected from nitrogen, oxygen, and sulfur. In some embodiments, heteroaryl is an aromatic, monocyclic or bicyclic ring containing one or more heteroatoms independently selected from nitrogen, oxygen and sulfur with the remaining ring atoms being carbon. Examples of heteroaryl groups include furanyl, pyrrolyl, thiophenyl, imidazolyl, thiazolyl, pyridyl, pyridazinyl, pyrimidinyl, and pyrazolyl. In certain embodiments, heteroaryl as used herein, such as in compounds of formula (A), (A-1), (B), (B-1), (C), (I), (II), (III), (IV), (L-I), (L-II), (L-I-1), (L-II-1), (L-I-2), (L-II-2), (M-I), (M-II), (N-I), (N-II), (N-III), (X-I), (X-II), (X-III), (X-IV), (X-L-I) and (X-L-II), has 3 to 20 ring carbon atoms (i.e., $C_{3-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 or 2 ring heteroatoms, or 1 ring heteroatom independently selected from nitrogen, oxygen, and sulfur. In one example, a heteroaryl has 3 to 8 ring carbon atoms, with 1 to 3 ring heteroatoms independently selected from nitrogen, oxygen and sulfur. Heteroaryl does not encompass or overlap with aryl as defined above.

It should be understood that reference to "between" two values or parameters herein includes (and describes) embodiments that include those two values or parameters per se. For example, description referring to "between x and y" includes description of "x" and "y" per se.

ENUMERATED EMBODIMENTS

The following enumerated embodiments are representative of some aspects of the invention.

1. A method for producing at least one cyclic ketone, comprising:

contacting at least one ketone independently having a structure of formula (A) with catalyst to form a reaction mixture, wherein the contacting of the at least one ketone with the catalyst produces at least one cyclic ketone having a structure of formula (I), (II), (III) or (IV), or any isomers thereof, from at least a portion of the at least one ketone, wherein:

the at least one ketone independently having the structure of formula (A) is:

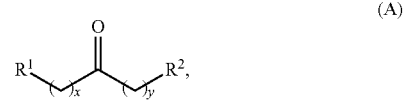

(A)

wherein:
each $R^1$ and $R^2$ is independently H, unsubstituted alkyl, substituted alkyl, —C(R^t)_3, —CH(R^t)_2, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;

each x and y is independently an integer greater than or equal to 1, provided that when x and y are both 1, either $R^1$ or $R^2$ is other than H;

the cyclic ketone having the structure of formula (I) is:

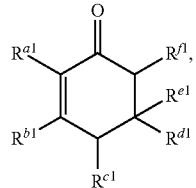

(I)

or any isomers thereof, wherein:
$R^{a1}$ is $—(CH_2)_{x-1}R^1$;
$R^{b1}$ is $—(CH_2)_xR^1$;
$R^{c1}$ is $—(CH_2)_{y-1}R^2$;
$R^{d1}$ is $—(CH_2)_xR^1$;
$R^{e1}$ is $—(CH_2)_yR^2$; and
$R^{f1}$ is $—(CH_2)_{y-1}R^2$;

the cyclic ketone having the structure of formula (II) is:

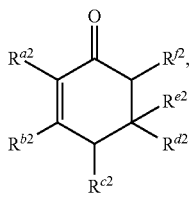

(II)

or any isomers thereof, wherein:
$R^{a2}$ is $—(CH_2)_{y-1}R^2$;
$R^{b2}$ is $—(CH_2)_xR^1$;
$R^{c2}$ is $—(CH_2)_{y-1}R^2$;
$R^{d2}$ is $—(CH_2)_xR^1$;
$R^{e2}$ is $—(CH_2)_yR^2$; and
$R^{f2}$ is $—(CH_2)_{x-1}R^1$;

the cyclic ketone having the structure of formula (III) is:

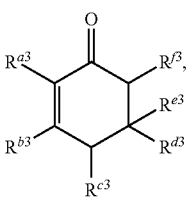

(III)

or any isomers thereof, wherein:
$R^{a3}$ is $—(CH_2)_{x-1}R^1$;
$R^{b3}$ is $—(CH_2)_yR^2$;
$R^{c3}$ is $—(CH_2)_{x-1}R^1$;
$R^{d3}$ is $—(CH_2)_xR^1$;
$R^{e3}$ is $—(CH_2)_yR^2$; and
$R^{f3}$ is $—(CH_2)_{y-1}R^2$;

the cyclic ketone having the structure of formula (IV) is:

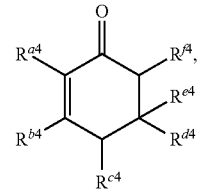

(IV)

or any isomers thereof, wherein:
$R^{a4}$ is $—(CH_2)_{y-1}R^2$;
$R^{b4}$ is $—(CH_2)_yR^2$;
$R^{c4}$ is $—(CH_2)_{x-1}R^1$;
$R^{d4}$ is $—(CH_2)_xR^1$;
$R^{e4}$ is $—(CH_2)_yR^2$; and
$R^{f4}$ is $—(CH_2)_{x-1}R^1$.

2. The method of embodiment 1, wherein the contacting of the at least one ketone with the catalyst further produces water as the at least one cyclic ketone is produced, and the method further comprises controlling the amount of water present in the reaction mixture.

3. The method of embodiment 2, wherein controlling the amount of water present in the reaction mixture comprises removing at least a portion of the water present in the reaction mixture.

4. The method of embodiment 2 or 3, wherein the amount of water present in the reaction mixture is less than 5 wt %.

5. A method for producing at least one cycloalkane, comprising hydrodeoxygenating at least one cyclic ketone having a structure of formula (I), (II), (III) or (IV), or any isomers thereof, produced according to the method of embodiments 1 to 5 to produce at least one cycloalkane.

6. A method for producing at least one acyclic ketone, comprising contacting at least one ketone having a structure of formula (A) with catalyst in the presence of $H_2$ or at least one secondary alcohol to produce at least one acyclic ketone having a structure of formula (L-I) or (L-II), wherein:

the at least one ketone having the structure of formula (A) is:

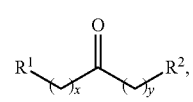

(A)

wherein:
$R^1$ is H, unsubstituted alkyl, substituted alkyl, $—C(R^t)_3$, $—CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, $R^2$ is unsubstituted alkyl, substituted alkyl, $—C(R^t)_3$, $—CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl, each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;

x is an integer greater than or equal to 1;
y is an integer greater than or equal to 0; and the at least one acyclic ketone having the structure of formula (L-I) or (L-II) is:

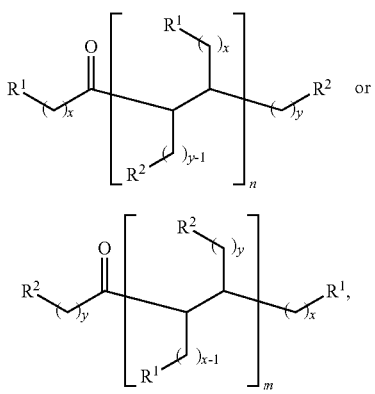

wherein:
R¹, R², x and y are as defined for formula (A), and
n and m are each an integer greater than or equal to 1.

7. The method of embodiment 6, wherein the at least one secondary alcohol independently has the structure of formula (B):

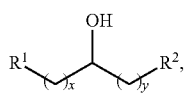

wherein:
each $R^1$ and $R^2$ is independently H, unsubstituted alkyl, substituted alkyl, —C(R')$_3$, —CH(R')$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^r$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1.

8. A method for producing at least one acyclic ketone, comprising contacting at least one alcohol independently having a structure of formula (B) with catalyst to produce at least one acyclic ketone having a structure of formula (L-I) or (L-II), wherein:
the catalyst is heterogeneous metal catalyst;
the at least one alcohol independently having the structure of formula (B) is:

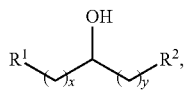

wherein:
each $R^1$ and $R^2$ is independently H, unsubstituted alkyl, substituted alkyl, —C(R')$_3$, —CH(R')$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^r$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1; and
the at least one acyclic ketone having the structure of formula (L-I) or (L-II) are:

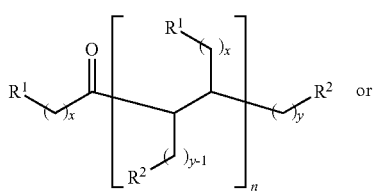

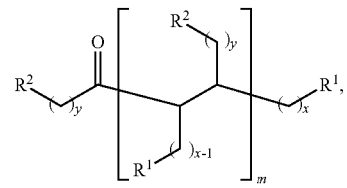

wherein:
R¹, R², x and y are as defined for formula (B), and
n and m are each an integer greater than or equal to 1.

9. The method of any one of embodiments 6 to 8, wherein the catalyst comprises at least one metal and a basic support.
10. The method of embodiment 9, wherein at least one metal is a transition metal.
11. The method of embodiment 10, wherein at least one metal is palladium, copper, or palladium-copper alloy.
12. The method of any one of embodiments 1 to 11, wherein the catalyst is solid.
13. The method of any one of embodiments 1 to 12, wherein the catalyst is basic.
14. The method of any one of embodiments 1 to 12, wherein the catalyst has one or more of the following properties:
(i) a pKa between 8 to 16;
(ii) a CO$_2$ desorption of at least 50° C., wherein CO$_2$ desorption is carried out by adsorbing CO$_2$ to the catalyst at room temperature and heating up to 773 K;
(iii) at least one basic oxygen atom; and
(iv) a proton affinity of at least 700 kJ/mol.
15. The method of any one of embodiments 1 to 12, wherein the catalyst comprises:
a hydrotalcite;
a zeolite;
a metal oxide;
a non-metal oxide;
a supported alkali metal ion;
an apatite;
a sepiolite;
a chrysotile;

a mesoporous silica;
an ionic liquid supported metal oxide;
an aluminophosphate;
a synthetic talc; or
a non-oxide supported on alumina,
or any combinations thereof.

16. The method of any one of embodiments 1 to 12, wherein the catalyst comprises an alkali oxide, an alkaline earth oxide, a non-metal oxide, a transition metal oxide, or a rare metal oxide, or any combinations thereof.

17. The method of any one of embodiments 1 to 12, wherein the catalyst comprises an alkali oxide, an alkaline earth oxide, a rare metal oxide, or any combinations thereof.

18. The method of any one of embodiments 1 to 12, wherein the catalyst comprises Mg, Ti, Sr, Ca, Si, Al, La, Zr, Na or K, or any combinations thereof.

19. The method of any one of embodiments 1 to 12, wherein the catalyst comprises: MgO, SrO, BaO, CaO, ZnO, $La_2O_3$, $TiO_2$, $ZrO_2$, $Al_2O_3$, $Ta_2O_5$, Mn oxide, Cr oxide, Y oxide, $Nb_2O_3$, Mo oxide, W oxide, $ThO_2$, $HfO_2$, $CeO_2$, Yb oxide, $Sc_2O_3$, $V_2O_5$, or other alkali-doped variations thereof;

Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite;

NaY zeolite, NaX zeolite, KY zeolite, RbY zeolite, CsY zeolite, KX zeolite, RbX zeolite, CsX zeolite, palladium/NaY zeolite, palladium/$NH_4$-β zeolite, potassium oxide supported on zeolite Y, lanthanide imide on zeolite, or nitride on zeolite;

$Cs_2CO_3$ or KOH impregnated on a hydrotalcite or a zeolite;
ionic liquid impregnated on MgO;
$Cs_2O$, MgO, $TiO_2$, $ThO_2$, $ZrO_2$, ZnO, or $La_2O_3$;
Na/$SiO_2$ Pd/Na/$SiO_2$, Na/Ca/$SiO_2$, Na/Ca/$SiO_2$, or Cs/$SiO_2$;
hydroxyapatite, fluorapatite, or tert-butoxyapatite;
sepiolite;
$Mg_3(OH)_4Si_4O_5$, or cobalt(II)-substituted chrysotile;
an amino-functionalized mesoporous silica (MCM-41);
a modified mesoporous silica (SBA-15);
ionic liquid supported MgO;
amorphous aluminophosphate (ALPO);
a magnesium organo silicate; or
KF supported on alumina, or
any combinations thereof.

20. The method of any one of embodiments 1 to 12, wherein the catalyst comprises $Ta_2O_5$ impregnated on a modified mesoporous silica.

21. The method of embodiment 20, wherein the modified mesoporous silica is SBA-15.

22. The method of any one of embodiments 1 to 12, wherein the catalyst comprises a hydrotalcite.

23. The method of embodiment 22, wherein the hydrotalcite is calcined.

24. The method of embodiment 22 or 23, wherein the hydrotalcite is Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite, or any combinations thereof.

25. The method of embodiment 24, wherein the hydrotalcite is MgAlO.

26. The method of any one of embodiments 1 to 25, wherein the catalyst has 0.25 mol % to 2 mol % basic sites.

27. The method of any one of embodiments 1 to 12, wherein the catalyst is acidic.

28. The method of any one of embodiments 1 to 12, wherein the catalyst is amphoteric.

29. The method of any one of embodiments 1 to 12, wherein the catalyst is selected from the group consisting of Pd/C, Pd/HT, Cu/HT, Pd—Cu/HT, KF/$Al_2O_3$, calcined hydrotalcite, MgO, $TiO_2$, $ZrO_2$, Zr—Ti—O, Mg—Zr—O, $SrTiO_3$, $La_2O_3$, LaAlMgO, $SiO_2$—NHMe, $SiO_2$—$NHMe_2$, $SiO_2$—$Al_2O_3$, and hydroxyapatite, or any combinations thereof.

30. The method of any one of embodiments 1 to 29, wherein when x and y are both 1, either $R^1$ or $R^2$ is unsubstituted alkyl.

31. The method of any one of embodiments 1 to 29, wherein when x and y are both 1, $R^1$ is unsubstituted alkyl, and $R^2$ is H.

32. The method of any one of embodiments 1 to 29, wherein:
$R^1$ is:
H,
unsubstituted phenyl,
unsubstituted furan,
furan substituted with alkyl, or
—CH($R^r$)$_2$, wherein $R^r$ are each independently unsubstituted furan or furan substituted with alkyl;
$R^2$ is H.

33. The method of any one of embodiments 1 to 29, wherein each $R^1$ and $R^2$ is H or unsubstituted alkyl.

34. The method of any one of embodiments 1 to 7, 12 to 29, wherein at least one of the ketones independently having the structure of formula (A) is a ketone having the structure of formula (A-1):

(A-1)

wherein x is an integer greater than or equal to 2.

35. The method of any one of embodiments 8 to 29, wherein at least one of the alcohols independently having the structure of formula (B) is an alcohol having the structure of formula (B-1):

(B-1)

wherein x is an integer greater than or equal to 1.

36. The method of embodiment 34 or 35, wherein $R^1$ is H or unsubstituted alkyl.

37. The method of any one of embodiments 1 to 36, wherein x is 3 to 45.

38. The method of embodiment 37, wherein x is 3 to 21.

39. The method of any one of embodiments 1 to 38, wherein x is 3, 5, 7 or 9.

40. The method of any one of embodiments 1 to 7, 12 to 29, wherein at least one ketone having the structure of formula (A) is selected from the group consisting of

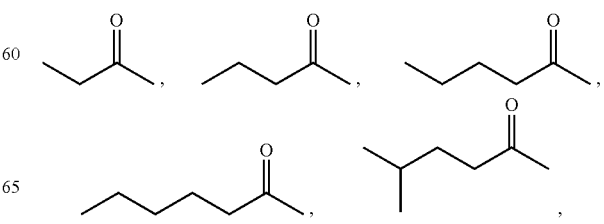

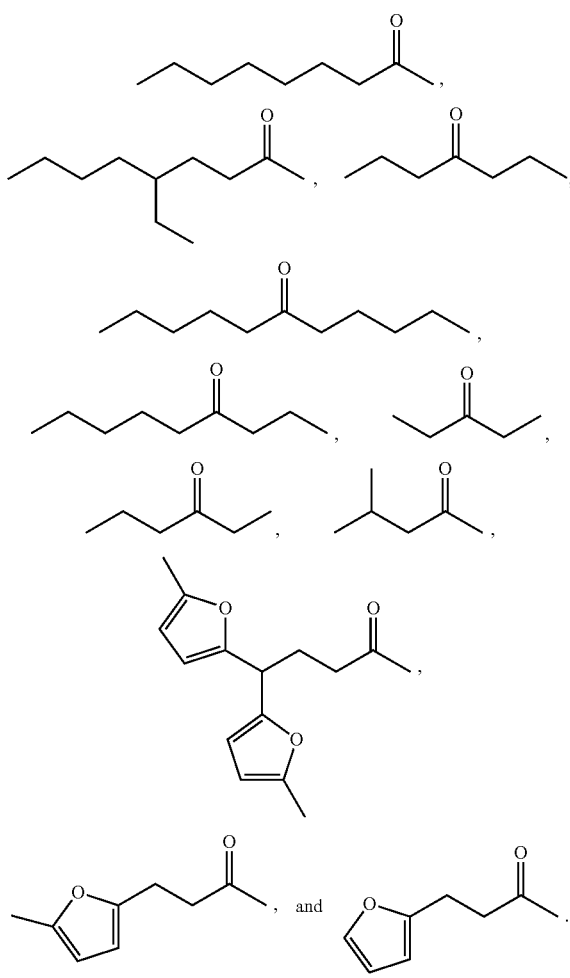

41. The method of any one of embodiments 1 to 7, 12 to 29, wherein at least one ketone having the structure of formula (A) is selected from the group consisting of:

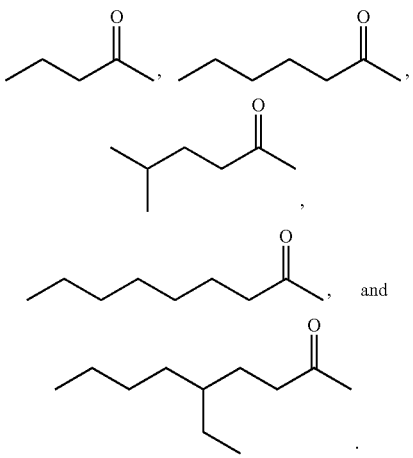

42. The method of any one of embodiments 8 to 29, wherein at least one alcohol having the structure of formula (B) is selected from the group consisting of:

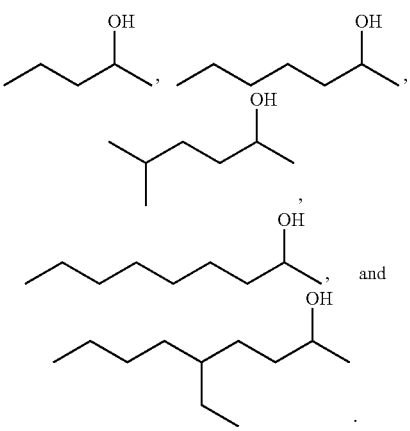

43. A method for producing at least one alkane, comprising: hydrodeoxygenating at least one acyclic ketone having the structure of formula (L-I) or (L-II) produced according to the method of any one of embodiments 8 to 29 to produce at least one alkane.

44. A composition, comprising:
at least one ketone independently having the structure of formula (A):

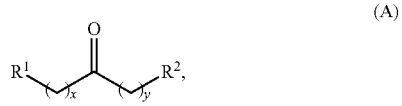

(A)

wherein:
each $R^1$ and $R^2$ is independently H, unsubstituted alkyl, substituted alkyl, —C($R^r$)$_3$, —CH($R^r$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^r$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1, provided that when x and y are both 1, either $R^1$ or $R^2$ is other than H;
a catalyst; and
water.

45. The composition of embodiment 44, wherein the amount of water present in the composition is less than 5 wt %.

46. The composition of embodiment 44, wherein the composition further comprises a hydrogen source.

47. A composition, comprising:
at least one alcohol having a structure of formula (B):

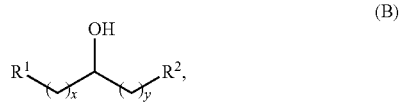

(B)

wherein:
each $R^1$ and $R^2$ is independently H, unsubstituted alkyl, substituted alkyl, —C($R^r$)$_3$, —CH($R^r$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each $R^r$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1;
a catalyst, wherein the catalyst is heterogeneous.

48. The composition of any one of embodiments 44 to 47, wherein the catalyst is solid.

49. The composition of any one of embodiments 44 to 47, wherein the catalyst is basic.

50. The composition of any one of embodiments 44 to 47, wherein the catalyst has one or more of the following properties:
(i) a pKa between 8 to 16;
(ii) a $CO_2$ desorption of at least 50° C., wherein $CO_2$ desorption is carried out by adsorbing $CO_2$ to the catalyst at room temperature and heating up to 773 K;
(iii) at least one basic oxygen atom; and
(iv) a proton affinity of at least 700 kJ/mol.

51. The composition of any one of embodiments 44 to 47, wherein the catalyst comprises:
a hydrotalcite;
a zeolite;
a metal oxide;
a non-metal oxide;
a supported alkali metal ion;
an apatite;
a sepiolite;
a chrysotile;
a mesoporous silica;
an ionic liquid supported metal oxide;
an aluminophosphate;
a synthetic talc; or
a non-oxide supported on alumina,
or any combinations thereof.

52. The composition of any one of embodiments 44 to 47, wherein the catalyst comprises an alkali oxide, an alkaline earth oxide, a non-metal oxide, a transition metal oxide, or a rare metal oxide, or any combinations thereof.

53. The composition of any one of embodiments 44 to 47, wherein the catalyst comprises an alkali oxide, an alkaline earth oxide, a rare metal oxide, or any combinations thereof.

54. The composition of any one of embodiments 44 to 47, wherein the catalyst comprises Mg, Ti, Sr, Ca, Si, Al, La, Zr, Na or K, or any combinations thereof.

55. The composition of any one of embodiments 44 to 47, wherein the catalyst comprises:
MgO, SrO, BaO, CaO, ZnO, $La_2O_3$, $TiO_2$, $ZrO_2$, $Al_2O_3$, $Ta_2O_5$, Mn oxide, Cr oxide, Y oxide, $Nb_2O_3$, Mo oxide, W oxide, $ThO_2$, $HfO_2$, $CeO_2$, Yb oxide, $Sc_2O_3$, $V_2O_5$, or other alkali-doped variations thereof;
Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite;
NaY zeolite, NaX zeolite, KY zeolite, RbY zeolite, CsY zeolite, KX zeolite, RbX zeolite, CsX zeolite, palladium/NaY zeolite, palladium/$NH_4$-β zeolite, potassium oxide supported on zeolite Y, lanthanide imide on zeolite, or nitride on zeolite;
$Cs_2CO_3$ or KOH impregnated on a hydrotalcite or a zeolite;
ionic liquid impregnated on MgO;
$Cs_2O$, MgO, $TiO_2$, $ThO_2$, $ZrO_2$, ZnO, or $La_2O_3$;
Na/$SiO_2$ Pd/Na/$SiO_2$, Na/Ca/$SiO_2$, Na/Ca/$SiO_2$, or Cs/$SiO_2$;
hydroxyapatite, fluorapatite, or tert-butoxyapatite;
sepiolite;
$Mg_3(OH)_4Si_4O_5$, or cobalt(II)-substituted chrysotile;
an amino-functionalized mesoporous silica (MCM-41);
a modified mesoporous silica (SBA-15);
ionic liquid supported MgO;
amorphous aluminophosphate (ALPO);
a magnesium organo silicate; or
KF supported on alumina, or
any combinations thereof.

56. The composition of any one of embodiments 44 to 47, wherein the catalyst comprises $Ta_2O_5$ impregnated on a modified mesoporous silica.

57. The composition of embodiment 56, wherein the modified mesoporous silica is SBA-15.

58. The composition of any one of embodiments 44 to 47, wherein the catalyst comprises a hydrotalcite.

59. The composition of any one of embodiments 44 to 47, wherein the hydrotalcite is calcined.

60. The composition of embodiment 58 or 59, wherein the hydrotalcite is Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite, or any combinations thereof.

61. The composition of embodiment 60, wherein the hydrotalcite is MgAlO.

62. The composition of any one of embodiments 44 to 47, wherein the catalyst has 0.25 mol % to 2 mol % basic sites.

63. The composition of any one of embodiments 44 to 47, wherein the catalyst is acidic.

64. The composition of any one of embodiments 44 to 47, wherein the catalyst is amphoteric.

65. The composition of any one of embodiments 44 to 47, wherein the catalyst is selected from the group consisting of Pd/C, Pd/HT, Cu/HT, Pd—Cu/HT, KF/$Al_2O_3$, calcined hydrotalcite, MgO, $TiO_2$, $ZrO_2$, Zr—Ti—O, Mg—Zr—O, $SrTiO_3$, $La_2O_3$, LaAlMgO, $SiO_2$—NHMe, $SiO_2$—NHMe$_2$, $SiO_2$—$Al_2O_3$, and hydroxyapatite, or any combinations thereof.

66. The composition of any one of embodiments 44 to 47, wherein the catalyst comprises at least one metal and a basic support.

67. The composition of embodiment 66, wherein at least one metal is a transition metal.

68. The composition of embodiment 67, wherein at least one metal is palladium, copper, or a palladium-copper alloy.

69. The composition of any one of embodiments 44 to 68, wherein when x and y are both 1, either $R^1$ or $R^2$ is unsubstituted alkyl.

70. The composition of any one of embodiments 44 to 68, wherein when x and y are both 1, $R^1$ is unsubstituted alkyl, and $R^2$ is H.

71. The composition of any one of embodiments 44 to 68, wherein:
$R^1$ is:
H,
unsubstituted furan,
furan substituted with alkyl, or —CH(R$^t$)$_2$, wherein R$^t$ are each independently unsubstituted furan or furan substituted with alkyl;
R$^2$ is H.

72. The composition of any one of embodiments 44 to 68, wherein each R$^1$ and R$^2$ is H or unsubstituted alkyl.

73. The composition of any one of embodiments 44 to 68, wherein at least one ketone having the structure of formula (A) is a ketone having the structure of formula (A-1):

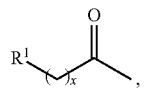

(A-1)

wherein x is an integer greater than or equal to 2.

74. The composition of embodiments 47 to 68, wherein at least one alcohol having the structure of formula (B) is an alcohol having the structure of formula (B-1):

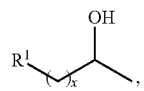

(B-1)

wherein x is an integer greater than or equal to 1.

75. A method for producing at least one aromatic compound, comprising:
contacting at least one ketone independently having a structure of formula (A) with catalyst to form a reaction mixture, wherein the contacting of the at least one ketone with the catalyst produces at least one aromatic compound having a structure of formula (N-I), (N-II), or (N-III), or any isomers thereof, from at least a portion of the at least one ketone, wherein:
the at least one ketone independently having the structure of formula (A) is:

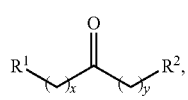

(A)

wherein:
each R$^1$ and R$^2$ is independently H, unsubstituted alkyl, substituted alkyl, —C(R$^t$)$_3$, —CH(R$^t$)$_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
wherein each R$^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
each x and y is independently an integer greater than or equal to 1, provided that when x and y are both 1, either R$^1$ or R$^2$ is other than H;
the aromatic compound having the structure of formula (N-I) is:

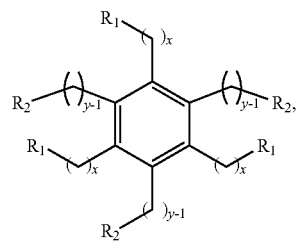

(N-I)

or any isomers thereof;
the aromatic compound having the structure of formula (N-II) is:

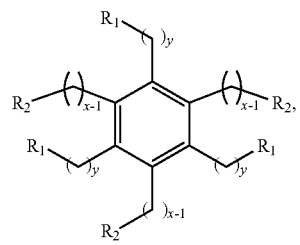

(N-II)

or any isomers thereof; and
the aromatic compound having the structure of formula (N-III) is:

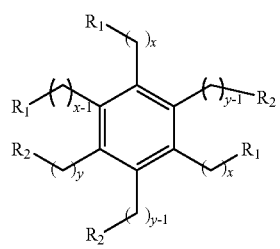

(N-III)

or any isomers thereof.

EXAMPLES

The following Examples are merely illustrative and are not meant to limit any aspects of the present disclosure in any way.

Example 1

Self-condensation of 2-hexanone

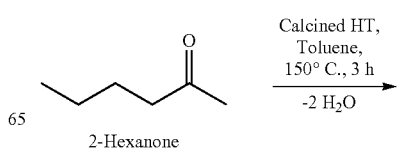

2-Hexanone

-continued

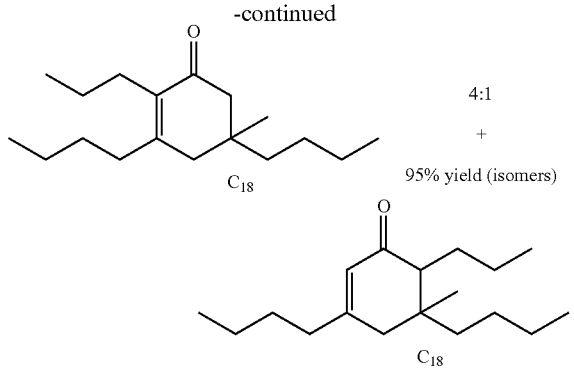

4:1
+
95% yield (isomers)

$C_{18}$ $C_{18}$

This Example demonstrates the formation of cyclic ketones from 2-hexanone using calcined hydrotalcite as the catalyst.

A solution of 2-hexanone (2 mmol) in toluene (3 mL) and calcined hydrotalcite (200 mg) were added to a pressure tube equipped with a magnetic spin bar. The reaction mixture was sealed and stirred (800 rpm) on the pre-heated deck of a stirrer at 150° C. for 3 hours. The reaction mixture was then cooled, and an amount of dodecane was added. The product mixture was then passed through a small plug of silica gel and washed with ethyl acetate (3×10 mL) to remove solid catalyst particles. The crude products in the filtrate were then analyzed as well as quantified using gas chromatography. The reaction was observed to produce cyclic $C_{18}$ compounds (as depicted in the reaction scheme above) in 95% yield of 4:1 isomers.

Catalyst Preparation:

Calcined hydrotalcite (Mg—Al—O) used above was prepared according to the following procedure. Commercially available synthetic hydrotalcite (35 g, $Mg_6Al_2(OH)_{16}CO_3 4H_2O$) was gradually heated (2° C./min) in a static air atmosphere to 700° C. This temperature was maintained constant for additional 2 h, and then the resulting material was cooled to room temperature in a desiccator. The calcined hydrotalcite (Mg—Al mixed oxides) weighed 19.9 g at room temperature (43% weight loss due to the liberation of volatiles from the original material during calcination). It should be understood that unless otherwise stated herein, calcined hydrotalcite used in the Examples are prepared according to this method.

Catalyst Characterization:

Approximately 200 mg of the calcined hydrotalcite prepared above was loaded into a quartz reactor and sealed in the TPD flow system. The calcined hydrotalcite was recalcined in the TPD unit under a 10.0 mL/min He flow following the previously discussed calcination method. After returning to 50° C., temperature was held constant, and a 40 mL/min flow of pure $CO_2$ at atmospheric pressure was used to saturate available basic sites for a period of one hour. Afterwards, the temperature was raised at 10° C./min to 100° C. and all physisorbed $CO_2$ was swept away using a 18.3 mL/min He flow for a period of one hour. At this point, the reactor was cooled to room temperature. The reactor was then heated from room temperature to 1050° C. at 10° C./min and held at 1050° C. for 30 minutes under a constant flow of 18.3 mL/min of He. During this time, desorption of $CO_2$ was measured using a TCD detector. The quantity of $CO_2$ desorbed was standardized using $CaCO_3$ as a reference for $CO_2$ evolution. The catalyst calcined at 700° C. (with a 2 hour hold) was found to have a $CO_2$ TPD of about 95 umol/g. This catalyst was also found to have surface area of $m^2/g$.

Example 2

Catalyst Screening on Oligomerization of 2-hexanone

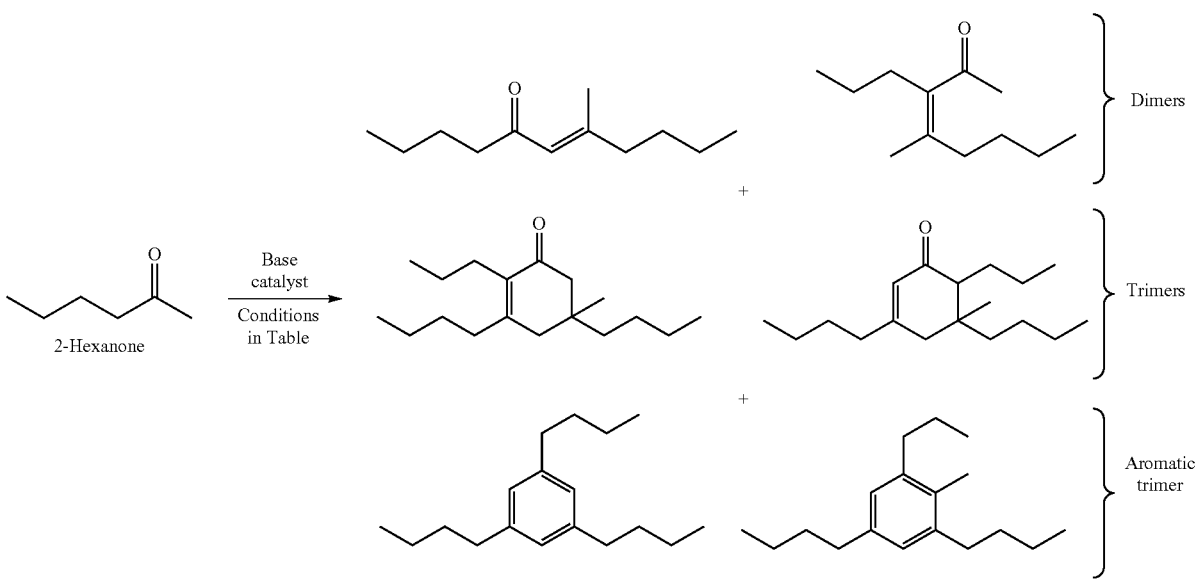

This Example demonstrates the effect of various catalysts on the oligomerization of 2-hexanone.

The reactions of this Example were performed according to the procedure set forth in Example 1 above. Table 1 summarizes the reaction condition and results from the catalyst screen.

TABLE 1

| No | Catalyst | Solvent | Temp. (° C.) | Time (h) | Conv. (%) | Dimer (%) | Trimer (%) | Aromatic (%) | Total (%) |
|---|---|---|---|---|---|---|---|---|---|
| 1 | NaOH (1M) | Water/Toluene | 100 | 10 | 4 | 0 | 0 | 0 | 0 |
| 2 | $KF/Al_2O_3$ (5 mol %) | Toluene | 100 | 15 | 35 | 21 | 13 | 0 | 34 |
| 3 | $KF/Al_2O_3$ (25 mol %) | Toluene | 100 | 15 | 82 | 9 | 68 | 1 | 72 |
| 4 | Calcined HT(200 mg) | Toluene | 150 | 3 | 100 | 0 | 93 | 0 | 93 |
| 5 | Calcined HT(100 mg) | Toluene | 150 | 3 | 100 | 0 | 92 | 0 | 92 |
| 6 | Calcined HT(50 mg) | Toluene | 150 | 3 | 96 | 3 | 86 | 0 | 89 |
| 7 | Calcined HT(200 mg) | Toluene | 120 | 3 | 35 | 20 | 9 | 0 | 29 |
| 8 | MgO | Toluene | 150 | 3 | 98 | 3 | 69 | 0 | 72 |
| 9 | $TiO_2$ | Toluene | 150 | 3 | 99 | 0 | 76 | 16 | 92 |
| 10 | $ZrO_2$ | Toluene | 150 | 3 | 89 | 9 | 42 | 19 | 70 |
| 11 | Zr—Ti—O | Toluene | 150 | 3 | 96 | 1 | 54 | 30 | 85 |
| 12 | Mg—Zr—O | Toluene | 150 | 3 | 77 | 37 | 32 | 0 | 69 |
| 13 | $SrTiO_3$ | Toluene | 150 | 3 | 67 | 55 | 1 | 1 | 57 |
| 14 | $La_2O_3$ | Toluene | 150 | 3 | 83 | 10 | 63.2 | 4 | 77 |
| 15 | LaAlMgO La:Al = 1 | Toluene | 150 | 3 | 83 | 6 | 69.1 | 2 | 77 |
| 16 | LaAlMgO La:Al = 1.5 | Toluene | 150 | 3 | 95 | 2 | 88.0 | 2 | 91 |
| 17 | LaAlMgO La:Al = 2 | Toluene | 150 | 3 | 93 | 3 | 82.3 | 2 | 87 |
| 18 | $SiO_2$—NHMe | Toluene | 150 | 3 | 2 | 1 | 0.0 | 0 | 1 |
| 19 | $SiO_2$—$NMe_2$ | Toluene | 150 | 3 | 0 | 0 | 0.0 | 0 | 0 |
| 20 | $SiO_2$—$Al_2O_3$ (100 mg) | Toluene | 150 | 3 | 63 | 32 | 10.3 | 4 | 46 |
| 21 | $SiO_2$—$Al_2O_3$ (200 mg) | Toluene | 150 | 3 | 80 | 22 | 23.7 | 8 | 54 |
| 22 | $SiO_2$—$Al_2O_3$ (overnight) | Toluene | 150 | 3 | 88 | 8 | 36 | 12 | 55 |
| 23 | HAP | Toluene | 150 | 3 | 76 | 46 | 15 | 7 | 68 |
| 24 | HAP (overnight) | Toluene | 150 | 3 | 94 | 11 | 47 | 18 | 76 |

HT = Hydrotalcite;
HAP = Hydroxyapatite.

Example 3

Time-Course Studies on the Hydrotalcite-Catalyzed Trimerization of 2-hexanone

This Example demonstrates the reaction intermediates and products pathways from the self-condensation of 2-hexanone.

Figure 4:
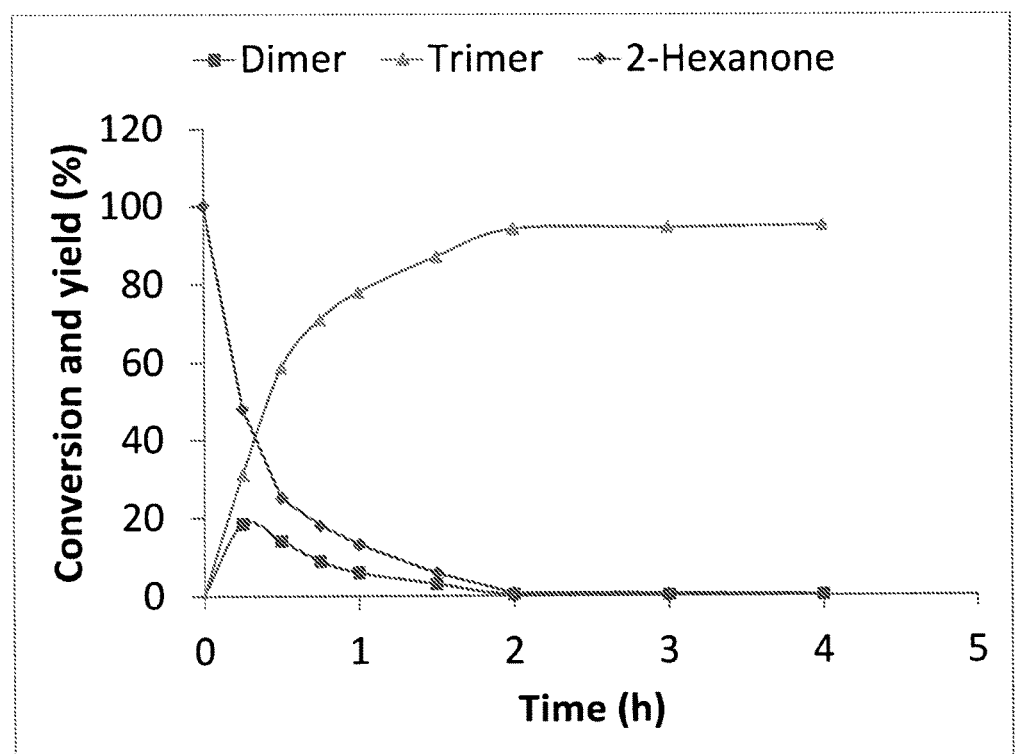
FIG. 4 is a graph depicting the reaction profile for the self-condensation of 2-hexanone in the presence of calcined hydrotalcite at 150° C.

Two time-course studies at 150° C. and 180° C. were performed according to the procedure set forth in Example 1 above. FIG. 4 summarizes the data observed from this time-course study performed at 150° C.

As seen in FIG. 4, trimers were observed to form after heating for 30 minutes. A similar observation was made at the higher temperature, 180° C. With reference to FIG. 4, dimers formed during the course of the reaction were observed to be consumed to yield the trimers as the final products.

Example 4

Self-condensation of 2-butanone

This Example demonstrates the formation of cyclic ketones from 2-butanone (also known as methyl ethyl ketone) using hydrotalcite as the catalyst.

Figure 7:
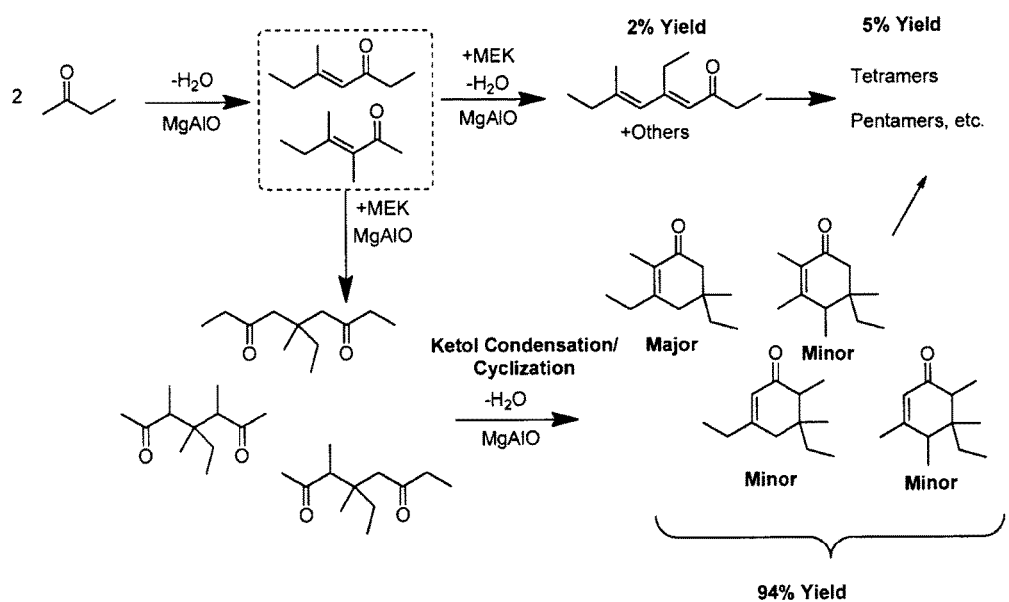
FIG. 7 depicts a reaction scheme for the formation of cyclic ketones from 2-butanone, also known as methyl ethyl ketone (MEK), as described in Example 4.
Figure 8A:
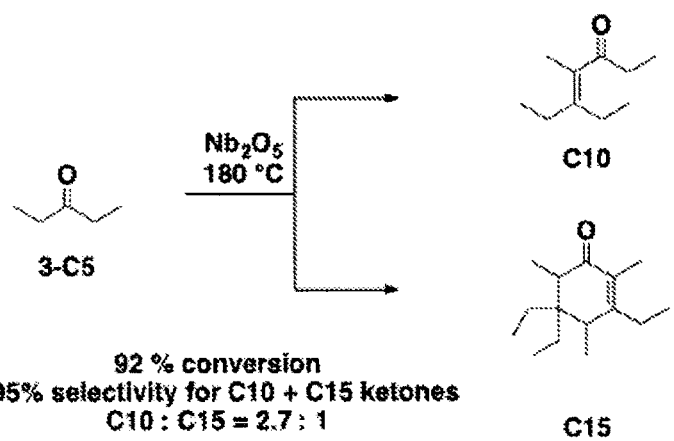
FIGS. 8A-8H depicts the various reactions described in Example 8b.
Figure 8B:
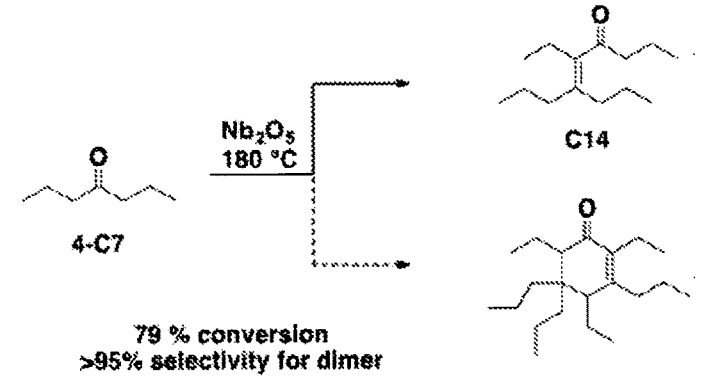
Figure 8C:
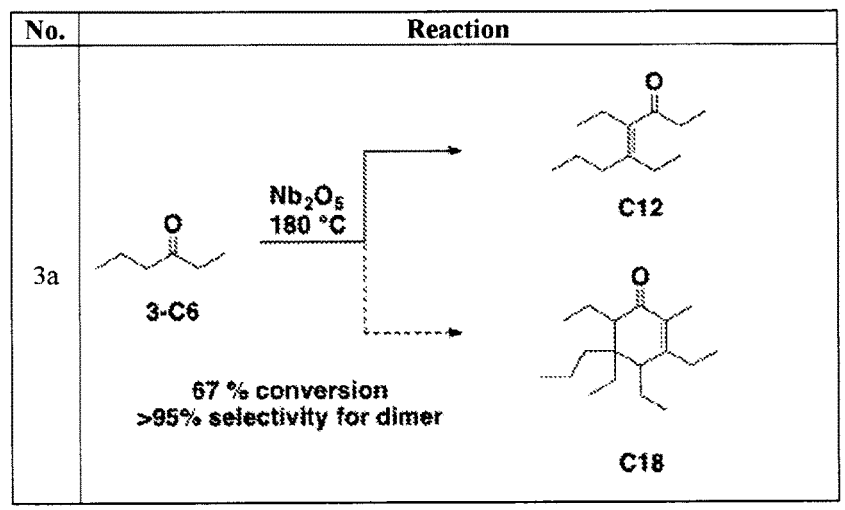
Figure 8D:
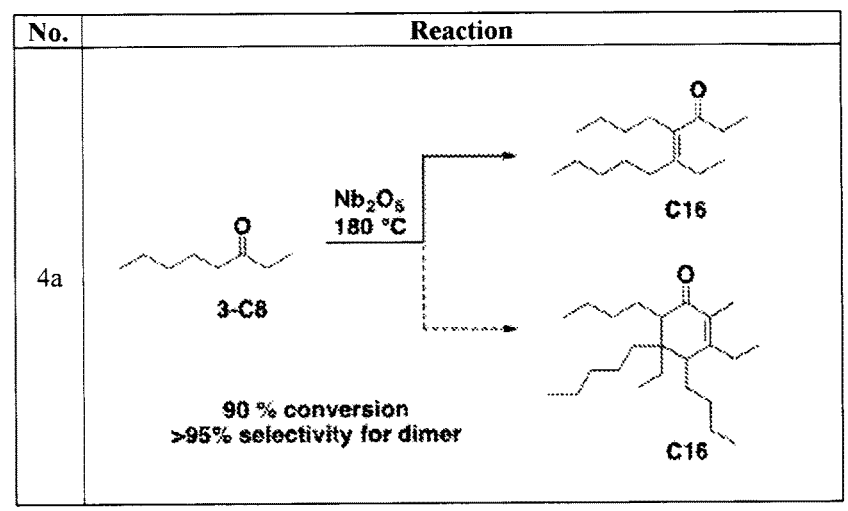
Figure 8E:
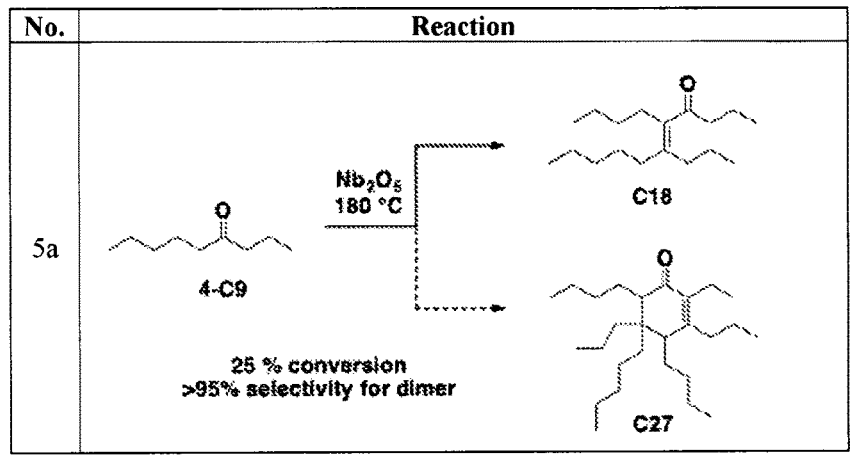
Figure 8F:
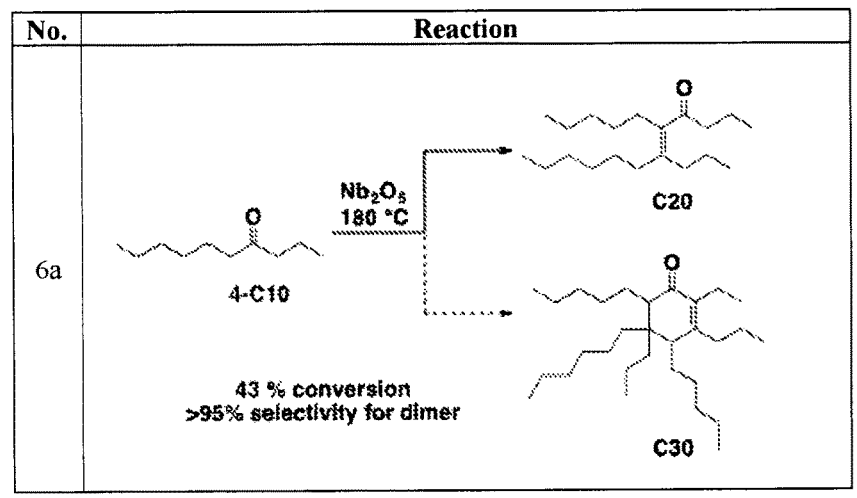
Figure 8G:
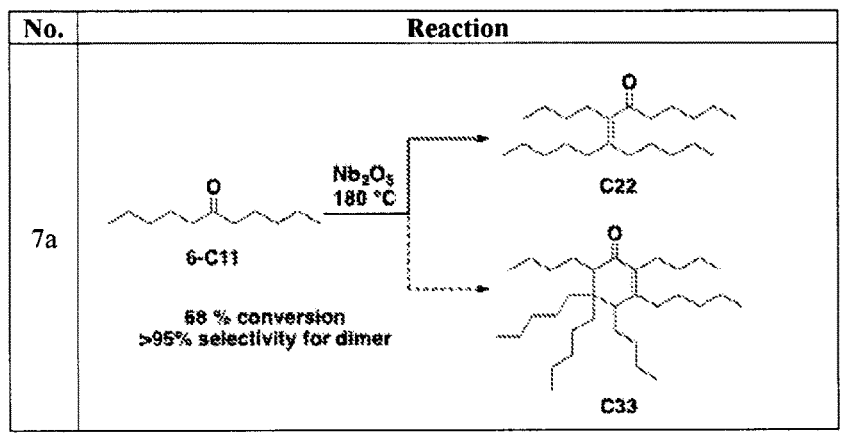
Figure 8H:
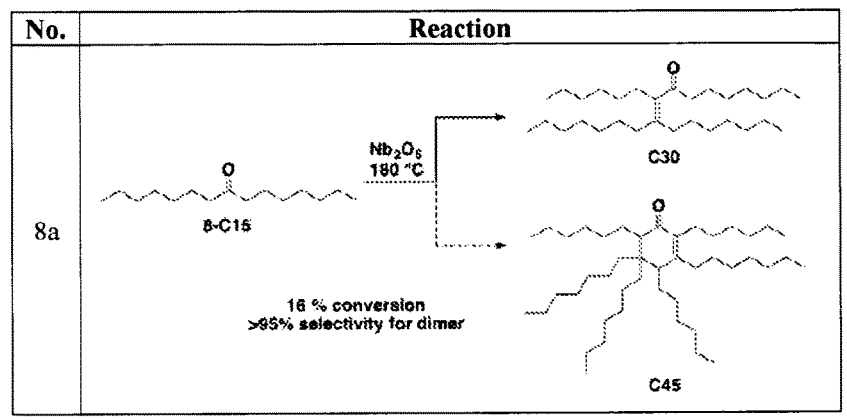
Figure 9A:
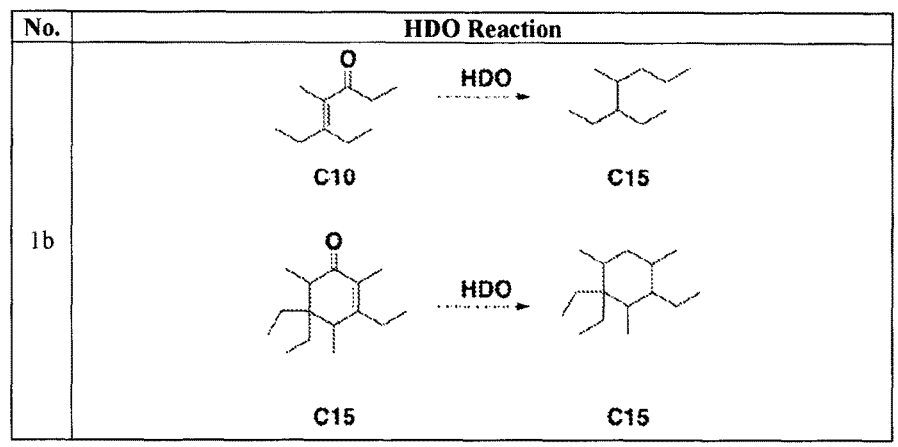
FIGS. 9A-9H depicts various reactions to produce alkanes from a hydrodeoxygenation (HDO) reaction, as described in Example 8b.
Figure 9B:
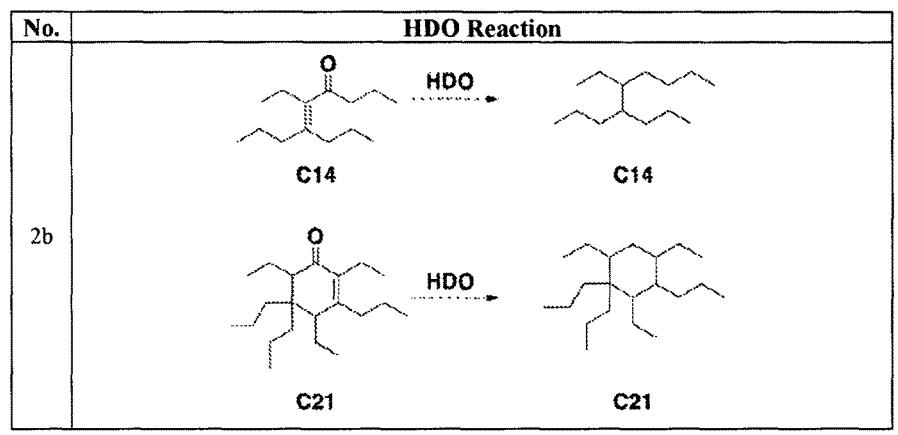
Figure 9C:
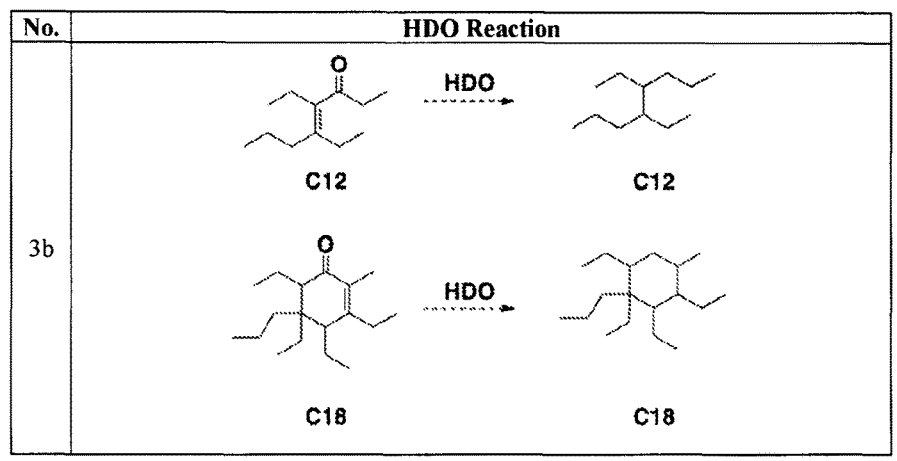
Figure 9D:
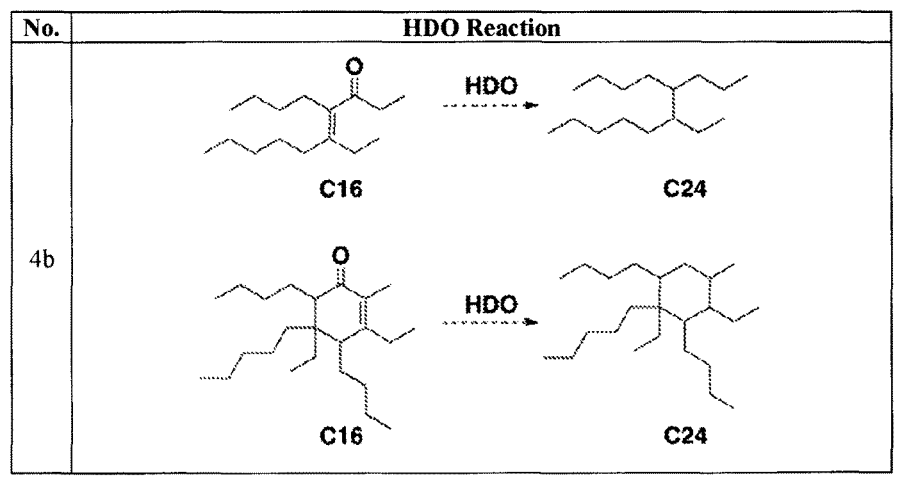
Figure 9E:
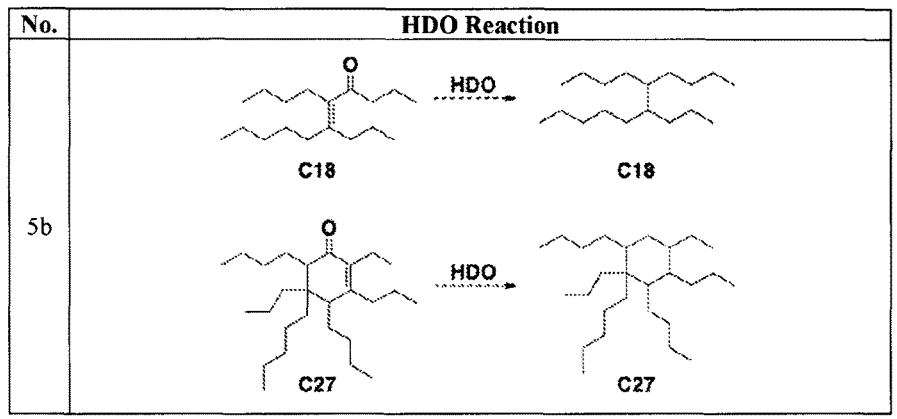
Figure 9F:
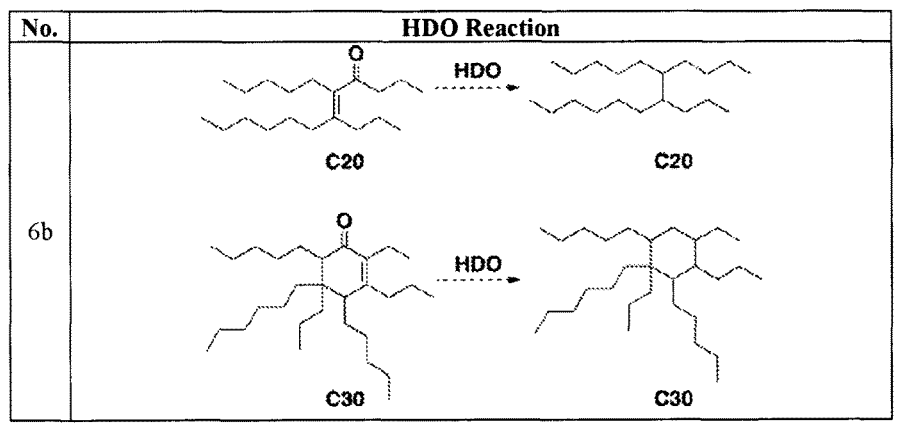
Figure 9G:
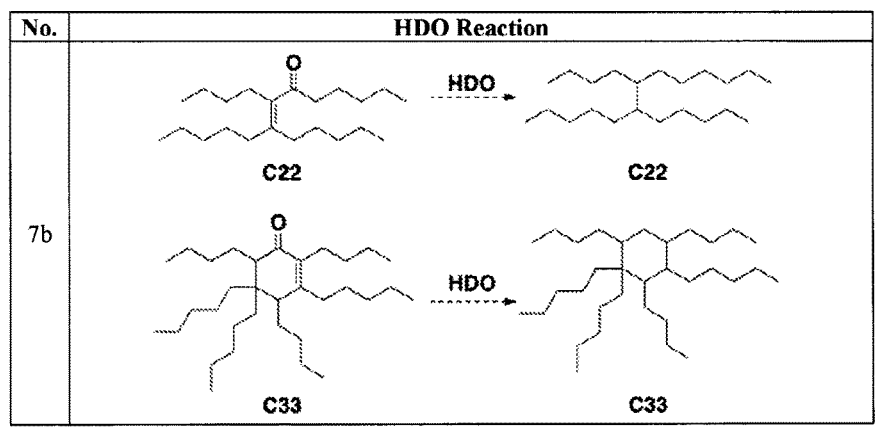
Figure 9H:
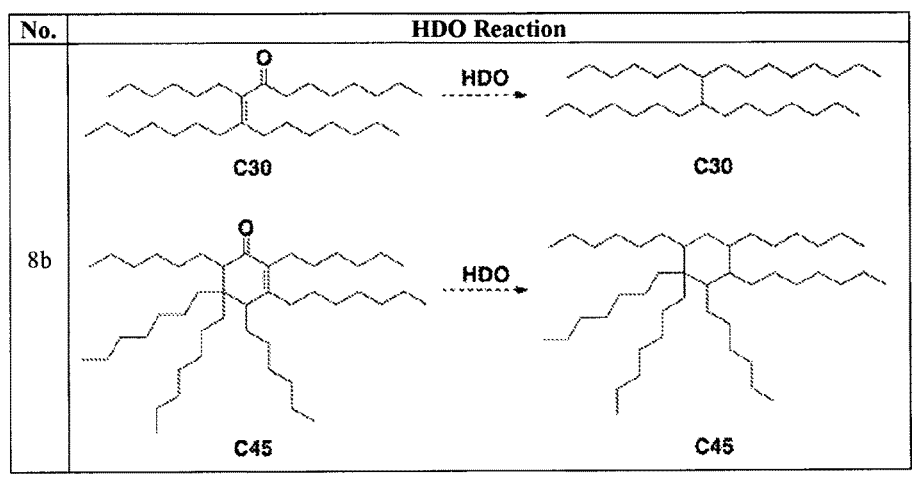

As depicted in FIG. 7, the reaction involving 2-butanone of this Example was performed according to the procedure set forth in Example 1 above. The reaction after 2 hours was observed to produce a mixture of $C_{12}$ trimers formed by cyclization, Michael addition.

Example 5

Substrate Screen for Various Methyl Ketones

This Example explores the self-condensation reaction of various methyl ketones. The reactions of this Example were performed according to the procedure set forth in Example 1 above using the alkyl ketones described in Table 2 below.

Table 2 summarizes the conversion and selectivity of each reaction performed in this Example (where indicated). Conversion was determined relative to the ketone reactant used. Where yields are not indicated, the products were analyzed by mass spectrometry to identify major and minor products.

TABLE 2

| No. | Reaction |
|---|---|
| 1 | Ketone (R-CH2-CO-CH2-R), 100% Conv. → (Calcined HT, Toluene 150 C., 3 h, 93 to 99% yield) → Major cyclohexenone + Minor cyclohexenone (4:1) |
| 2 | 2-Butanone, 100% Conv. → (Calcined HT, Toluene 150 C., 3 h, 94% yield) → Major trimethyl-ethyl cyclohexenone + Minor + Major + Minor |
| 3 | Acetone, 100% Conv. → (Calcined HT, Toluene 150° C., 15 h) → Trimer (5%) + Pentamers (50%) + Hexamers (31%) + Higher oligomers (14%) |
| 4 | Acetophenone (Ph-CO-CH3), 98% Conv. → (Calcined HT, Toluene 150° C., 15 h) → Dimer + Trimer + Trimer (1,3,5-triphenylbenzene) + Tetramer |

TABLE 2-continued
| No. | Reaction |
|---|---|
| 5 | 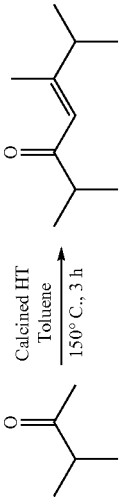 52% Conv. → Calcined HT, Toluene, 150° C., 3 h → 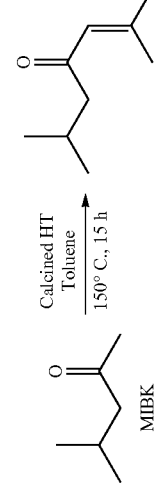 Dimer |
| 6 | MIBK 98% Conv. → Calcined HT, Toluene, 150° C., 15 h → Dimer 4% + Trimer 20% + Trimer Aromatized 3% + Tetramer 64% 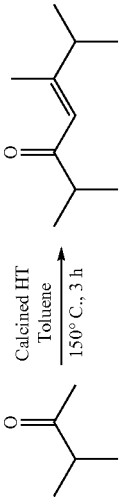 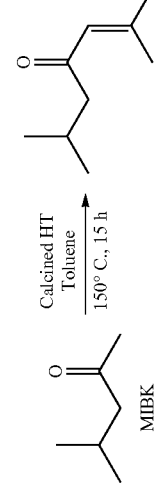 |
R = alkyl, aryl, heteroaryl
*Percentages provided are peak area in gas chromatograph for respective oligomers

Example 6

Hydrodeoxygenation to Produce Cycloalkanes

This Example demonstrates the hydrodeoxygenation of cyclic ketones to produce cyclic alkanes.

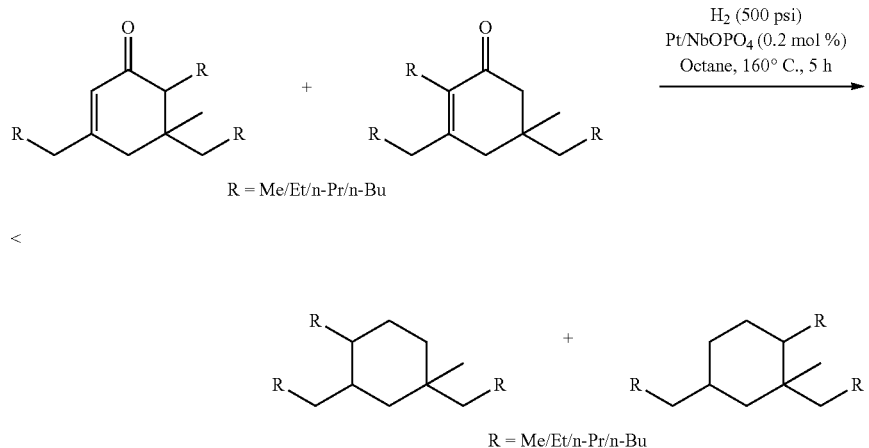

A solution of cyclic ketones (5 mmol) (as indicated in the reaction scheme above) in octane (5 mL) and Pt/NbOPO4 (2 wt %, 100 mg, 0.01 mmol Pt) were added to a 25 mL parr reactor vessel. The reactor was sealed, and flushed with 500 psi of nitrogen gas (2 times) and 500 psi of hydrogen gas (3 times). The reactor was then charged with 500 psi of hydrogen gas and heated to 160° C. with stirring (500 rpm) for 5 h. The reaction mixture was cooled to room temperature, filtered through a fritted funnel using hexanes as washing solvent (3×20 mL) to remove catalyst particles. The crude products in the filtrate were then analyzed as well as quantified using gas chromatography. The filtrate was concentrated under reduced pressure to recover cyclic alkanes in about 100% yield.

Example 7

Co-Processing of Alkyl Ketones

This Example demonstrates the formation of cyclic ketones using a mixture of alkyl ketones. The first reaction involves the co-processing of 2-hexanone and 2-pentanone, and the second reaction involves the co-processing of 2-hexanone, 2-pentanone and 2-butanone.

Reaction 1

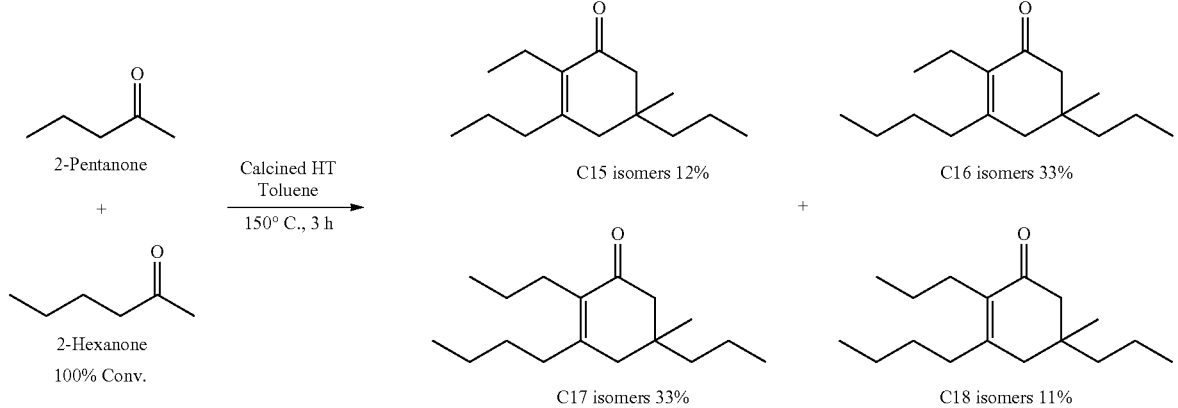

Reaction 2

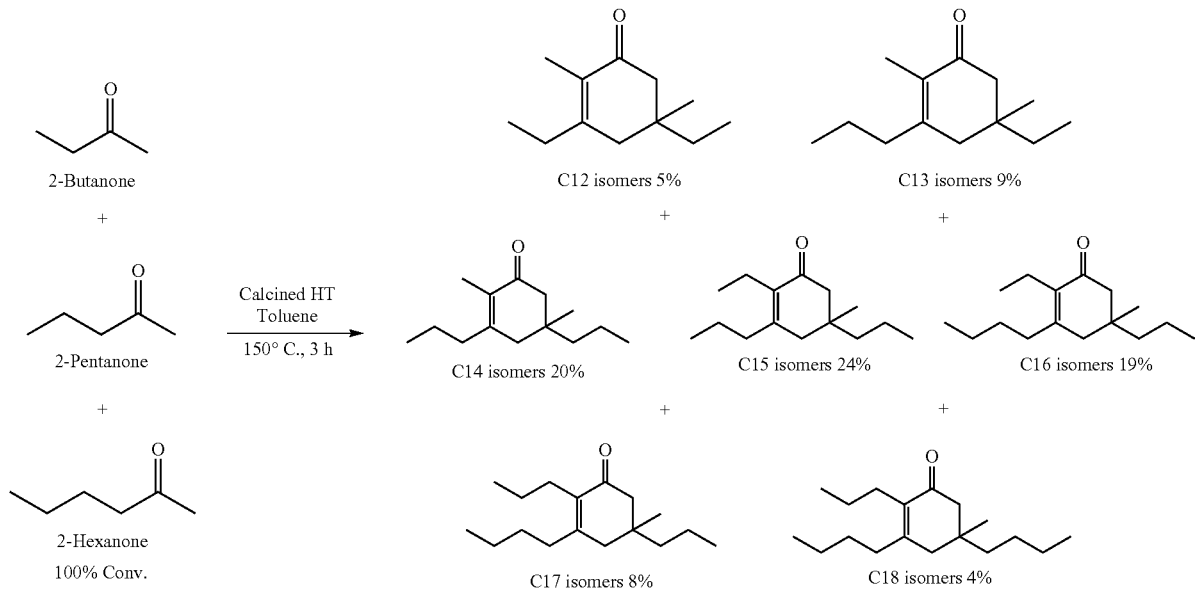

Figure 5A:
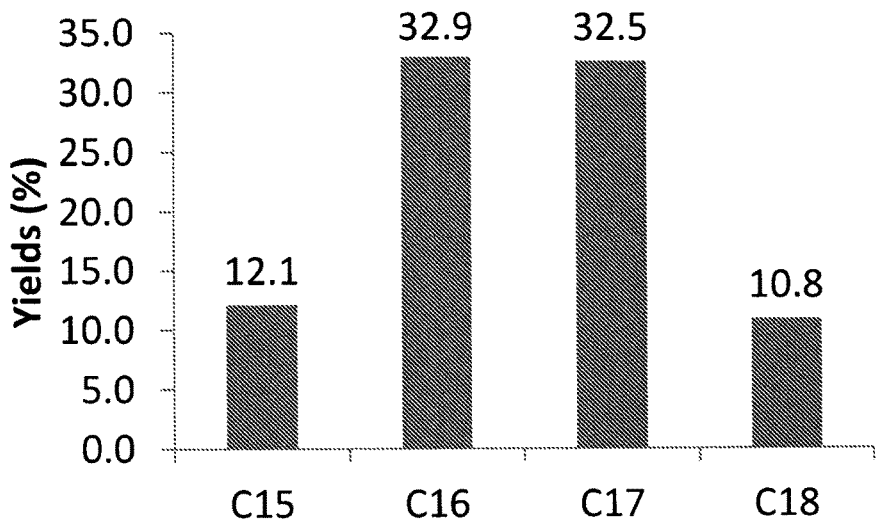
FIG. 5A is a graph depicting the product distribution from the reaction of 2-hexanone and 2-pentanone.
Figure 5B:
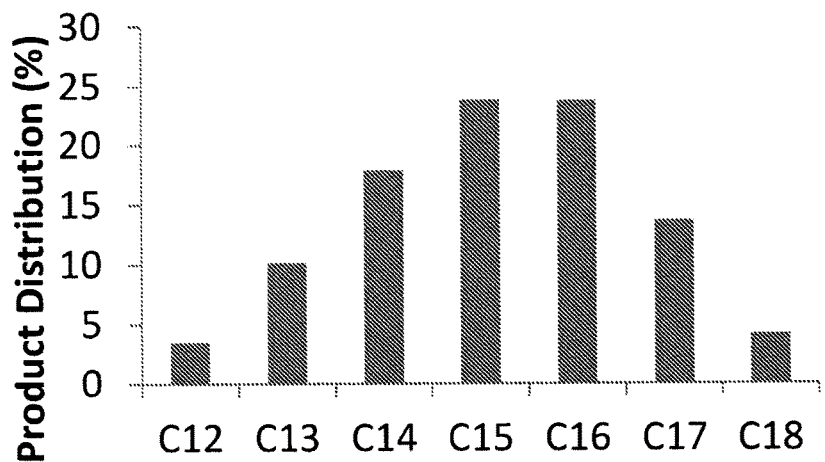
FIG. 5B is a graph depicting the product distribution from the reaction of 2-hexanone, 2-pentanone, and 2-butanone.

The reactions of this Example were performed according to the procedure set forth in Example 1 above using the alkyl ketones described in the reaction schemes above. FIGS. 5A and 5B summarize the distribution of products observed for each reaction.

Example 8a

Catalyst Screen for Oligomerization of 4-C7 Ketone

This Example demonstrates the formation of acyclic ketones from a 4-C7 ketone (as depicted below) using various catalysts.

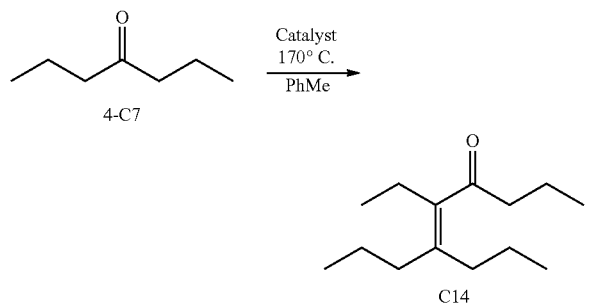

A solution of 4-heptanone (4-C7) (2 mmol) in toluene (1 mL) was added with the catalyst as specified in Table 3 below to a q-tube that was sealed and heated overnight at a temperature of 170° C. The next day, the reaction mixture was then cooled, and an amount of internal standard (dodecane) was added. The product mixture was then passed through a small plug of silica gel and washed with ethyl acetate (3×50 mL) to remove solid catalyst particles. The crude products in the filtrate were then analyzed as well as quantified using gas chromatography.

Table 3 summarizes the conversion and selectivity of each reaction performed in this Example. Conversion was determined relative to the ketone reactant used. Yield is provided as the sum of the products depicted in the reaction scheme provided.

TABLE 3

| Catalyst | Conversion | Selectivity |
|---|---|---|
| Calcined hydrotalcite | 22% | 95% |
| TiO$_2$ | 23% | 95% |
| ZrO$_2$ | 15% | 95% |
| Amberlyst 15 | 89% (includes a mixture of products, including C14 product above) | ND |
| Polystyrene sulfonic acid sodium salt | 3% | No product observed |
| Nafion | 97% (includes a mixture of products, including C14 product above) | ND |
| Silica-Alumina | 25% | 95% |
| p-Toluenesulfonic acid (PTSA) | 77% (includes a mixture of products, including C14 product above) | ND |
| Pyridinium p-toluenesulfonate (PPTS) | 8% | No product observed |
| NbO | 10% | No product observed |
| NbOPO$_4$ | 58% | 95% |
| Nb$_2$O$_5$ | 79% | 95% |

ND = not determined

Example 8b

Oligomerization of Various Other Alkyl Ketones

This Example demonstrates the synthesis of various cyclic and acyclic ketones from various alkyl ketones (non-methyl alkyl ketones).

FIGS. 8A-8H depict the reactions performed in this Example. Each reaction was performed according to the procedure set forth in Example 8a above, using Nb$_2$O$_5$ as the catalyst, and the starting ketone and temperature as described in each reaction scheme below. The conversion and selectivity is also provided in FIGS. 8A-8H for each reaction, and is determined according to the procedure described in Example 8a above.

The cyclic and acyclic ketones produced in this Example can then be hydrodeoxygenated using any suitable methods known in the art and described herein to produce their corresponding alkanes. FIGS. 9A-9H depict the alkanes that can be obtained from such a hydrodeoxygenation (HDO) reaction.

Example 9

Synthesis of Cycloalkanes

This Example demonstrates the synthesis of cycloalkanes suitable for use as lubricants from alkyl ketones. Trimerization of the alkyl ketone produces a mixture of cyclic ketones, which are subsequently hydrodeoxygenated to form the cycloalkanes depicted in the reaction scheme below.

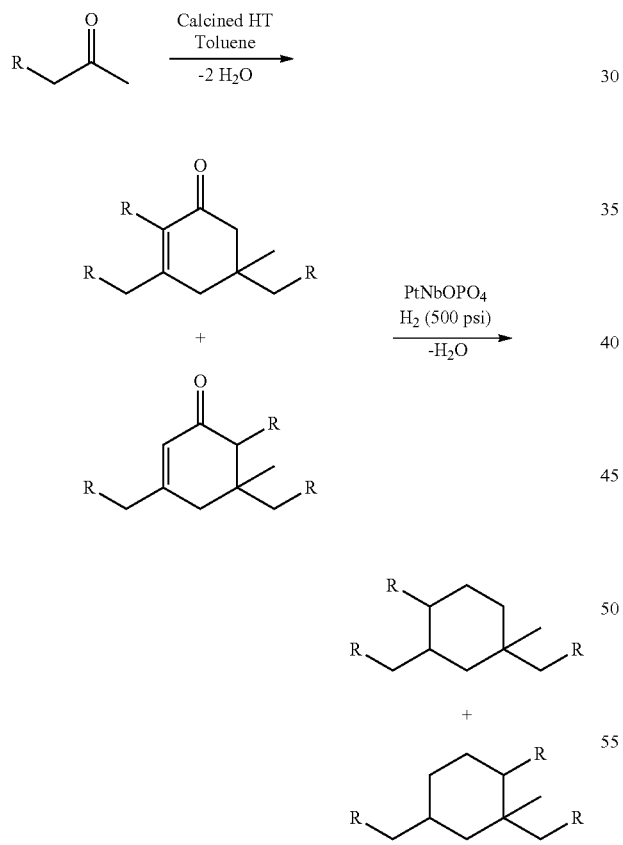

Reaction No. 1: C24 R = n-pentyl
Reaction No. 2: C27 R = n-hexyl
Reaction No. 3: C30 R = n-heptyl
Reaction No. 4: C33 R = n-octyl
Reaction No. 5: C36 R = n-nonyl Synthesis of Cyclic Ketones:

For each of reaction nos. 1-5 depicted in the reaction scheme above, a solution of the ketone (20 mmols) (as specified in the reaction scheme) in toluene (30 mL) was added with calcined hydrotalcite (2 g) in a 100 mL round bottom flask equipped with a magnetic spin bar. The flask containing the reaction mixture was then attached to a Dean-Stark apparatus and refluxed with stirring (800 rpm) in a pre-heated oil bath at 160° C. for 3 hours. The collection of by-product water in the apparatus was observed during the course of the reaction. The cyclic ketone product mixture was then filtered using a fritted funnel by washing with ethyl acetate (3×50 mL) to remove solid catalyst particles. The crude product mixture of cyclic ketones was obtained by evaporating the solvents under reduced pressure, and was analyzed by GC-FID-MS. Yields of the cyclic ketones in the product mixture for each reaction was determined.

Hydrodeoxygenation of Cyclic Ketones to Cycloalkanes:

A solution of crude product mixture of cyclic ketones for each reaction no. 1-4 (5 mmol) in octane (5 mL) was added Pt/NbOPO$_4$ (2 wt %, 100 mg, 0.01 mmol Pt) in a 25 mL parr reactor vessel. The reactor was sealed, and flushed subsequently with 500 psi of nitrogen gas (2 times) and 500 psi of hydrogen gas (3 times). The reactor was then charged with 500 psi of hydrogen gas and heated to 160° C. with stirring (500 rpm) for 5 h. The reaction mixture was cooled to room temperature, filtered through a fritted funnel using hexanes as washing solvent (3×20 mL) to remove catalyst particles. The crude product mixture of cycloalkanes in the filtrate were then analyzed, as well as quantified using gas chromatography. The filtrate was concentrated under reduced pressure to recover cyclic alkanes in quantitative yields. Yields of the cycloalkanes in the product mixture for each reaction was found to be greater than 99%.

Example 10

Substrate Screen for Synthesizing Cycloalkanes

This Example demonstrates the use of various alkyl ketones to synthesize cycloalkanes suitable for use as lubricants. Trimerization of the alkyl ketone produces a mixture of cyclic ketones, which are subsequently hydrodeoxygenated to form the cycloalkanes depicted in Table 4 below.

The reactions of this Example were performed according to the procedure set forth in Example 1 above using the alkyl ketones described in Table 4 below. The crude mixture of cyclic ketones were then hydrogenated to form cycloalkanes according to the procedure set forth in Example 9 above.

TABLE 4

| No. | Alkyl Ketone | Cyclic Ketone | Cycloalkane |
|---|---|---|---|
| 1 | C15; $R^1$ = (difuran group) | C45 | C45; $R^{1x}$ = iso-undecyl<br>and structural isomers thereof |
| 2 | C9; $R^1$ = (methylfuran group) | C27 | C27; $R^{1x}$ = n-pentyl<br>and structural isomers thereof |
| 3 | C8; $R^1$ = (furan group) | C24 | C24; $R^{1x}$ = n-butyl<br>and structural isomers thereof |

In order to evaluate the lubricant properties, the C45 cycloalkane was synthesized on multi-gram scale according to the procedures described in this Example The resulting C45 cycloalkane was then subjected to ASTM standard evaluation techniques for lubricants. The pour point, viscosity index and volatility were measured, and was observed to have the following properties:

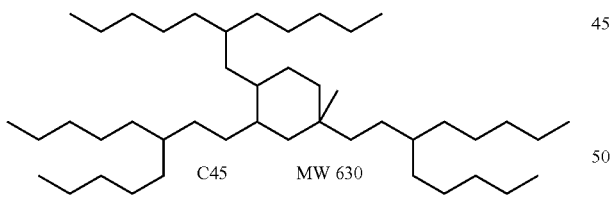

C45   MW 630

The synthesized cyclic alkane was observed to have a pour point, a vapor pressure and an oxidizing property suitable for use as a lubricant.

Example 11

Dimerization and Trimerization of 2-hexanone and 2-hexanol

This Example demonstrates the use of 2-hexanone and 2-hexanol to produce cyclic and acyclic alkanes.

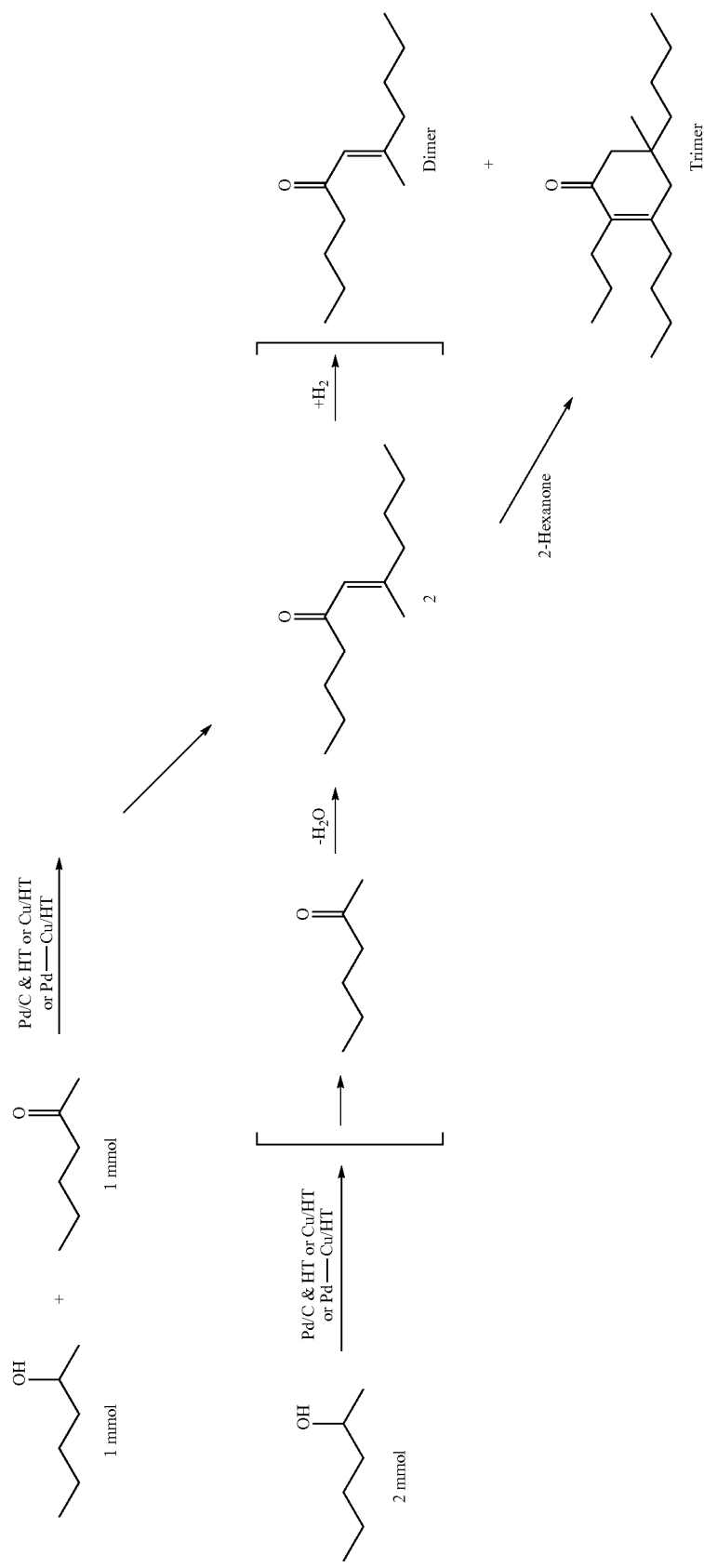

A solution of alcohol (2 mmols) or mixture of alcohol and ketone (1 mmol each) in toluene (3 mL) was added with the supported metal catalyst of choice (Pd/HT or Pd—Cu/HT, 1 mol % metal loading) in a pressure tube equipped with a magnetic spin bar. The reaction mixture was sealed and stirred (800 rpm) on the pre-heated deck of a stirrer at 180° C. for 3 hours. The reaction mixture was then cooled, and added with a known quantity of internal standard (dodecane). The product mixture was then passed through a small plug of silica gel and washed with ethyl acetate (3×10 mL) to remove solid catalyst particles. The crude products in the filtrate were then analyzed as well as quantified using gas chromatography.

Tables 5 and 6 below summarize the two reactions performed in this Example, including the amount of 2-hexanone and 2-hexanol used, and the amount and type of catalyst used, as well as the product distribution of dimer and trimer observed.

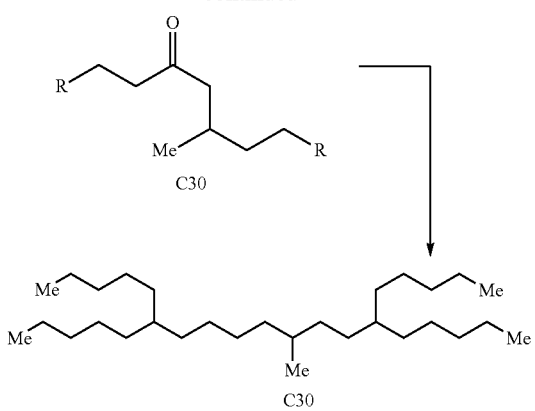

TABLE 5

| No. | 2-Hexanone | 2-Hexanol | Cat. (1 mol %) | HT (mg) | 2-Hexanone | 2-Hexanol | Dimer | Trimer | Total |
|---|---|---|---|---|---|---|---|---|---|
| 1 | 1 mmol | 1 mmol | Pd/C | 200 | 4.9 | 13.4 | 46.4 | 23.8 | 88.5 |
| 2 | 0 | 2 mmol | Pd/C | 200 | 2.9 | 86.3 | 1.0 | 0.1 | 90.3 |
| 3 | 1 mmol | 1 mmol | Cu/HT | 135 | 6.1 | 20.0 | 42.9 | 22.9 | 91.9 |
| 4 | 0 | 2 mmol | Cu/HT | 135 | 0.5 | 89.9 | 0.0 | 0.1 | 90.5 |
| 5 | 1 mmol | 1 mmol | Pd—Cu/HT | 160 | 11.4 | 7.5 | 53.1 | 20.2 | 92.1 |
| 6 | 0 | 2 mmol | Pd—Cu/HT | 160 | 6.4 | 8.6 | 79.4 | 0.5 | 95.0 |

TABLE 6

| No. | 2-Hexanol | Cat. | HT (mg) | 2-Hexanone | 2-Hexanol | Dimer | Trimer | Total |
|---|---|---|---|---|---|---|---|---|
| 1 | 2 mmol | Pd/HT (0.5 mol %) | 180 | 6.7 | 69.5 | 13.1 | 0.9 | 90.2 |
| 2 | 2 mmol | Pd/HT (1 mol %) | 160 | 7.2 | 59.8 | 23.1 | 1.5 | 91.7 |
| 3 | 2 mmol | Cu/HT (1 mol %) | 140 | 0.8 | 90.4 | 0.0 | 0.1 | 91.3 |
| 4 | 2 mmol | Cu/HT (2 mol %) | 80 | 2.8 | 89.1 | 0.3 | 0.1 | 92.3 |
| 5 | 2 mmol | Pd—Cu/HT (0.5 mol %) | 180 | 6.7 | 13.2 | 73.7 | 3.7 | 97.3 |
| 6 | 2 mmol | Pd—Cu/HT (1 mol %) | 160 | 0.5 | 0.1 | 90.3 | 8.3 | 99.3 |

Example 12

Dimerization of a Secondary Alcohol to Produce an Acyclic Ketone

This Example demonstrates the use of a secondary alcohol to produce an acyclic ketone.

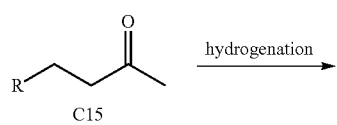

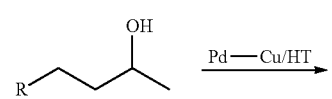

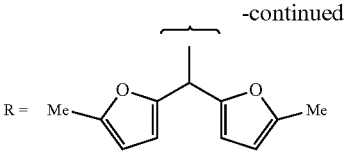

Hydrogenation Step:

A solution of C15 methyl ketone (10 mmol) (as depicted in the reaction scheme above) in ethanol (25 mL) was added PtSn/Al$_2$O$_3$ catalyst in a 50 mL parr reactor vessel. The reactor was sealed, and flushed subsequently with 500 psi of nitrogen gas (2 times) and 200 psi of hydrogen gas (3 times). The reactor was then charged with 200 psi of hydrogen gas and heated to 100° C. with stirring (500 rpm) for 12 h. The reaction mixture was cooled to room temperature, filtered through a fritted funnel using ethyl acetate as washing solvent (3×50 mL) to remove catalyst particles. The crude products in the filtrate were then analyzed as well as quantified using gas chromatography. The filtrate was concentrated under reduced pressure to recover alcohol in quantitative yield.

Dimerization Step:

A solution of the alcohol formed in the preceding hydrogenation step (2 mmols) (3 mL) was added with the supported metal catalyst, Pd—Cu/HT (1 mol % metal loading) in a pressure tube equipped with a magnetic spin bar. The reaction mixture was sealed and stirred (800 rpm) on the pre-heated deck of a stirrer at 180° C. for 3 hours. The reaction mixture was then passed through a small plug of silica gel and washed with ethyl acetate (3×10 mL) to remove solid catalyst particles. The crude C30 dimer product was quantitatively recovered by removing the solvents under reduced pressure.

Hydrodeoxygenation Step:

A solution of acyclic ketones (2 mmol) in octane (8 mL) was added Pt/NbOPO4 (2 wt %, 100 mg, 0.01 mmol Pt) in a 25 mL parr reactor vessel. The reactor was sealed, flushed subsequently with 500 psi of nitrogen gas (2 times) and 500 psi of hydrogen gas (3 times). The reactor was then charged with 500 psi of hydrogen gas and heated to 250° C. with stirring (500 rpm) for 5 h. The reaction mixture was cooled to room temperature, filtered through a fritted funnel using hexanes as washing solvent (3×20 mL) to remove catalyst particles. The crude products in the filtrate were then analyzed as well as quantified using gas chromatography. The filtrate was concentrated under reduced pressure to recover cyclic alkanes in quantitative yields.

Example 13

Cross-Condensation Reaction of an Alkyl Ketone and Aldehyde

This Example demonstrates the use of a secondary alcohol to produce an acyclic ketone suitable for use as a lubricant.

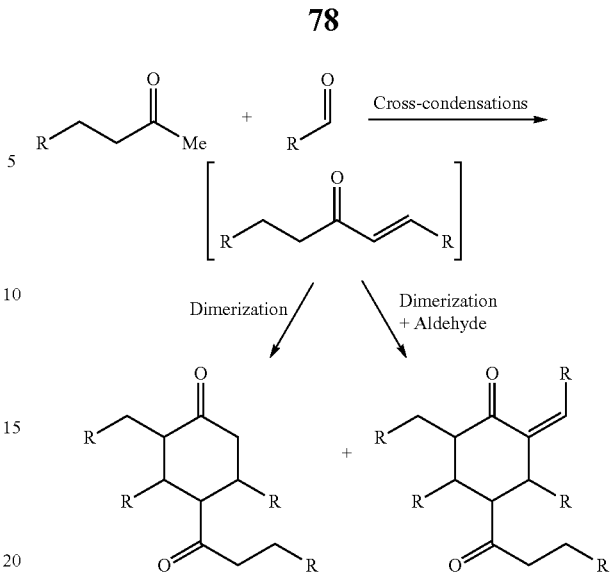

A solution of mixture of ketone and aldehyde (as indicated in Table 7 below) (1 mmol each) in toluene (3 mL) was added with calcined hydrotalcite (200 mg) in a pressure tube equipped with a magnetic spin bar. The reaction mixture was sealed and stirred (800 rpm) on the pre-heated deck of a stirrer at 150° C. for 3 hours. The reaction mixture was then cooled, and added with a known quantity of internal standard (dodecane). The product mixture was then passed through a small plug of silica gel and washed with ethyl acetate (3×10 mL) to remove solid catalyst particles. The crude products in the filtrate were then analyzed as well as quantified using gas chromatography.

TABLE 7

| Reaction | Product from dimerization of ketone | Product from dimerization of ketone and aldehyde |
|---|---|---|
| R = furan | C26 | C31 |
| R = Me-furan | C30 | C36 |
| R = Me-furan and furan | C28 | C33 or C34 |

Example 14

Effect of Water

This Example demonstrates the effect of water in the conversion of alkyl ketones into trimerized and dimerized ketone products.

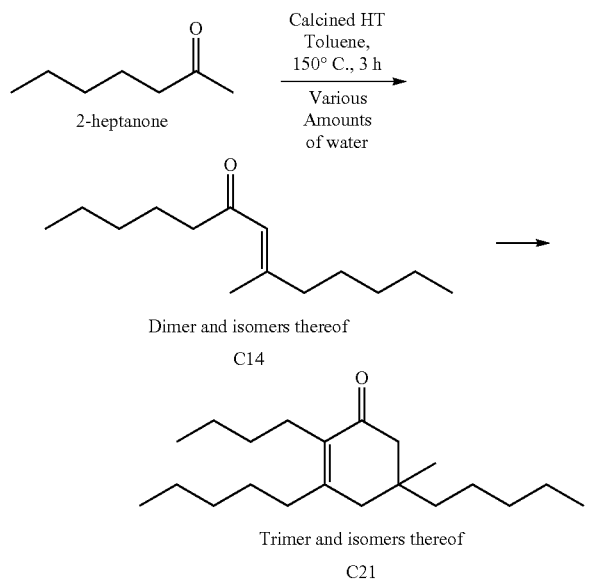

Several parallel reactions using 2-heptanone (0.228 g, 2 mmol), calcined hydrotalcite (200 mg), and toluene (2.610 g) were performed according to the procedure set forth in Example 1 above (at 150° C., 3 hours). The following amounts of water were added to separate reaction mixtures to determine the effect of water: 0, 0.46, 0.91, 1.36, 2.44, 3.56, and 6.87 wt % of water. The wt % of water was calculated as follows:

$$\text{Wt \% of water} = \frac{\text{Weight of water}}{\text{Weight of total reaction mixture}} \times 100$$

Figure 6:
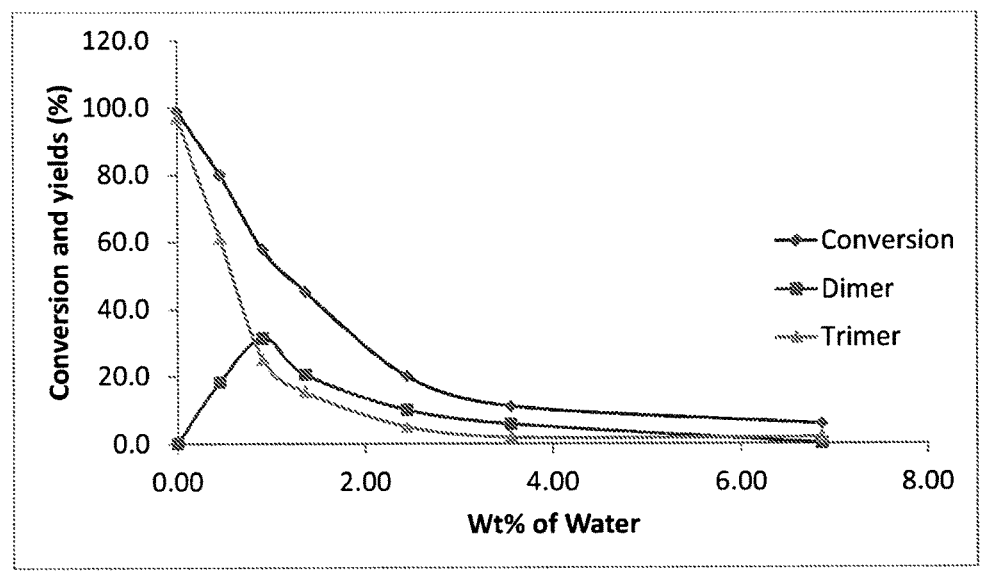
FIG. 6 is a graph depicting the effect of varying amounts of water on the production of dimerized and trimerized ketones.

The results comparing the effect of water on the products formed are summarized in FIG. 6.

Example 15

Substrate, Catalyst, and Condition Screens for Synthesizing Cycloalkanes

Figure 10:
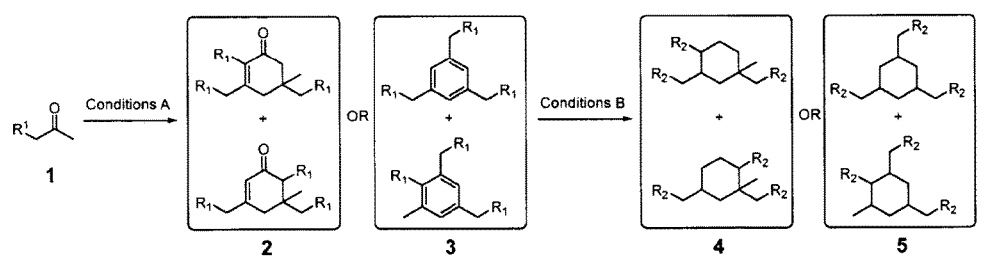
FIG. 10 depicts a reaction scheme directed to the self-condensation of various alkyl ketones to produce a mixture of cyclic ketones (2) or a mixture of aromatic compounds (3), as described in Example 15.

As depicted in FIG. 10, this Example demonstrates the self-condensation of various alkyl ketones in the presence of MgAlO catalyst to produce a mixture of cyclic ketones (2), or in the presence of $Ta_2O_5$/SBA-15 catalyst to produce a mixture of aromatic compounds (3). The self-condensation products were then hydrogenated and deoxygenated to produce the corresponding mixtures of cyclic alkanes (4) and (5).

Preparation of Catalysts—MgAlO:
To prepare the MgAlO catalyst, a commercial synthetic hydrotalcite (Mg/Al=3:1) was calcined at 700° C. for 2 h in static air by ramping the temperature at 2° C./min.

Preparation of Catalysts—4 wt % $Ta_2O$/SBA-15:
The 4 wt % $Ta_2O_5$/SBA-15 catalyst was prepared via incipient wetness impregnation method using synthesized SBA-15. First, tantalum (V) ethoxide (0.375 g, 0.25 mL) was dissolved in absolute ethanol (8.5 mL). The resulting solution was added in multiple portions to SBA-15 (5 g) with grinding to give uniform distribution. The mixture was dried at 100° C. for 16 h, then calcined at 450° C. for 4 h by ramping the temperature at 5° C./min.

Preparation of Catalysts—2 wt % Pt/NbOPO$_4$:
To prepare the 2 wt % Pt/NbOPO$_4$ catalyst, commercial niobium phosphate was calcined at 300° C. in air by ramping the temperature at 2° C./min to 300° C., and then holding at 300° C. for 3 h. Then, chloroplatinic acid hexahydrate (212 mg) was dissolve in deionized water (1 mL) and impregnated on the calcined niobium phosphate (4 g) using the incipient wetness method as described above. This material was dried overnight in an oven at 100° C. and subjected to reduction at 300° C. for 3 h in a tubular oven by ramping at 2° C./min. The hydrogen flow was maintained at 50 mL/min throughout the course of reduction.

All other catalysts were commercially obtained.

Characterization of Catalysts:
Catalyst surface area was determined by Brunauer-Emmett-Teller (BET) analysis using a Micromeritics TriStar system with a FlowPrep 060 degassing system. The material (~200 mg) was degassed in a BET tube at 120° C. for 6 hours under flowing argon. The catalyst surface area was determined by the BET isotherm. The surface area for MgAlO, $Ta_2O_5$/SBA-15, and Pt/NbOPO$_4$ catalysts were found to be 174±2, 876±11, and 157±1 m$^2$/g, respectively.

Self-Condensation of Ketones to Cyclic Ketones (2):
A series of self-condensation reactions were carried out using the MgAlO catalyst, prepared as described above. For each reaction catalyzed by MgAlO, the ketone, solvents, catalyst loading, the reaction apparatus and conditions used were as described in Table 8 below. For each reaction, a solution of the ketone (20 g) in the corresponding solvent (200 mL) was combined with MgAlO catalyst (20 g) in a 500 mL round bottom flask (RBF) equipped with a magnetic spin bar. The RBF was then attached to the corresponding reaction apparatus and refluxed with stirring (800 rpm) in a pre-heated oil bath under the corresponding Conditions A listed in Table 8. The by-product water was continuously removed from the reaction mixture and collected in the side-arm of the apparatus during the course of the reaction. The product mixture was then cooled to room temperature and filtered through a fritted funnel by washing the catalyst using ethyl acetate (3×100 mL). For each reaction, the mixture of cyclic ketone products (2) in the filtrate was recovered after evaporation of the solvents. Self-condensation of Ketones to Aromatic Compounds (3): A series of self-condensation reactions were carried out using the 4 wt % $Ta_2O_5$/SBA-15 catalyst, prepared as described above. For each reaction catalyzed by $Ta_2O_5$/SBA-15, the ketone, solvents, catalyst loading, reaction apparatus and conditions used were as described in Table 8 below. For each reaction, a solution of the ketone (4 g) in the corresponding solvent (18 mL) was added with $Ta_2O_5$/SBA-15 (2 g) in the corresponding 50 mL reaction apparatus. The reactor was then sealed and heated with stirring (400 rpm) at the corresponding Conditions A listed in Table 8. The product mixture was then cooled to room temperature and filtered through a fritted funnel by washing the catalyst using ethyl acetate (3×50 mL). For each reaction, the mixture of aromatic products (3) in the filtrate was recovered after evaporation of the solvents.

Hydrogenation of Condensate Mixtures to Cyclic Alkene Mixtures:

A series of hydrogenation reactions were carried out using the condensate mixtures, solvents, catalysts, and conditions as listed in Table 8. The metal loadings listed were calculated with respect to the condensate mixtures 2 or 3. For each reaction, a solution of condensate mixture 2 or condensate mixture 3 (5 mmol) in octane (5 mL) was added with the respective hydrogenation catalysts in a 25 mL Parr reactor vessel. The reactor was sealed, flushed with nitrogen gas (2×), hydrogen gas (3×) and subsequently charged with the required pressure of hydrogen gas. The Parr reactor was stirred at 500 rpm and subjected to respective Conditions B listed for each entry in Table 8. The reaction mixture was cooled to room temperature and filtered through a fritted funnel using hexanes as a washing solvent (3×20 mL) to remove the catalyst. The crude products in the filtrate were then analyzed using gas chromatography. The filtrate was concentrated under reduced pressure to recover each mixture cyclic alkanes. Substrates possessing furan moieties (condensate mixtures 2j-1) were subjected to two stage hydrogenation which involved the above procedure in each stage.

TABLE 8

| Entry | Ketone ($C_n$) | Conditions A[a] | Condensate ($C_{3n}$) | Conditions B[b] | Cyclic alkane ($C_{3n}$) |
|---|---|---|---|---|---|
| 1 | 1a ($C_6$) $R^1$ = n-propyl | MgAlO[c], 160° C., 3 h | 2a ($C_{18}$) $R^1$ = n-propyl | Pt/NbOPO$_4$[e], H$_2$ (3.45 MPa), 160° C., 6 h | 4a ($C_{18}$) $R^2$ = n-propyl |
| 2 | 1a ($C_6$) $R^1$ = n-propyl | Ta$_2$O$_5$/SBA-15[d], 200° C., 24 h | 3a $R^1$ = n-propyl | Rh/C[h], H$_2$ (3.45 MPa), 200° C., 16 h | 5a $R^2$ = n-propyl |
| 3 | 1b-f ($C_8$-$C_{12}$) $R_1$ = n-pentyl-n-nonyl | MgAlO[c], 160° C., 6 h | 2b-f ($C_{24}$, $C_{27}$, $C_{30}$, $C_{33}$, $C_{36}$) $R^1$ = n-pentyl-n-nonyl | Pt/NbOPO$_4$[e], H$_2$ (3.45MPa), 160° C., 6 h | 4b-f ($C_{24}$, $C_{27}$, $C_{30}$, $C_{33}$, $C_{36}$) $R^2$ = n-pentyl-n-nonyl |
| 4 | 1g ($C_{15}$) $R^1$ = n-dodecyl | MgAlO[c], 160° C., 12 h | 2g ($C_{45}$) $R^1$ = n-dodecyl | Pt/NbOPO$_4$[e], H$_2$ (3.45 MPa), 200° C., 12 h | 4g ($C_{45}$) $R^2$ = n-dodecyl |
| 5 | 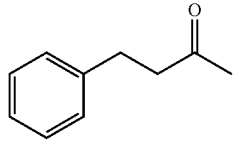<br>1h ($C_{10}$) | MgAlO[c], 160° C., 12 h | 2h ($C_{30}$) $R^1$ = benzyl | Rh/C[h], H$_2$ (3.45 MPa), 120° C., 6 h and then Pt/NbOPO$_4$[e], H$_2$ (3.45 MPa), 160° C., 6 h | 4h ($C_{30}$) $R^2$ = c-hexylmethyl |
| 6 | 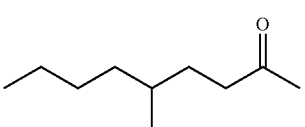<br>1i ($C_{11}$) | MgAlO[c], 160° C., 16 h | 2i ($C_{33}$) $R^1$ = 2-ethylhexyl | Pt/NbOPO$_4$[e], H$_2$ (3.45 MPa), 160° C., 6 h | 4i ($C_{33}$) $R^2$ = 2-ethylhexyl |
| 7 | 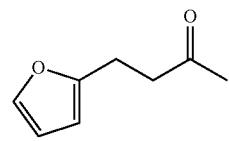<br>1j ($C_8$)<br>and<br>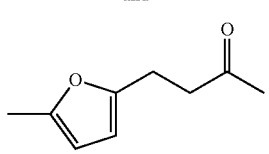<br>1k ($C_9$) | MgAlO[c], 160° C., 16 h | 2j ($C_{24}$) $R^1$ = furfuryl and 2k ($C_{27}$) $R^1$ = 5-methylfurfuryl | Pd/C[i], H$_2$ (2 MPa), 100° C., 5 h and then Pt/NbOPO$_4$[f], H$_2$ (3.45 MPa), 220° C., 6 h | 4j E 4b ($C_{24}$) $R^2$ = n-pentyl and 4k E 4c ($C_{27}$) $R^2$ = n-hexyl |

TABLE 8-continued

| Entry | Ketone ($C_n$) | Conditions A[a] | Condensate ($C_{3n}$) | Conditions B[b] | Cyclic alkane ($C_{3n}$) |
|---|---|---|---|---|---|
| 8 | 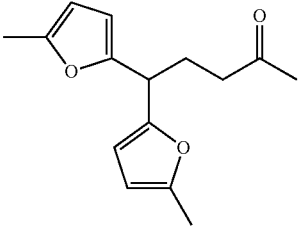<br>1l ($C_{15}$) | MgAlO[c,k], 190° C., 16 h | 2l ($C_{45}$) $R^1$ = 2,2-bis(5-methylfuran-2-yl)ethyl | Pd/C[j], $H_2$ (2 MPa), 100° C., 5 h and then Pt/NbOPO$_4$[g], $H_2$ (3.45 MPa), 250° C., 6 h | 4l ($C_{45}$) $R^2$ = 2-pentylheptyl |
| 9 | 1d ($C_{10}$) | Ta$_2$O$_5$/SBA-15[d], 230° C., 24 h | 3b ($C_{30}$) $R^1$ = n-heptyl | Rh/C, $H_2$ (6.9 MPa), 200° C., 24 h | 5b ($C_{30}$) $R^2$ = n-heptyl |

[a]Entries 1 and 3-8 were carried out in a Dean-Stark apparatus; entries 2 and 9 were carried out in a Parr reactor; toluene was used as the solvent for entries 1-7 and 9; a mixture of xylenes was used as the solvent for entry 8.
[b]Hydrogenations were carried out in a Parr reactor using octane as the solvent.
[c]50 wt % of the catalyst with respect to substrate.
[d]20 wt %.
[e]0.2 mol % of the total metal content with respect to substrate.
[f]0.25 mol %.
[g]0.5 mol %.
[h]2 mol %.
[i]0.1 mol %.
[j]0.2 mol %.
[k]xylenes as solvent.
MgAlO = calcined hydrotalcite.

Characterization of Condensates and Cycloalkanes:

The condensates 2a-2l and 3a-3b, and the cycloalkanes 4a-4l and 5a-5b were analyzed by high-resolution mass spectrometry (HRMS), using solvent-free electrospray ionization (ESI) and electron impact (EI) techniques, without an internal standard. The calculated and measured mass of each analysis is provided in Table 9.

TABLE 9

| Molecular Structure | Molecular Formula | Calculated Mass | Measured Mass |
|---|---|---|---|
| 2a | $C_{18}H_{32}O$ | 264.2453 [M]$^+$ | 264.2451 [M]$^+$, EI |
| 2b | $C_{24}H_{44}O$ | 349.3470 [M + H]$^+$ | 349.3469 [M + H]$^+$, ESI |
| 2c | $C_{27}H_{50}O$ | 391.3940 [M + H]$^+$ | 391.3938 [M + H]$^+$, ESI |

TABLE 9-continued

| Molecular Structure | Molecular Formula | Calculated Mass | Measured Mass |
|---|---|---|---|
| 2d | $C_{30}H_{56}O$ | 433.4409 [M + H]$^+$ | 433.4402 [M + H]$^+$, ESI |
| 2e | $C_{33}H_{62}O$ | 474.4801 [M]$^+$ | 474.4795 [M]$^+$, EI |
| 2f | $C_{36}H_{68}O$ | 517.5348 [M + H]$^+$ | 517.5344 [M + H]$^+$, ESI |
| 2g | $C_{45}H_{86}O$ | 642.6679 [M]$^+$ | 642.6684 [M]$^+$, EI |
| 2h | $C_{30}H_{32}O$ | 409.2531 [M + H]$^+$ | 409.2529 [M + H]$^+$, ESI |
| 2i | $C_{33}H_{62}O$ | 474.4801 [M]$^+$ | 474.4798 [M]$^+$, EI |

TABLE 9-continued

| Molecular Structure | Molecular Formula | Calculated Mass | Measured Mass |
|---|---|---|---|
| 2j | $C_{24}H_{26}O_4$ | 379.1909 [M + H]$^+$ | 379.1905 [M + H]$^+$, ESI |
| 2k | $C_{27}H_{32}O_4$ | 421.2379 [M + H]$^+$ | 421.2377 [M + H]$^+$, ESI |
| 2l | $C_{45}H_{50}O_7$ | 703.3635 [M + H]$^+$ | 703.3632 [M + H]$^+$, ESI |
| 3a | $C_{18}H_{30}$ | 246.2348 [M]$^+$ | 246.2346 [M]$^+$, EI |
| 3b | $C_{30}H_{54}$ | 414.4226 [M]$^+$ | 414.4229 [M]$^+$, EI |

TABLE 9-continued
| Molecular Structure | Molecular Formula | Calculated Mass | Measured Mass |
|---|---|---|---|
| 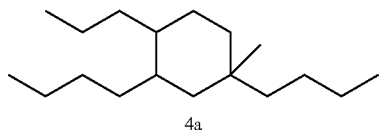 [SMILES: CCCCC1CC(C)(CCCC)CCC1CCC] 4a | $C_{18}H_{36}$ | 252.2817 $[M]^+$ | 252.2815 $[M]^+$, EI |
| 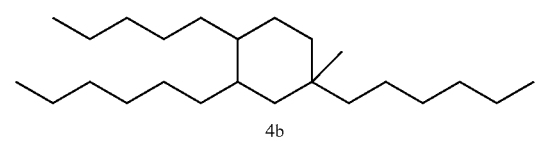 [SMILES: CCCCCCC1CC(C)(CCCCCC)CCC1CCCCC] 4b | $C_{24}H_{48}$ | 336.3756 $[M]^+$ | 336.3748 $[M]^+$, EI |
| 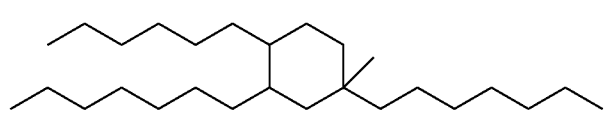 4c | $C_{27}H_{54}$ | 378.4226 $[M]^+$ | 378.4219 $[M]^+$, EI |
| 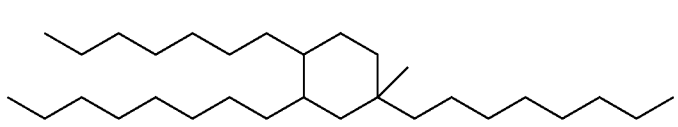 4d | $C_{30}H_{60}$ | 420.4695 $[M]^+$ | 420.4698 $[M]^+$, EI |
| 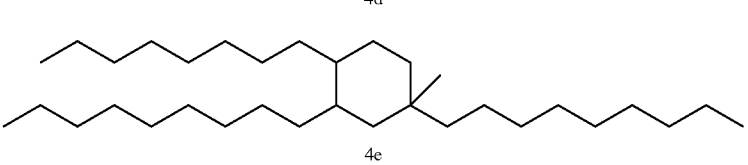 4e | $C_{33}H_{66}$ | 462.5165 $[M]^+$ | 462.5156 $[M]^+$, EI |
| 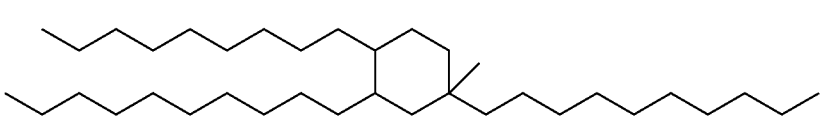 4f | $C_{36}H_{72}$ | 504.5634 $[M]^+$ | 504.5641 $[M]^+$, EI |
| 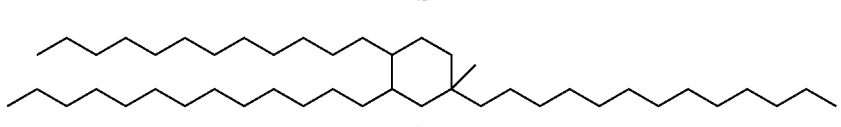 4g | $C_{45}H_{90}$ | 630.7043 $[M]^+$ | 630.7047 $[M]^+$, EI |
| 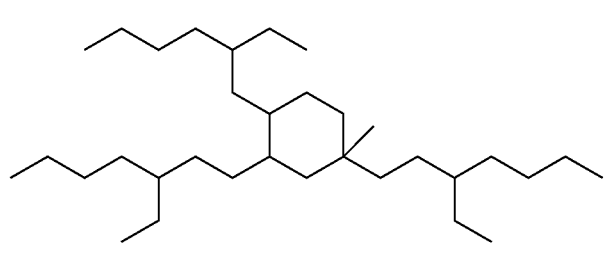 4i | $C_{33}H_{66}$ | 462.5165 $[M]^+$ | 462.5162 $[M]^+$, EI |
| 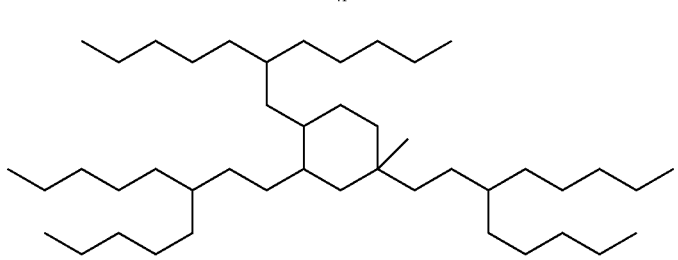 4l | $C_{45}H_{90}$ | 630.7043 $[M]^+$ | 630.7024 $[M]^+$, EI |

TABLE 9-continued

| Molecular Structure | Molecular Formula | Calculated Mass | Measured Mass |
|---|---|---|---|
| 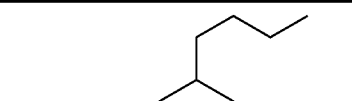 5a | $C_{18}H_{36}$ | 252.2817 $[M]^+$ | 252.2815 $[M]^+$, EI |
| 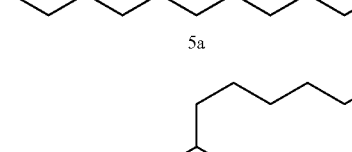 5b | $C_{30}H_{60}$ | 420.4695 $[M]^+$ | 420.4699 $[M]^+$, EI |

Example 16

Trimerization of 2-heptanone to 2,5-dibutyl-5-ethyl-3-pentylcyclohex-2-eneone

This Example demonstrates the self-condensation of 2-heptanone to produce the cyclic ketone 2,5-dibutyl-5-ethyl-3-pentylcyclohex-2-eneone using calcined hydrotalcite as the catalyst.

The calcined hydrotalcite was prepared as described in Example 1 above. A 250 mL RBF was charged with 15 g of calcined hydrotalcite, 52 g of 2-heptanone, and a large stir bar. An empty Dean-Stark trap and condenser were attached to the flask, and the apparatus was heated to 210° C. with intense stirring using a high-temperature oil bath. The reaction was allowed to proceed for eight hours. The reaction mixture was allowed to cool to room temperature and the solids allowed to settle, then a 0.5 mL aliquot of supernatant was withdrawn and dissolved in toluene and analyzed by gas chromatography. The reaction was observed to produce isomers of the cyclic trimer 2-butyl-5-methyl-3,5-dipentyl-cyclohex-2-eneone in 64.9% yield.

What is claimed is:

1. A method for producing at least one cyclic ketone, comprising:
   contacting at least one ketone independently having a structure of formula (A) with catalyst to form a reaction mixture, wherein the contacting of the at least one ketone with the catalyst produces at least one cyclic ketone having a structure of formula (I), (II), (III) or (IV), or any isomers thereof, from at least a portion of the at least one ketone, wherein:
   the at least one ketone independently having the structure of formula (A) is:

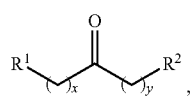

wherein:
   each $R^1$ and $R^2$ is independently H, unsubstituted alkyl, substituted alkyl, —$C(R^t)_3$, —$CH(R^t)_2$, unsubstituted aryl, substituted aryl, unsubstituted heteroaryl, substituted heteroaryl, unsubstituted alicyclyl, substituted alicyclyl, unsubstituted heterocyclyl, or substituted heterocyclyl,
   wherein each $R^t$ is independently unsubstituted aliphatic, substituted aliphatic, unsubstituted aryl, substituted aryl, unsubstituted heteroaryl, substituted heteroaryl, unsubstituted alicyclyl, substituted alicyclyl, unsubstituted heterocyclyl, or substituted heterocyclyl;
   each x and y is independently an integer greater than or equal to 1, provided that when x and y are both 1, either $R^1$ or $R^2$ is other than H;
   the cyclic ketone having the structure of formula (I) is:

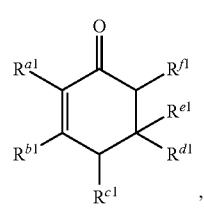

or any isomers thereof, wherein:
$R^{a1}$ is —$(CH_2)_{x-1}R^1$;
$R^{b1}$ is —$(CH_2)_xR^1$;
$R^{c1}$ is —$(CH_2)_{y-1}R^2$;
$R^{d1}$ is —$(CH_2)_xR^1$;
$R^{e1}$ is —$(CH_2)_yR^2$; and
$R^{f1}$ is —$(CH_2)_{y-1}R^2$;
the cyclic ketone having the structure of formula (II) is:

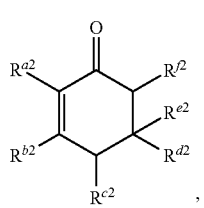

or any isomers thereof, wherein:
$R^{a2}$ is —$(CH_2)_{y-1}R^2$;
$R^{b2}$ is —$(CH_2)_xR^1$;
$R^{c2}$ is —$(CH_2)_{y-1}R^2$;
$R^{d2}$ is —$(CH_2)_xR^1$;
$R^{e2}$ is —$(CH_2)_yR^2$; and
$R^{f2}$ is —$(CH_2)_{x-1}R^1$;
the cyclic ketone having the structure of formula (III) is:

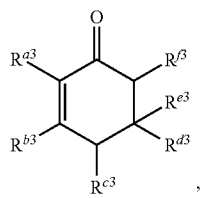
(III)

or any isomers thereof, wherein:
$R^{a3}$ is —$(CH_2)_{x-1}R^1$;
$R^{b3}$ is —$(CH_2)_yR^2$;
$R^{c3}$ is —$(CH_2)_{x-1}R^1$;
$R^{d3}$ is —$(CH_2)_xR^1$;
$R^{e3}$ is —$(CH_2)_yR^2$; and
$R^{f1}$ is —$(CH_2)_{y-1}R^2$;
the cyclic ketone having the structure of formula (IV) is:

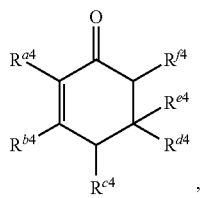
(IV)

or any isomers thereof, wherein:
$R^{a4}$ is —$(CH_2)_{y-1}R^2$;
$R^{b4}$ is —$(CH_2)_yR^2$;
$R^{c4}$ is —$(CH_2)_{x-1}R^1$;
$R^{d4}$ is —$(CH_2)_xR^1$;
$R^{e4}$ is —$(CH_2)_yR^2$; and
$R^{f4}$ is —$(CH_2)_{x-1}R^1$, and
the catalyst comprises:
an apatite; a sepiolite; a chrysotile; a zeolite; a mesoporous silica; a hydrotalcite; or a synthetic talc, or any combinations thereof.

2. The method of claim 1, wherein the contacting of the at least one ketone with the catalyst further produces water as the at least one cyclic ketone is produced, and the method further comprises controlling the amount of water present in the reaction mixture.

3. The method of claim 2, wherein:
controlling the amount of water present in the reaction mixture comprises removing at least a portion of the water present in the reaction mixture; or
the amount of water present in the reaction mixture is less than 5 wt %; or
at least 50% of the ketone having a structure of formula (A) is converted to at least one cyclic ketone in less than 24 hours;
or any combination thereof.

4. A method for producing at least one cycloalkane, comprising hydrodeoxygenating at least one cyclic ketone having a structure of formula (I), (II), (III) or (IV), or any isomers thereof, produced according to the method of claim 1 to produce at least one cycloalkane.

5. The method of claim 1, wherein the catalyst has one or more of the following properties:
(i) a pKa between 8 to 16;
(ii) a $CO_2$ desorption of at least 50° C., wherein $CO_2$ desorption is carried out by adsorbing $CO_2$ to the catalyst at room temperature and heating up to 773 K;
(iii) at least one basic oxygen atom;
(iv) a proton affinity of at least 700 kJ/mol;
(v) is solid;
(vi) is acidic; and
(vii) is amphoteric.

6. The method of claim 1, wherein the catalyst comprises Mg—Al hydrotalcite, Li—Al hydrotalcite, Zn—Al hydrotalcite, Cu—Zn—Al hydrotalcite, Ni—Mg—Al hydrotalcite, or Ni—Mg—Al hydrotalcite.

7. The method of claim 1, wherein the catalyst comprises $Cs_2CO_3$ or KOH impregnated on a hydrotalcite or a zeolite.

8. The method of claim 1, wherein the catalyst comprises a hydrotalcite.

9. The method of claim 8, wherein the hydrotalcite is calcined.

10. The method of claim 1, wherein the catalyst has 0.25 mol % to 2 mol % basic sites.

11. The method of claim 1, wherein:
(i) when x and y are both 1, either $R^1$ or $R^2$ is unsubstituted alkyl;
(ii) when x and y are both 1, $R^1$ is unsubstituted alkyl, and $R^2$ is H; or
(iii) each $R^1$ and $R^2$ is independently H or unsubstituted alkyl.

12. The method of claim 1, wherein:
$R^1$ is:
H,
unsubstituted phenyl,
unsubstituted furan,
furan substituted with alkyl, or
—$CH(R^t)_2$, wherein $R^t$ are each independently unsubstituted furan or furan substituted with alkyl;
$R^2$ is H.

13. The method of claim 1, wherein at least one of the ketones independently having the structure of formula (A) is a ketone having the structure of formula (A-1):

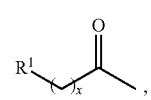
(A-1)

wherein x is an integer greater than or equal to 2.

14. The method of claim 13, wherein $R^1$ is H or unsubstituted alkyl.

15. The method of claim 1, wherein x is 3 to 45, 3 to 21, 3, 5, 7, or 9.

16. The method of claim 1, wherein at least one ketone having the structure of formula (A) is selected from the group consisting of

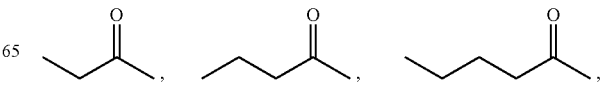

-continued

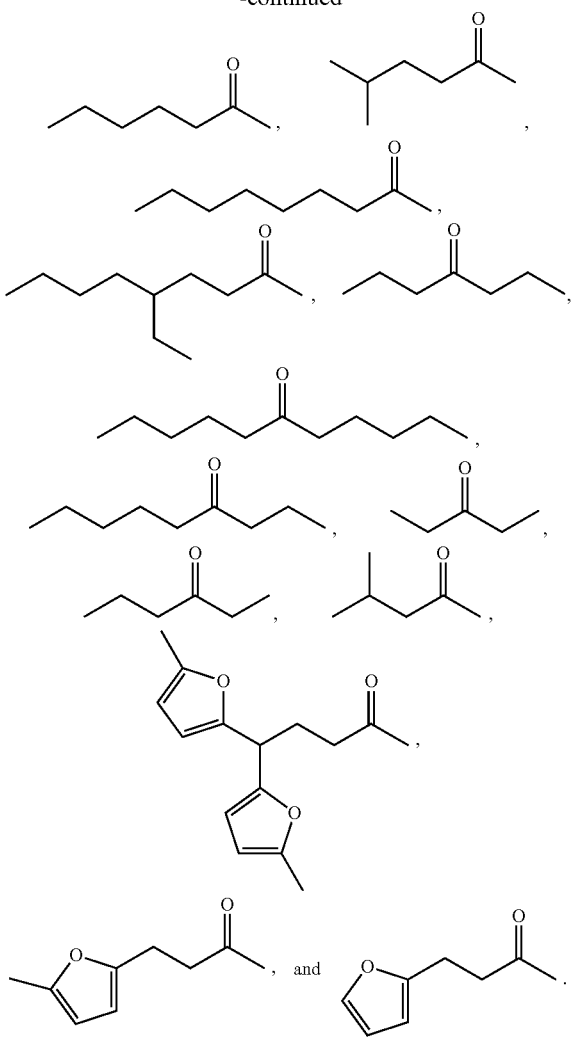

17. The method of claim 2, wherein controlling the amount of water present in the reaction mixture comprises removing at least a portion of the water present in the reaction mixture.

18. The method of claim 2, wherein the amount of water present in the reaction mixture is less than 5 wt %.

19. The method of claim 2, wherein at least 50% of the ketone having a structure of formula (A) is converted to at least one cyclic ketone in less than 24 hours.

20. The method of claim 17, wherein at least a portion of the water present in the reaction mixture is removed by distillation, the use of absorbents, or the use of a biphasic reaction system.

21. The method of claim 5, wherein the catalyst has one or more of the following properties:
(i) a pKa between 8 to 16;
(ii) a $CO_2$ desorption of at least 50° C., wherein $CO_2$ desorption is carried out by adsorbing $CO_2$ to the catalyst at room temperature and heating up to 773 K;
(iii) at least one basic oxygen atom; and
(iv) a proton affinity of at least 700 kJ/mol.

22. The method of claim 20, wherein the catalyst comprises a hydrotalcite.

23. The method of claim 1, wherein the catalyst comprises an apatite.

24. The method of claim 1, wherein the catalyst comprises a sepiolite.

25. The method of claim 1, wherein the catalyst comprises a chrysotile.

26. The method of claim 1, wherein the catalyst comprises a zeolite.

27. The method of claim 1, wherein the catalyst comprises a mesoporous silica.

28. The method of claim 1, wherein the catalyst comprises a synthetic talc.

29. The method of claim 1, wherein the catalyst comprises NaY zeolite, NaX zeolite, KY zeolite, RbY zeolite, CsY zeolite, KX zeolite, RbX zeolite, CsX zeolite, palladium/NaY zeolite, palladium/$NH_4$-β zeolite, potassium oxide supported on zeolite Y, lanthanide imide on zeolite, or nitride on zeolite.

30. The method of claim 1, wherein the catalyst comprises $Na/SiO_2$ $Pd/Na/SiO_2$, $Na/Ca/SiO_2$, or $Cs/SiO_2$.

31. The method of claim 1, wherein the catalyst comprises hydroxyapatite, fluorapatite, or tert-butoxyapatite.

32. The method of claim 1, wherein the catalyst comprises $Mg_3(OH)_4Si_4O_5$, or cobalt(II)-substituted chrysotile.

33. The method of claim 1, wherein the catalyst comprises an amino-functionalized mesoporous silica (MCM-41).

34. The method of claim 1, wherein the catalyst comprises a modified mesoporous silica (SBA-15).

35. The method of claim 1, wherein the catalyst comprises a magnesium organo silicate.

* * * * *